(12) United States Patent
Northen et al.

(10) Patent No.: US 12,097,163 B2
(45) Date of Patent: Sep. 24, 2024

(54) VIBRATION PRODUCING DEVICE WITH SLEEP CYCLE FUNCTION AND TRANSDUCER

(71) Applicants: Michael Northen, Bolinas, CA (US); John Foster, New Orleans, LA (US); Alan Macy, Santa Barbara, CA (US)

(72) Inventors: Michael Northen, Bolinas, CA (US); John Foster, New Orleans, LA (US); Alan Macy, Santa Barbara, CA (US)

(73) Assignee: CoFactor Systems, Inc., Santa Barbara, CA (US)

( * ) Notice: Subject to any disclaimer, the term of this patent is extended or adjusted under 35 U.S.C. 154(b) by 597 days.

(21) Appl. No.: 17/372,497

(22) Filed: Jul. 11, 2021

(65) Prior Publication Data
US 2023/0008214 A1    Jan. 12, 2023

(51) Int. Cl.
*A61H 23/02* (2006.01)

(52) U.S. Cl.
CPC . *A61H 23/0263* (2013.01); *A61H 2201/0149* (2013.01); *A61H 2201/1609* (2013.01); *A61H 2201/165* (2013.01); *A61H 2201/5071* (2013.01); *A61H 2205/027* (2013.01); *A61H 2230/08* (2013.01)

(58) Field of Classification Search
CPC ............ A61H 23/00–06; A61H 2023/002–045
USPC .......................................................... 601/7
See application file for complete search history.

(56) References Cited

U.S. PATENT DOCUMENTS

| | | | |
|---|---|---|---|
| 9,005,101 B1 * | 4/2015 | Van Erlach | A47C 31/123 600/9 |
| 9,956,134 B2 | 1/2018 | Schockley et al. | |
| 9,895,287 B2 | 2/2018 | Schockley et al. | |
| 9,907,725 B2 | 3/2018 | Schockley et al. | |
| 2006/0047201 A1 * | 3/2006 | Eide | A61B 5/031 600/485 |

(Continued)

FOREIGN PATENT DOCUMENTS

| | | | | |
|---|---|---|---|---|
| WO | WO-2004023235 A2 * | 3/2004 | | A61H 23/0245 |
| WO | WO 2006/076567 | 7/2006 | | |
| WO | WO-2013108244 A2 * | 7/2013 | | A61H 19/34 |

OTHER PUBLICATIONS

K.C. Horner. "The emotional ear in stress." Neuroscience &Biobehavioral Reviews. vol. 27, Issue 5, pp. 437-446. (Year: 2003).*

*Primary Examiner* — Valerie L Woodward
*Assistant Examiner* — Paige Kathleen Bugg
(74) *Attorney, Agent, or Firm* — Jaquelin K. Spong

(57) ABSTRACT

A device is described for delivering a therapeutic vibration to a body. The device may include at least two motors in a housing with unbalanced masses coupled to their axles, such that vibration of the masses causes the two motors and housing to vibrate at a beat frequency 80. The motors and housing may be coupled to the body via a platform which places the motors and housings at or near a resonant structure in the body, creating a coupled oscillation between the platform and the body. The vibration may be based on the input signal, such that the system applies the vibration based on the input signal to the user, wherein the signal may be an audio or video signal. The system may be configured to measure and manipulate the flow of cerebral spinal fluid.

14 Claims, 29 Drawing Sheets

(56) References Cited

U.S. PATENT DOCUMENTS

| | | | |
|---|---|---|---|
| 2012/0245410 A1* | 9/2012 | Davis | A61H 99/00 |
| | | | 600/28 |
| 2016/0030281 A1* | 2/2016 | Shafieloo | A61H 23/0245 |
| | | | 601/48 |
| 2019/0076643 A1* | 3/2019 | Siegle | A61N 1/00 |
| 2019/0262212 A1* | 8/2019 | Schroeder | A61H 1/0296 |
| 2020/0246579 A1* | 8/2020 | Cohen | A61H 1/005 |
| 2021/0282999 A1* | 9/2021 | Bouchet | A61H 23/006 |
| 2021/0290482 A1* | 9/2021 | Wang | A61H 23/0263 |
| 2022/0304888 A1* | 9/2022 | Faii Ong | A61H 23/0254 |

* cited by examiner

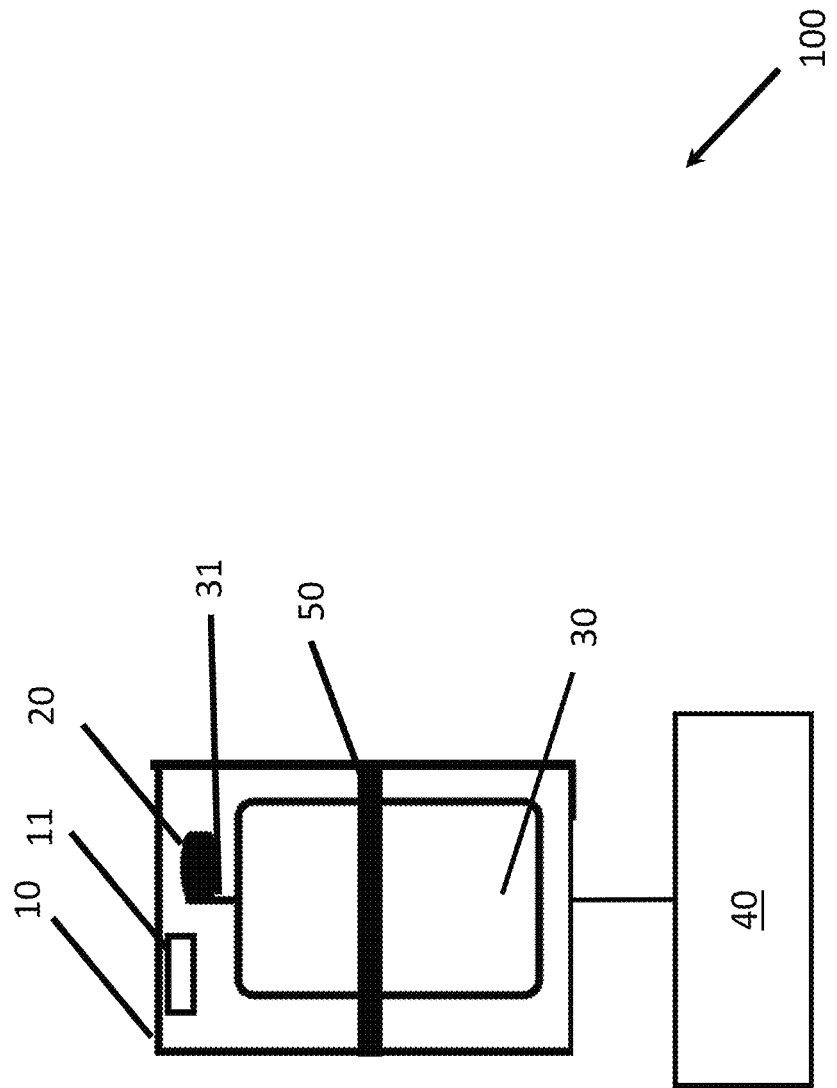

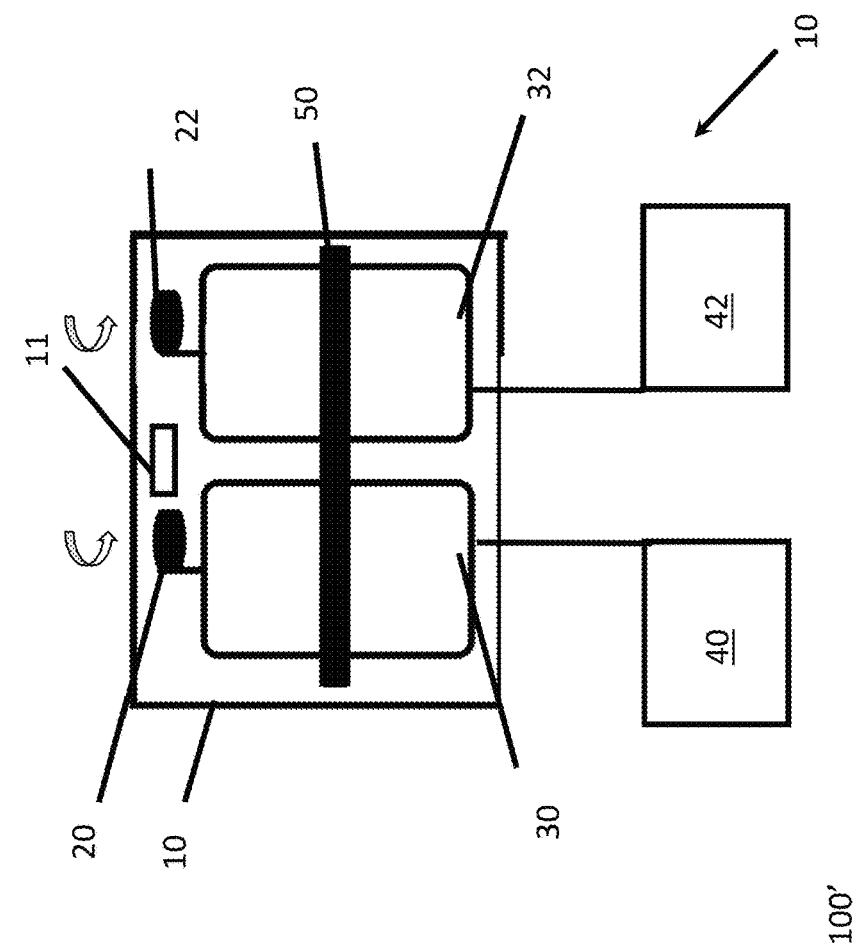
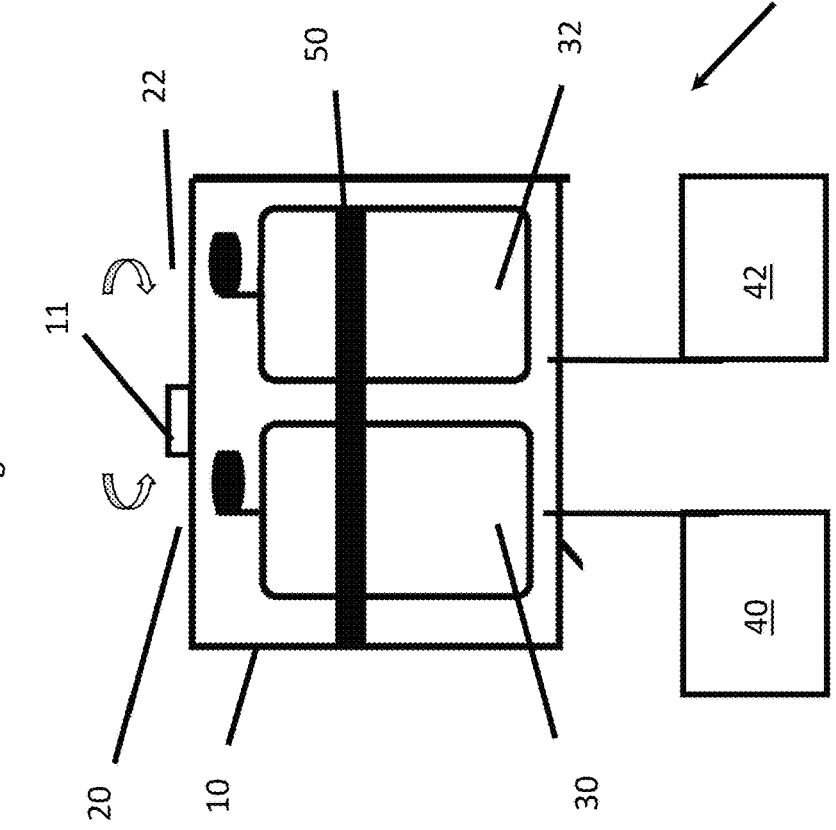

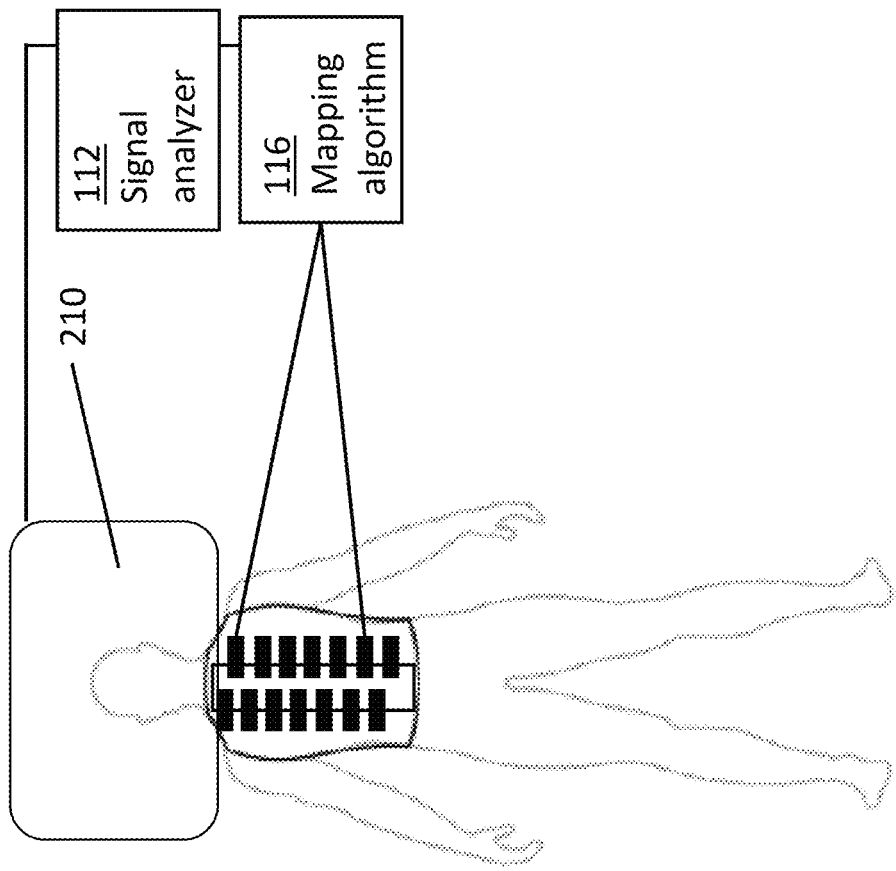
Fig. 13B Visual stimulus
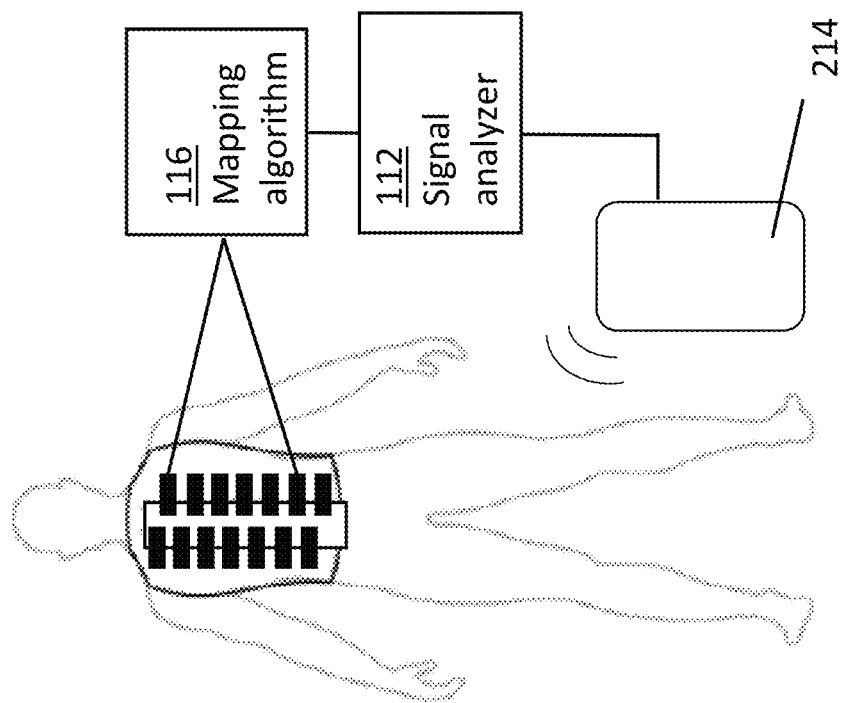
Fig. 13A Audio stimulus

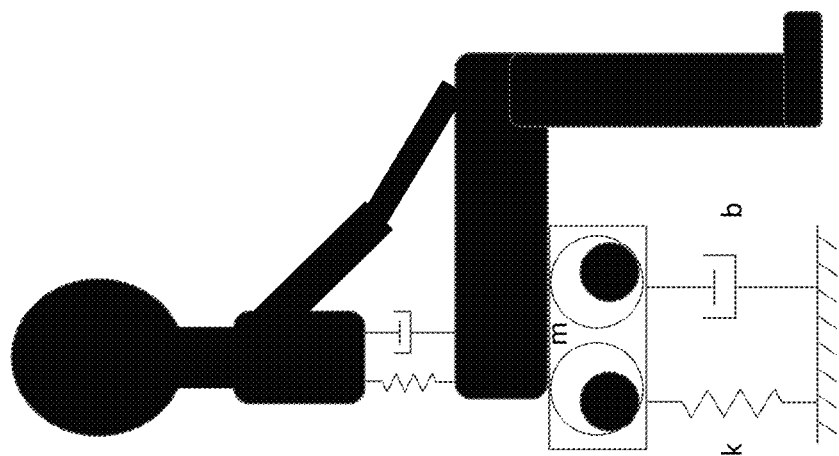
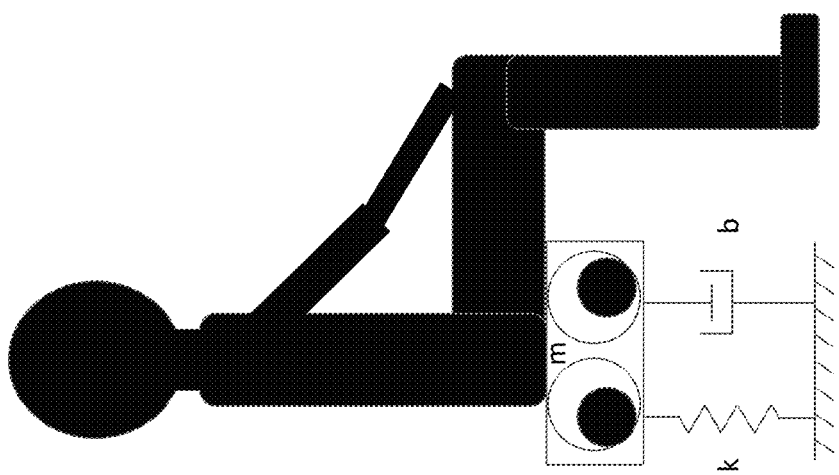
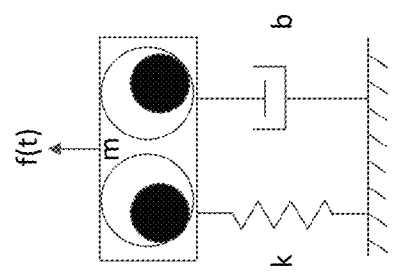

VIBRATION PRODUCING DEVICE WITH SLEEP CYCLE FUNCTION AND TRANSDUCER

STATEMENT REGARDING FEDERALLY SPONSORED RESEARCH

Not applicable.

STATEMENT REGARDING MICROFICHE APPENDIX

Not applicable.

BACKGROUND

This invention relates to a system for applying therapeutic vibration and/or compression.

It has long been appreciated that massage of muscles and limbs can provide perceptibly pleasant and therapeutic effects. These effects may include improved blood or lymph circulation, improved blood flow, reduced blood pressure or even just a general feeling of well-being. The massage is generally performed by a professional masseuse or by a mechanized chair, as for example found in airports to assist tired travelers who may have been sitting for many hours.

Less well known are the medical therapeutic effects of massage or compression therapy. Several patents have been granted which are directed to the application of massage to improve the status or outcome of a patient with some medical disorder. Many medical disorders have as one symptom the poor circulation of bodily fluids. Exemplary such disorders may include chronic obstructive pulmonary disease, diabetes and heart disease for example. It has been reported that vibrational and/or compressive massage may improve blood flow in ischemic patients, and lymph flow in persons suffering from lymphedema.

Chronic obstructive pulmonary disease (COPD) limits the ability to breathe over time. COPD is characterized by mucus in the lungs that clogs the airways and traps germs, leading to infections, inflammation, respiratory failure, and other complications. It has been hypothesized that massage therapies may help loosen mucus and allow normal breathing.

To this end, U.S. Pat. No. 9,895,287 to Shockley, et al. describes a harness worn on the inner torso with a plurality of engines which apply an oscillating force to at least one treatment area of the patient in order to mobilize secretions in an airway. In this device, the oscillation force (amplitude and/or frequency of the motor) can be adjusted by the user or by a care provider. U.S. Pat. Nos. 9,956,134 and 9,907,725 also to Shockley et al, describe other features of this device. All are directed at assisting the mobilization of secretions in a patient suffering from, for example, chronic obstructive pulmonary disease (COPD), using this vest harness equipped with a plurality of simple, rotating motors.

However, the effectiveness of massage therapy in treating these disorders has not been thoroughly studied. This disclosure describes a novel device for the repeated application of a therapeutic vibration and/or compression to achieve a wide range of outcomes, including relief from the buildup of mucus in persons suffering from COPD.

SUMMARY

Disclosed herein are embodiments of a tactile stimulation system using a plurality of motors coupled to a rigid enclosure. The motors may be equipped with a mass rotating on an axle about a point which is not at the center of the rotational inertia of the mass. The mass may therefore impart a vibration or wobble to the motor.

Accordingly, disclosed here are several embodiments of vibrational and/or compressive devices with a number of novel attributes. In one embodiment, a motor may be enclosed in a case and attached to a garment or other "platform", wherein the motor has a rotating axle with an eccentrically mounted mass on the axle. The asymmetrically rotating mass produces a vibration that can cause a therapeutic vibration and/or compression to be applied to the body of the patient.

In another embodiment, the rotating masses may comprise two or more rotating masses. These rotating masses may rotate with different frequencies, such that a beat frequency 80 arises in the structure and is transmitted to the body. These beat frequencies may be low, and consistent with naturally occurring body rhythms such as respiration and heartbeat.

In some embodiments, the vibrational and/or compressive devices may be used in an architecture that learns, through feedback, of its physiological or emotional effects on the user. In other embodiments, the architecture encodes various stimulating sensations as tactile sensations delivered through a plurality of the vibrational and/or compressive devices. In other embodiments, the architecture encodes environmental stimuli such as sights and sounds as tactile sensations delivered through the plurality of the vibrational and/or compressive devices.

In another embodiment, the vibrational and/or compressive device may be used in conjunction with a sensor that measures some attributes of the user's body, comfort or function. The vibrational and/or compressive device may then be adjusted to achieve a predefined state within the user, based on the output of the sensor. This state may be, for example, repose, lower heart rate, lower blood pressure, and the like.

In another embodiment, a stimulus is applied to the user, and the stimulus is also analyzed to characterize some attribute of the stimulus. For example, if an auditory stimulus is applied, the signal is also analyzed by a spectrum analyzer, such that the audio power in a certain auditory band is measured. The vibrational and/or compressive device may then be driven by a motor drive signal or algorithm, or waveform that is based on the spectral content of the audio signal. Visual stimulus may be treated in an analogous way.

Exemplary measurements include ventilatory effort, respiration, heartbeat, brainwaves, blood pressure, skin sweat, blood flow, muscle tension, eyeblinks, pupil diameter, bioimpedance, blood volume pulse, cerebral spinal fluid pressure. Many more possible measurements and adjustments are envisioned, several of which are described in the exemplary embodiments discussed below.

BRIEF DESCRIPTION OF THE DRAWINGS

Various exemplary details are described with reference to the following figures, wherein:

FIG. 1A is a simplified schematic diagram of a vibrational or compressive device using at least one motor with an eccentric rotating mass (ERM), and attached to a controller;

FIG. 6A and FIG. 6B are an illustrations showing design choices with respect to the rotation sense of the two motors;

FIG. 13A is a simplified schematic diagram of the different components in a system architecture designed to augment auditory sensations; FIG. 13B is a simplified schematic diagram of the different components in a system architecture designed to augment visual sensations;

FIG. 20A, FIG. 20B, and FIG. 20C show the mechanical coupling to the body.

It should be understood that the drawings are not necessarily to scale, and that like numbers may refer to like features.

DETAILED DESCRIPTION

Figure 1B:
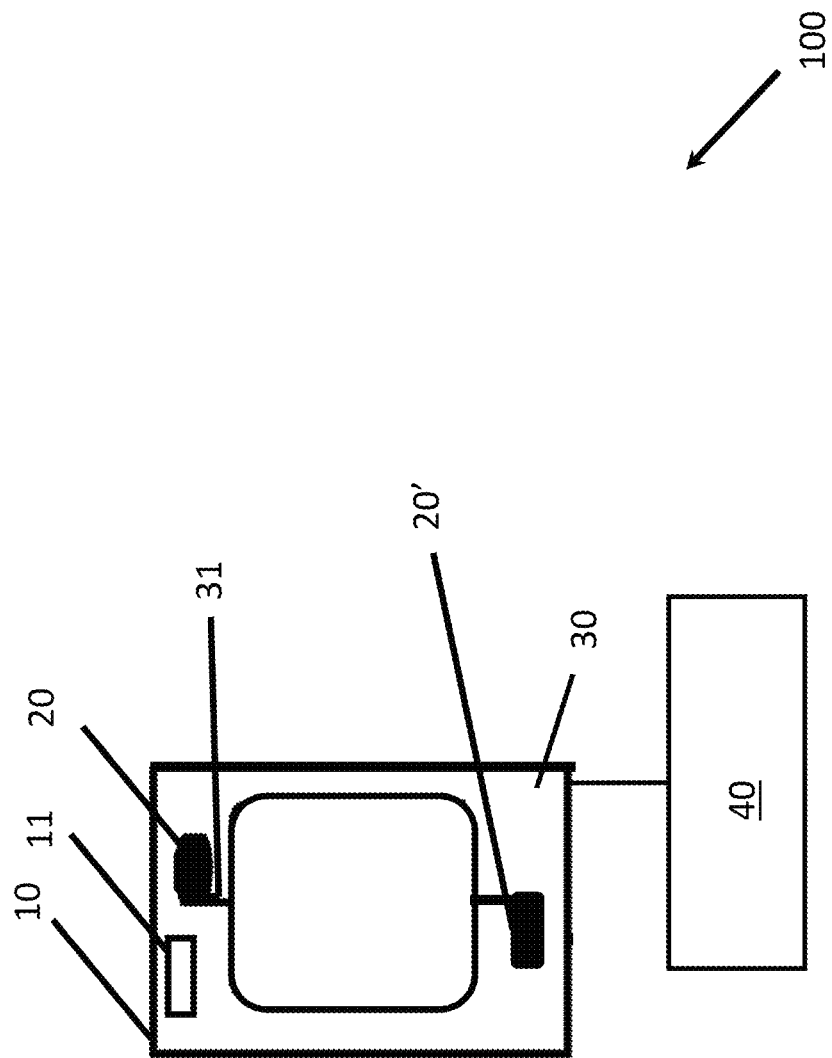
FIG. 1B is a simplified schematic diagram of a vibrational or compressive device using at least one motor with two eccentric rotating masses (ERM), and attached to a controller.

It is an object of this invention to stimulate a user's mechanoreceptors, and/or baroreceptors of the heart, and/or spinal ganglia, using a device which generates a plurality of vibrations or compressive pulses. The device may be driven by a function which is based on some stimulative characteristic, or some desired therapeutic goal, or in order to transmit information with tactile sensations. As such, the function may be arbitrarily complex, and considerations involved in determining the details of the function are described more fully below.

As used here, the term "actuator" is used synonymously with "motor" "vibrational device," and "vibration-producing device". The term "compression device" is used below to emphasize that the motion may not be strictly oscillatory or sinusoidal or regularly repeating. In fact, the waveform or motor drive signal can be quite complex. The vibrational or compressive device may be driven by a "function" or "waveform", wherein the terms are used interchangeably to refer to the signals sent to the motor by the motor controller to control its behavior. The function or waveform may or may not be regular, recurrent and/or oscillatory. This signal may also be referred to as a "motor drive signal". Accordingly, the vibration-producing device may be a motor with an ERM which is controlled by a computer using a motor drive signal or motor drive waveform.

A "third party" may be a bystanding personnel who are not the user or the controller. Thus the "third party" may be a trained medical professional, or a clinician, for example. The vibration producing devices may be arranged in a line, serially, single file, and on one or (in two lines) on both sides of a centerline of symmetry of the body. Alternatively, they may be disposed in locations where they can interact with naturally occurring physiological resonance structures, as described below. If located adjacent to, near to, or on top of for sample, one of these naturally occurring resonant structures, the vibration producing device may interact with this naturally occurring structure to become a system of coupled oscillators, which may enhance the therapeutic effect.

In many embodiments, this actuator or vibrational device is a motor with a mass mounted on the axle of the motor. The mounting of the mass may be off center, such that the inertia of the spinning offset mass causes a wobble or a vibration in the motor. This device may be referred to herein as an eccentric rotating mass (ERM). It should be understood that this eccentric rotating mass can have any shape, including but not limited to ellipsoidal or circular. The defining feature is that the inertia of the spinning mass is not rotationally symmetric, and is therefore not balanced. In other words, the asymmetric mass may be coupled to the axle at a point offset from its center of mass. In some embodiments, the eccentric mass may be a simple circular shape, but mounted at a point not at the center of symmetry. In other embodiments, the mass may be an ellipse or a polygonal shape, or indeed any arbitrary shape. But the center of rotation is generally offset from the center of rotational inertia.

This disclosure is organized as follows. The details of the novel vibrational and/or compressive devices using an ERM are described first, as well as a number of design alternatives. This discussion is with respect to FIGS. 1-8. Then, a number of delivery platform options are described, that is, how the vibrational and/or compressive devices are deployed with respect to the user. This discussion is with respect to FIGS. 9 and 10. Then, a number of system architectures are described, that is, how the delivery platform is used to accomplish a therapeutic goal. This discussion is with respect to FIGS. 11-15. The methods associated with these architectures are described with respect to FIGS. 16 and 17. Finally, a number of applications are described that use the components, delivery platforms, system architectures and methods of FIGS. 1-17.

In some embodiments, the vibrational and/or compressive devices may be used in an architecture that learns, through feedback, of its physiological or emotional effects on the user. In other embodiments, the architecture encodes stimuli as tactile sensations delivered through a plurality of the vibrational and/or compressive devices. In other embodiments, the architecture encodes environmental stimuli such as sights, sounds, acceleration or rotation, and maps them as tactile sensations delivered through the plurality of the vibrational and/or compressive devices. In either embodiment, the behavior may alternatively be selected by the user, based on some piece of bioinformation, or it may be chosen by a decision-mapping unit, based on the piece of bioinformation.

In some embodiments, an accelerometer may be used to accurately characterize the motion imparted by the vibration and/or compression device or wobbling motor. In other embodiments, the motion can be characterized by monitoring performance metrics of the motors or devices themselves.

Complex patterns and sequences of waveforms or motor drive signals may also be used, and a motor controller may execute a rather complex algorithm, aimed at achieving a certain state in the user. This controller may also make use of machine learning, artificial intelligence, and deep learning techniques. In these embodiments, the pattern or sequence of waveform or motor drive signals may be altered based on the known response of the subject to previously applied waveforms or patterns.

The general goal of this computer algorithm may be to move the user towards a specific physiological and/or psychological state.

In another embodiment, the user may directly select a specific profile or sequences of vibration frequencies and/or amplitudes.

The vibrating device may also be used in conjunction with other components such as an auxiliary control unit, that may include a heater and/or cooler, especially thermoelectric or peltier heater/cooler. An acoustic gel or other acoustic medium may also be used in the device to better transmit the vibration to other parts of the body.

The vibrating device may be used on many delivery platforms. For example, the vibrating device can be attached to an elastic lining of a vibration and/or compression vest that fits snugly around the torso. It may alternatively be fitted into a bed mattress or a chair, or a cushion. The device or delivery platform may be sized according to individual user's body size.

In some embodiments the device uses power from an outlet. In other embodiments the device uses battery power or a solar panel.

As mentioned previously, the waveforms used to drive the vibrating devices may be regularly repeating such as sinusoids, or they may be arbitrarily complex. In some embodiments, the waveform or motor drive signal is determined according to some measurable feature of a sensory stimulation applied to the user while the user is receiving the vibration or vibration and/or compression. As described previously, the device may adjust its behavior based on the status of the user, and this embodiment is referred to herein as the "self-aware" or "intelligent" vibration and/or compression device.

In these "Self aware" embodiments, the system may again be configured to apply a vibration to a body. The system may include a platform including at least one vibration producing device producing a vibration having a frequency and amplitude, wherein the vibration is applied to at least a portion of the body. They system may also include at least one sensor which senses at least one piece of bioinformation and generates an output based on the at least one piece of bioinformation, wherein the at least one piece of bioinformation is related to at least one of a physical, psychological, emotional and environmental status of the body, and wherein at least one of the frequency and amplitude of the vibration is based on the at least one piece of bioinformation.

The system may further include a mapping unit that relates the at least one piece of bioinformation sensed by the sensor to an algorithm that produces a motor drive waveform that drives the vibration producing device, based on the at least one piece of bioinformation. It may further include a controller programmed to control the vibration producing devices, and to execute an algorithm defined by a sequence of vibrations, wherein the algorithm and sequence of vibrations is chosen based on the output of the at least one sensor.

The bioinformation may be based on at least one of Heart Rate (HR), Electrodermal Activity (EDA), and Heart Rate Variability (HRV), blood pressure, respiration rate, eye blinking, oxygenation, respiratory effort, electroencephalography (EEG), piloerector muscle activity, electrogastrography (EGG), reaction time, electrooculography (EOG), pupil diameter, micro/macro saccade activity, posture, skin potential, electromyography (EMG), pre-ejection period (PEP), stroke volume (SV), cardiac output (CO), left ventricular ejection time (LVET), blood pressure (BP), vascular resistance, arterial and/or venous blood flow, bioimpedance (magnitude and/or phase), cerebral spinal fluid flow and/or pressure.

Alternatively, the waveforms or motor drive signals may be a combination of amplitudes, frequencies and phase relationships specific to a user, or have attributes (such as frequency and/or amplitude) selected to have specific effects on the user. The waveforms or motor drive signals may include different frequencies and/or amplitudes and/or phase relationships, and these attributes may be chosen to modify a user's state of being. The state of being may include the physiological state of the user, the emotional state of the user, and the mental state of the user, for example. The state of being may also include the arousal and valence state of the user, or their motivational state.

Figure 1C:
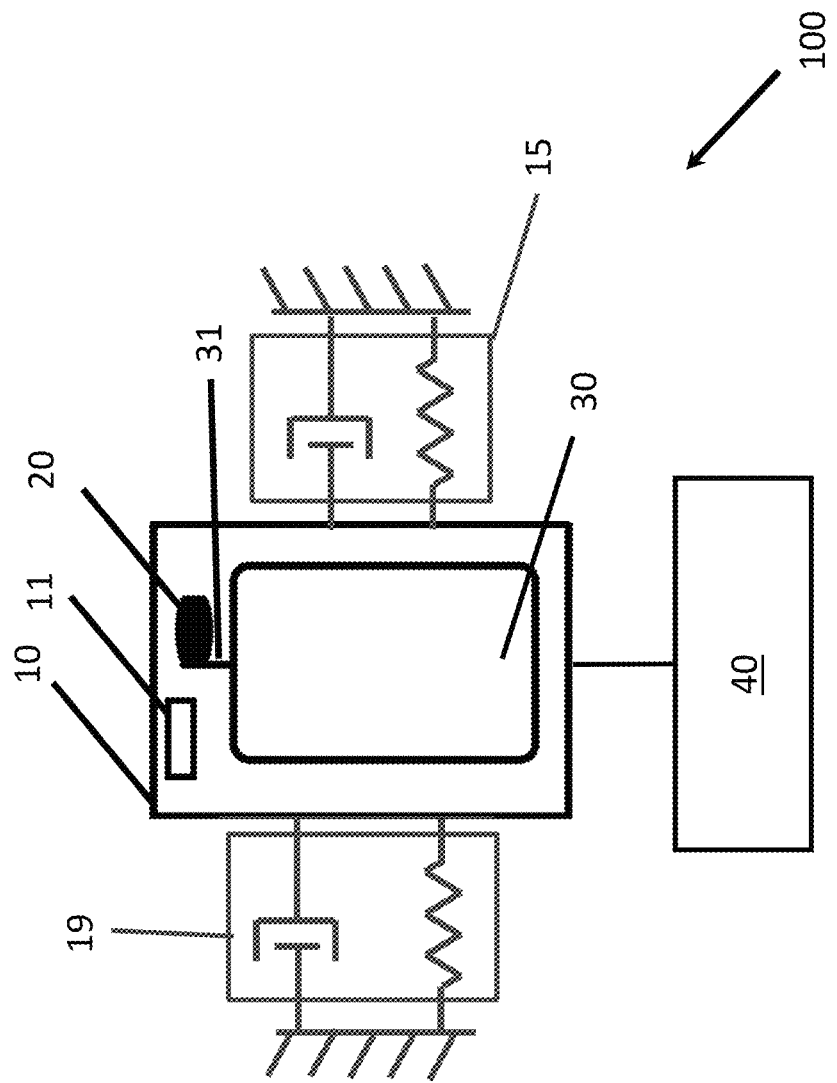
FIG. 1C is a simplified schematic diagram of a vibrational or compressive device using at least one motor with an eccentric rotating mass (ERM), and how the system is coupled.

In the following description of the preferred embodiments, reference is made to the accompanying drawings which form a part hereof, and in which is shown by way of illustration a specific embodiment in which the invention may be practiced. It is to be understood that other embodiments may be utilized and structural changes may be made without departing from the scope of the present invention. The reference numbers are used to refer to the following features depicted in the drawings, and a partial list is provided below:

- 10 backing, chassis or housing for vibrational device
- 11 accelerometer
- 20, 22, 24, 26, 28 eccentric masses
- 30, 32, 34, 36, 38 motors
- 31, 33 and 35 axles
- 40, 42, 44, 46, 48 motor controllers
- 50 coupling mechanism between motors and housing
- 100, 100', 100", 100"' embodiments of vibrational and/or compressive device
- 101 vest using vibrational and/or compressive devices
- 103 fitting methodology
- 110 computer or controller
- 112 analyzer
- 116 algorithm selector, mapper or decision maker
- 118 auxiliary device, e.g. heater or cooler
- 210, 211 visual stimulus or detector
- 214, 215 auditory stimulus or microphone
- 220 CSF sensor
- 310 chair using vibrational and/or compressive devices
- 312 mattress using vibrational and/or compressive devices
- 314 cushion/pillow using vibrational and/or compressive devices Motors with Eccentrically Rotating Mass FIG. 1 includes FIG. 1a, FIG. 1B and FIG. 1C. FIG. 1A shows a first exemplary embodiment of a therapeutic vibrational and/or compressive device 100, using an eccentric rotating mass (ERM) 20. As shown in FIG. 1A, a motor 30 has an axle 31 which is rotated by the motor 30. Attached to the axle 31 is an eccentric, non-circular mass 20. As shown in FIG. 1A, the mass 20 may be attached to the axle 31 in a fashion such that the rotation is asymmetric. In other words, the axle 31 is not located at the center of symmetry of the mass 20, or at its center of mass. As a result, the force of the unbalanced weight of the asymmetric rotating mass 20 may cause a wobbling of the motor 30.

In some embodiments, the mass 20 may be ellipsoidal, but this is not necessary. The only requirement is that the rotational inertia may not be rotationally symmetric. In other words, the rotationally asymmetric mass may cause the motor assembly to vibrate at some frequency, because of the weight imbalance of the eccentrically rotating mass (ERM) 20. The frequency of vibration may depend on the embodiment, as described below.

The mass 20 may be machined or stamped in the usual fashion. The mass may also have a threaded set screw hole formed therein, which allows the mass to be fastened securely to a flat face of the axle by a set screw, for example. The mass may also be glued or epoxied to the axle, or any other convenient attachment method.

The motor 30 is typically an ordinary DC motor, having the usual stator and windings. As mentioned, the motor axle may have a single flat face, to provide a detent position for a set screw. However, other sorts of vibrating mechanisms may also be used. Among those may be a magnetic voice coil, brushed and brushless DC motors, a linear resonance mass or a piezoelectric (PZT) actuator. These devices may also be made to vibrate by mechanical coupling to an asymmetric mass.

The motor 30 may be attached to a backing, chassis or housing 10, and this backing may be attached to the delivery platform. The backing, chassis or housing may be referred more generally as a substrate or a mechanically capable material, meaning that it may be a piece of material capable of supporting the vibrating devices without fracture, cracking or breaking. The substrate or a mechanically capable material may also have sufficient rigidity to transmit the vibration to the body, rather than absorb it in elastic or plastic deformation. Wood or polycarbonate plastic sufficiently thick to avoid cracking (i.e. 1-5 mm thick for example) may have sufficient mechanical competency. The substrate or a mechanically capable may also serve as the "case" described below, wherein the case is an enclosure designed to protect the motor, axle and ERM. These terms are used interchangeably to refer to a support for the vibrating motors that transmits the vibration to the body of the user. Accordingly, the backing, chassis, housing or substrate or a mechanically capable material 10 may be a piece of mechanically capable material having a wide variety of types, shapes and materials.

The rigid material may be plastic, plywood or metal, for example. The material should be capable of supporting the weight of the motor and the forces associated with the vibration. The material should also be appropriately rigid and elastic to transmit the vibration effectively to the user. In other embodiments, the stretchy elastic material (vest, stretched chair back) holds separate individual motors against the body, effectively turning the body into the substrate or a mechanically capable that couples the motors together.

The attachment methodologies may be sewing, stapling, adhering, gluing, Velcro, zip tying or any other convenient method that attaches the vibrational and/or compressive devices 100 to the backing or chassis 10. Or the attachment methods may be snaps, buckles, belts. The attachment mechanism should preferably be relatively rigid, such that the vibration is effectively coupled to the backing or chassis 10. The vibrating device 100 may be removable, such that it can be relocated if desired. If the vibrational device 100 is in a garment with pockets, the user can move the device to another location such as to the pocket. The attachment mechanism is shown schematically as reference number 50, and should be understood to refer to any of the attachment mechanisms listed above, or some other means whereby the vibrating motor is firmly and relatively rigidly attached to the backing, chassis or housing 10. In one embodiment, the attachment mechanism may be the well known and inexpensive cable tie downs, also known as "zip ties".

In one embodiment, there may be a 2-step attachment process. The motors may be attached or captured by a housing or case, which is then attached to a garment or "platform". The case may be used to protect the eccentric rotating mass 20.

Then, the motor and housing may be attached to the platform, i.e. to the garment, chair, cushion for example. In some cases the motors are in the same housing and coupled in this manner.

In other cases the motors are in their own individual cases and then coupled through another substrate or a mechanically capable material.

In other cases the motors/casings are coupled through the user's body.

It may be helpful to hold the vibrating vibrational and/or compressive device with pressure against the body using some deformable mechanism. For example, the vibrational and/or compressive device may have a tension member holding the device against the body. Alternatively, an elastic material may be used or laces that may draw the garment up like a corset. Ideally, the delivery platform can hold the vibrational and/or compressive devices securely against the body but under a layer of fabric, plastic, nylon, or whatever the conformable materials are used by the delivery platform. The attachment mechanism is also ideally lightweight, and rigid, so as to transmit as much of the motion as possible from the vibrational and/or compressive device to the user. The attachment mechanism may thereby transmit the vibration or compression to the body in a way that minimizes interference and avoids irritation or abrasion. Other sorts of attachment and deformable mechanisms are contemplated, but the options are too numerous to list here.

The delivery platform may be, for example, a chair, a mattress, a cushion, or some other delivery platform which affords the device 100 close disposition to a body.

The backing, chassis or housing 10 may also support a sensing device 11, which may sense the motion imparted to the delivery platform, chassis or housing 10. The sensor may be, for example, an accelerometer. This accelerometer may be used to measure the amplitude of the vibration caused by the rotating mass 20 spinning on axle 31 by motor 30. The sensed acceleration may provide a feedback signal to the motor controller 40, if precise motion control is required.

In other embodiments, the accelerometer 11 may not be necessary, as the motion information can also be inferred from measurements of the motor 30 properties as it spins.

The motor 30 may be, for example, a DC motor which is driven by a controller 40, which may deliver a current or a voltage to the motor 30 windings. These details will be discussed more fully below. The driving voltage or current may have a constant value, resulting in a relatively constant rate of rotation of the motor 30 and the mass 20. However, more complex waveform or motor drive signals may also be envisaged, and several are depicted in FIG. 3.

FIGS. 1B and 1C depict alternative embodiments of the vibrational device 100. FIG. 1B shows an axle 31 with two ERMs 20 and 20' mounted on opposite ends of the axle 31. In the case shown in FIG. 1B, the masses are mounted with a 180 degree phase relationship to impart a wobble to the motor 30. It should be understood that this is exemplary only, and that the additional mass 20' may be mounted with an arbitrary phase relationship with respect to ERM 20. Accordingly, in this embodiment, two off-center shapes 180 degrees opposed at different axial positions along a motor shaft accomplish the wobble/vibration. When spun, such a geometry would drive an oscillatory rotation of the shaft (wobble) perpendicular to the long axis of the motor 30.

FIG. 1C shows schematically how the vibrating device 100 can be represented as a spring-mass-damper system. The spinning of the eccentric rotating mass 20 creates oscillations in the vertical axis. By placing the vibrating device 100 on a cushion, padded seat, or other surface 15 that can be represented as a spring mass damper 19, a resonance will occur that is mechanically coupled into the user. The human body resonates at various frequencies, as described in greater detail below. By matching these frequencies it is possible to create mechanical oscillations throughout the body. These mechanical oscillations in the human body are then coupled to other systems, such as the skeletal, respiratory, circulatory, nervous, lymphatic, and endocrine systems.

Figure 2:
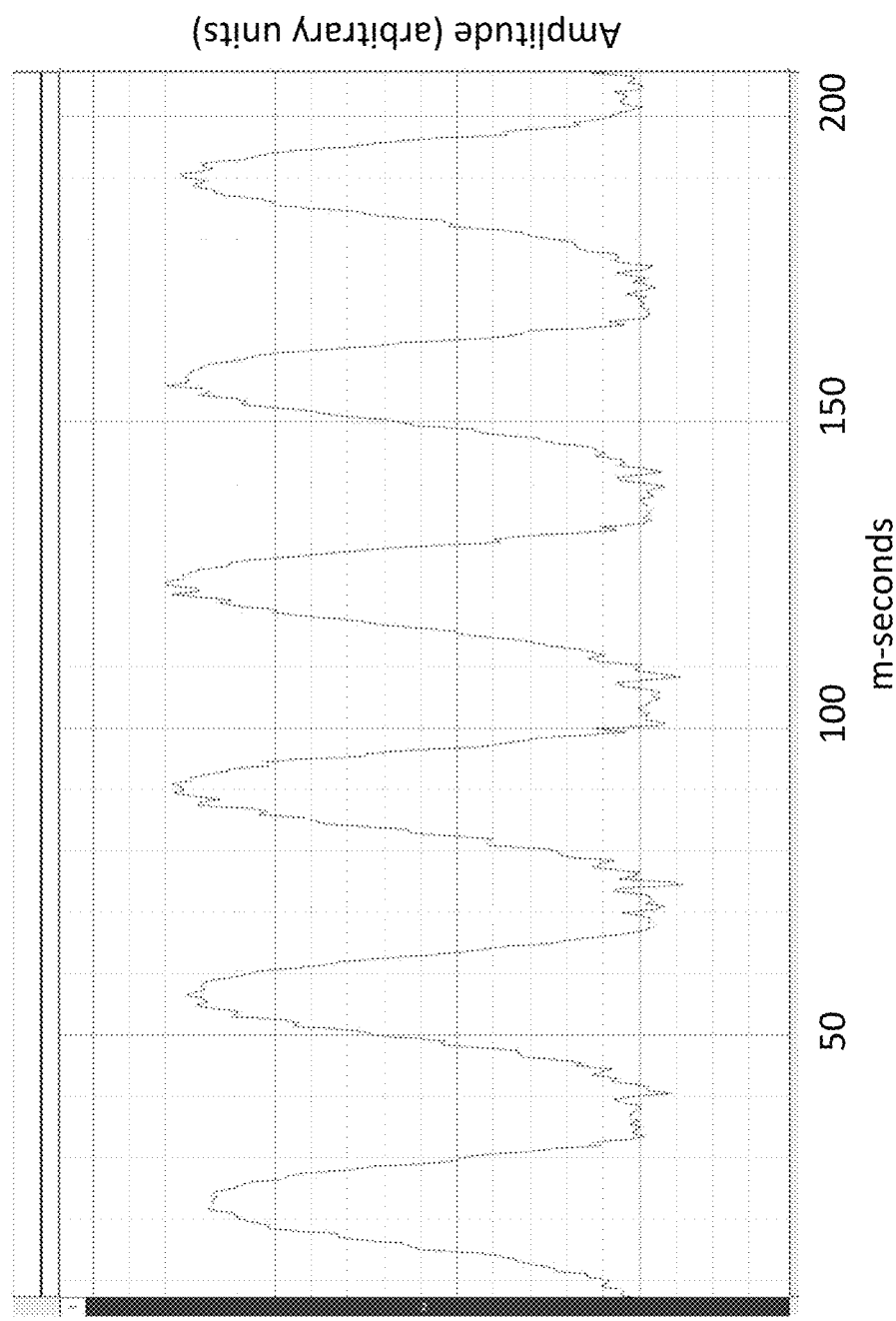
FIG. 2 is a plot of the acceleration of the device with respect to time.

FIG. 2 is a graphical depiction of the acceleration of the device shown in FIG. 1. That is, FIG. 2 shows the acceleration of the rotating mass 20, (or likewise the acceleration of the entire assembly of motor and casing). The magnitude of the acceleration is shown (in arbitrary units) as a function of time, as the mass 20 rotates on axle 31 driven by motor 30. As can be seen in the plot, the acceleration reaches a maximum at about every 35 msec, corresponding to a frequency of about 30 Hz. The spacing between the acceleration peaks corresponds to the revolutions per minute of the motor. This acceleration may be associated with the vibration, or wobble, of the motor, as a result of the eccentrically mounted mass.

Figure 3A:
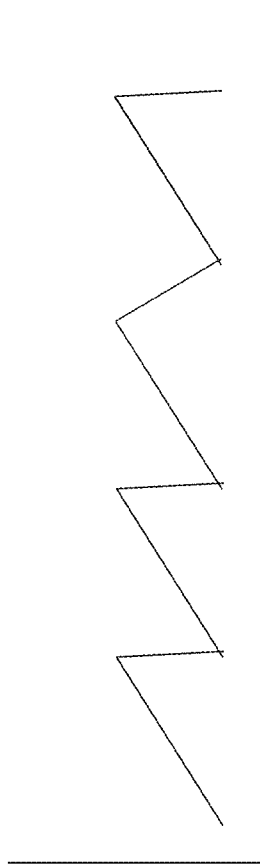
FIG. 3A, FIG. 3B and FIG. 3C are a simplified schematic diagram of exemplary functions which can be used to drive the motors.
Figure 3B:
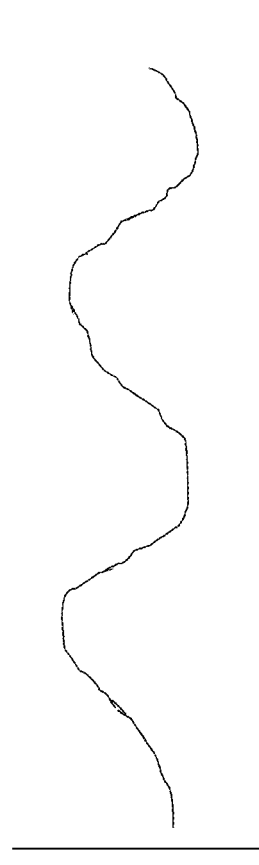
Figure 3C:
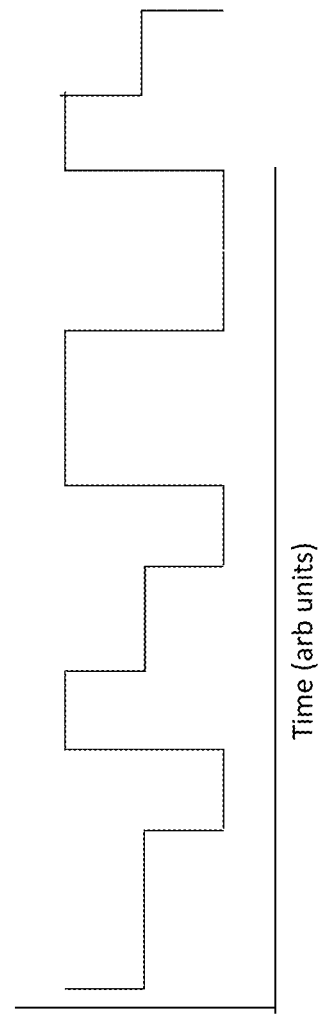

FIG. 3, including FIGS. 3A, 3B and 3C, is a simplified diagram showing various motor drive waveforms or motor drive signal options which can be used to drive motor 30. In each plot, the y-axis may be, for example, frequency or amplitude, as a function of time, and accordingly the plots may illustrate qualitatively how different motor behaviors can arise. One particularly interesting embodiment is wherein the functional relationships illustrated in FIG. 3 are applied to the frequency, rotation rate, or rpm, of the motors. For example, using the relationship of FIG. 3A, the rpm of a motor is repeatedly driven in a sawtooth manner, starting at a lower frequency and ramping up to a higher frequency, then dropping quickly to the lower frequency and ramping again.

Accordingly, FIG. 3 illustrates qualitatively some of the different functions that can be used to drive the motor, 30. These plots may also be used to drive the beat frequency 80, as described below with respect to FIG. 5 and in the two-motor embodiment. FIG. 3A shows a modified sawtooth function, employing ramps of different slope, as the waveform driving the motor 30. FIG. 3B shows a sinusoidal function used to drive a motor. FIG. 3C shows a square wave function with a variable duty cycle which can also be used to drive a motor. Any or all of these waveforms or motor drive signals, or combinations thereof, or some other waveform or motor drive signal not shown here, may also be used to drive motor 30. The waveforms may be of arbitrarily complex shape, and may or may not be repetitive in an ongoing way. These waveforms or motor drive signals may be generated by a controller, for example controller 40 shown in FIG. 1. This may also be referred to as a motor drive signal.

Figure 4:
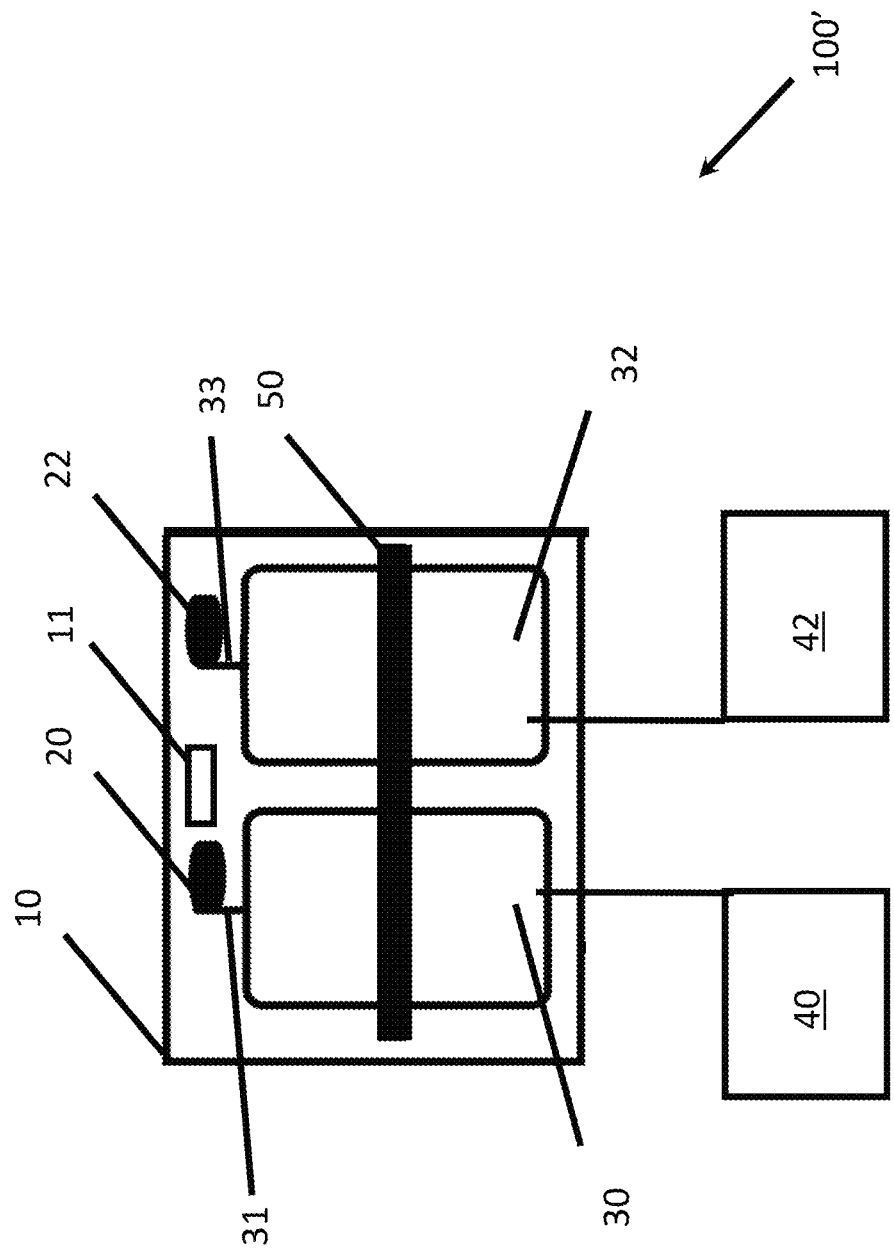
FIG. 4 is a simplified schematic diagram of two motors with eccentric rotating masses.

FIG. 4 is a simplified schematic diagram of a second embodiment 100' of the vibration and/or compression device using eccentric rotating masses. FIG. 4 shows a first motor 30, similar to motor 30 depicted in FIG. 1. However, in this embodiment there may be a second motor 32 similar to first motor 30 and disposed adjacent to first motor 30. Motor 32 may also have an eccentric rotating mass 22 which is obliquely mounted on axle 33 of motor 32. Accordingly, both motor 30 and motor 32 have obliquely mounted masses 20 and 22 that rotate with an unbalanced force, such that both motor 30 and motor 32 tend to wobble.

Controllers 40 and 42 may control motors 30 and 32, respectively. In particular, controller 40 may drive motor 30 at a first frequency $f_1$, and controller 42 may drive motor 32 and a second frequency $f_2$. As a result, the backing, chassis or housing 10 may vibrate at the different frequency between the two frequencies $f_1$ and $f_2$, because of interference between the modes. This interference may cause harmonics, or beat frequencies to arise from their interactions, as is well known in control theory and signal processing. Accordingly, the interaction between these vibrating masses, the backing, chassis or housing 10 may have a vibration at the beat frequency 80, that is the frequency $f_1$ of motor 30 minus the frequency $f_2$ of motor 32. Accordingly, backing, chassis or housing 10 may vibrate at a much lower frequency than either the first frequency applied to motor 30, or the second frequency applied to motor 32.

The beat frequencies are also referred to herein as "beat modes" meaning that they arise from the interference of the two frequencies of the plural motors. The beat mode may have a characteristic frequency and amplitude, which may be modified by changing the frequency and/or amplitude of at least one of the coupled motors.

In other words, because motor 30 and motor 32 are both coupled to the backing, chassis or housing 10, their vibrations will interact. In particular, if motor 30 is driven by first frequency $f_1$ by motor controller 40, and motor 32 is driven by a second frequency $f_2$ by motor controller 42, the effect on the backing, chassis or housing 10 may be a beat frequency 80, that is the difference between the frequency $f_1$ of the signal applied to motor 30 and the signal $f_2$ applied to motor 32.

This assembly of the two motors with eccentric rotating masses, but rotating at different frequencies and coupled through backing 10 may comprise a second embodiment 100' of the vibrational and/or compressive device. This embodiment is denoted as 100' in FIG. 4, and therefore the vibration and/or compression may be applied at a much lower rate than each of the individual motors 30 and 32 vibrate alone. This assembly of plural motors coupled through a backing, chassis, housing, substrate or mechanically capable may be referred to herein as a "coupled motor assembly". In the case of two interacting motors, they may be referred to as a "coupled motor pair assembly". Although the coupled motors are generally discussed herein as a coupled motor pair, using 2 coupled motors, it should be understood that this is exemplary only, and that a larger number of motors may be coupled together and used as described herein.

Figure 5:
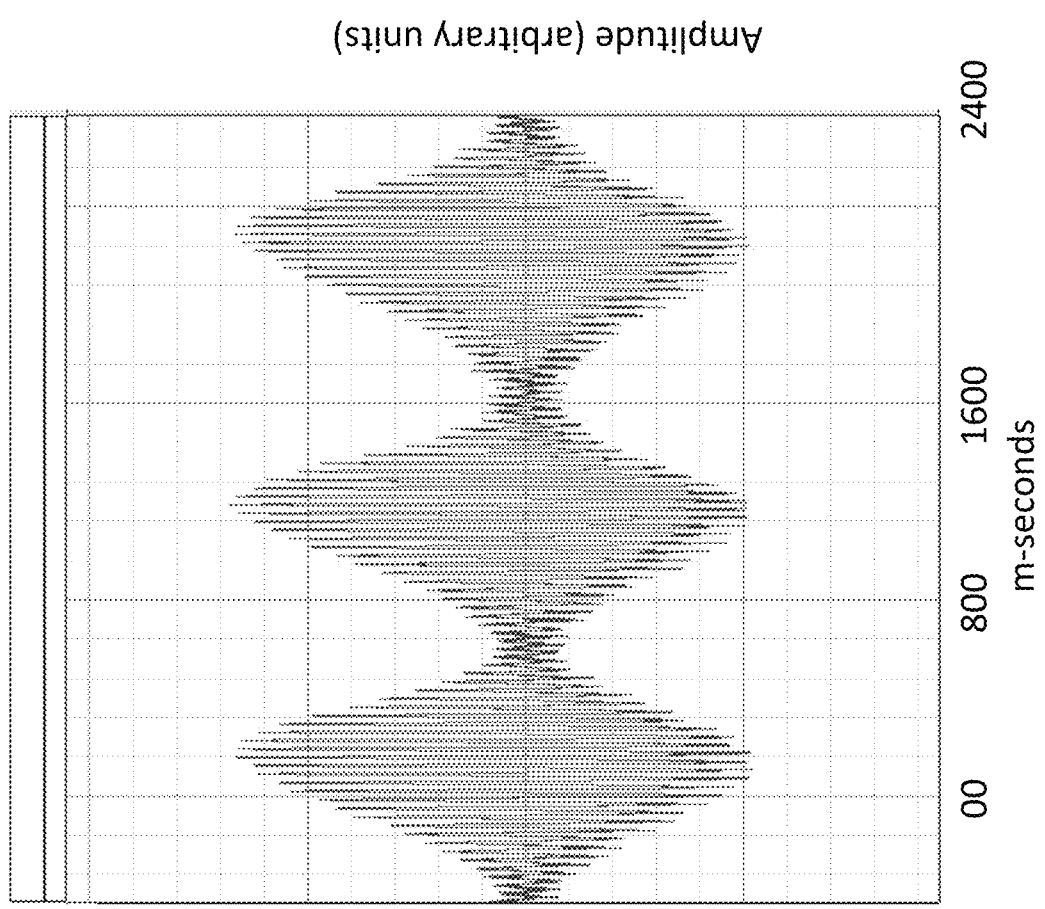
FIG. 5 is a plot showing the beat frequency 80 resulting from the interaction of frequency 1 applied to motor 1 and frequency 2 applied to motor 2.

FIG. 5 is a plot showing the amplitude of the motion of the coupled eccentric rotating mass ERM motor pair 30 and 32 in the vibration/compression device 100', when one motor is driven by one frequency, and the other motor is driven by another. In the data shown in FIG. 5, the difference between the two frequencies is at about 1 Hz. As a result, the beat frequency 80 occurs at about 1 Hz, as shown in the chart a FIG. 5. Among the important advantages of this particular embodiment is that low frequencies can be achieved without the use of a large, low frequency, expensive, massive motor. By using a beat frequency 80 created by two motors at different frequencies, the vibration and/or compression can be generated conveniently, as described more fully below.

One particularly interesting embodiment may be when the first frequency $f_1$ applied to motor 30 is held constant while the second frequency $f_2$ applied to motor 32 is swept through a frequency range using, for example, the sawtooth function of FIG. 3A. In this case, the beat frequency 80 will also be swept through a range that is the difference between $f_1$ and $f_2$. Using this architecture, the beat frequency 80 may conveniently and easily be designed to overlap or nearly overlap with a naturally occurring physiological rhythm, such as heart rate or respiration. It appears that using such an approach, the autonomic nervous system may respond by altering the physiological rhythm to match or approach the beat frequency of the motors. Accordingly, by applying a beat frequency which is near, but slightly lower than the user's resting heart rate, may encourage the resting heart rate to be lowered as a result. Several applications described in the following sections make use of such a concept.

FIGS. 6A and 6B show two additional variations of the vibrational and/or compressive device 100' depicted in FIG. 4. As before in FIG. 4, in FIG. 6A, two motors are shown, motor 30, and motor 32. Two eccentric masses 20, and 22 are once again affixed off-center on two axles 31 and 33. The motors, 30 and 32 are coupled to a backing or housing 10, by a coupling mechanism 50. Accordingly, the vibration or wobble of the two motors 30 and 32, will be transmitted to the backing 10. A beat frequency may arise in the vibration, as described previously.

However, in FIGS. 6A, the two eccentric masses 20 and 22 may rotate in a counter cyclical fashion. That is, eccentric mass 20 may rotate counterclockwise as viewed from above, whereas eccentric mass 22 may rotate clockwise as viewed from above. The rotation of the two momentums 20 and 22 in an opposing sense, may give rise to different behavior compared to the embodiment shown in FIG. 6B.

The embodiment shown in FIG. 6B, again has the two motors 30 and 32 coupled together by the coupling mechanism 50. Affixed to the motors 30 and 32 are the two eccentric masses 20, 22, respectively. However, in the embodiment shown in FIG. 6B, the two eccentric masses 20 and 22 rotate with the same handedness as one another. That is, eccentric mast 20 may rotate counterclockwise, and eccentric mass 22 may also rotate counterclockwise as viewed from above.

The masses 20 and 22 may also rotate with a phase difference or frequency difference between them, or they may rotate in synchronism. These choices, cyclical or counter cyclical, the phase relationship, amplitude and frequency between the eccentric masses 20 and 22, may all affect the behavior of the vibrational and/or compressive device 100'. These design choices may be made, depending on the details of the application, and the behavior desired of the vibrational and/or compressive device 100'.

Figure 7:
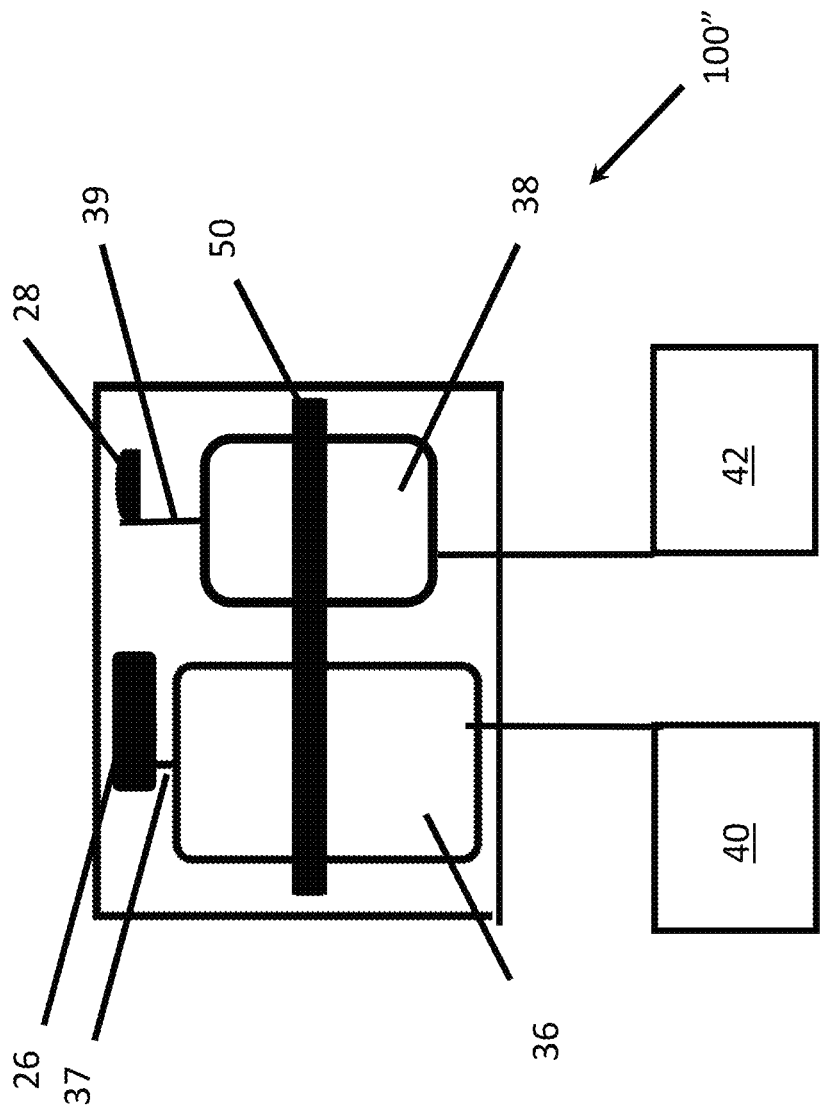
FIG. 7 is an illustration showing design choices with respect to the size of the two motors and the eccentrically rotating masses.

FIG. 7 shows another exemplary embodiment of the vibrational and/or compressive device 100". In this embodiment, once again, two motors may be used, in this case larger motor 36, and smaller motor 38. Attached to each of these motors is an axle, axle 37 attached to motor 36, and axle 39 attached to motor 38. On these two axles are mounted eccentrically mounted masses, both of which are again mounted off the rotational inertia center of the mass. Eccentric mass 26 is coupled to axle 37 which is driven by motor 36. Eccentric mass 28 is coupled by axle 39 and to motor 38.

However, in that case shown in FIG. 7, the two eccentric masses 26 and 28 may not be identical as they were previous embodiments. In the embodiment shown in FIG. 7, the larger motor 30 may have a larger eccentric mass 26 affixed to its axle, whereas the smaller motor 32 may have a smaller eccentric mass 28 coupled to its axle. Of course, the converse may also be used, the smaller mass 28 on the larger motor 30, and the larger mass 26 on the smaller motor 32. The shapes may also be different as illustrated qualitatively in FIG. 7.

Accordingly, as shown in FIG. 7, the components of the vibrational and/or compressive devices may not be identical. Some may be larger than others, the shapes may be different. Each of these design choices may affect the details of the vibration produced, and thus may be made depending on the requirements of the application and the behavior characteristics required of the devices.

Figure 8:
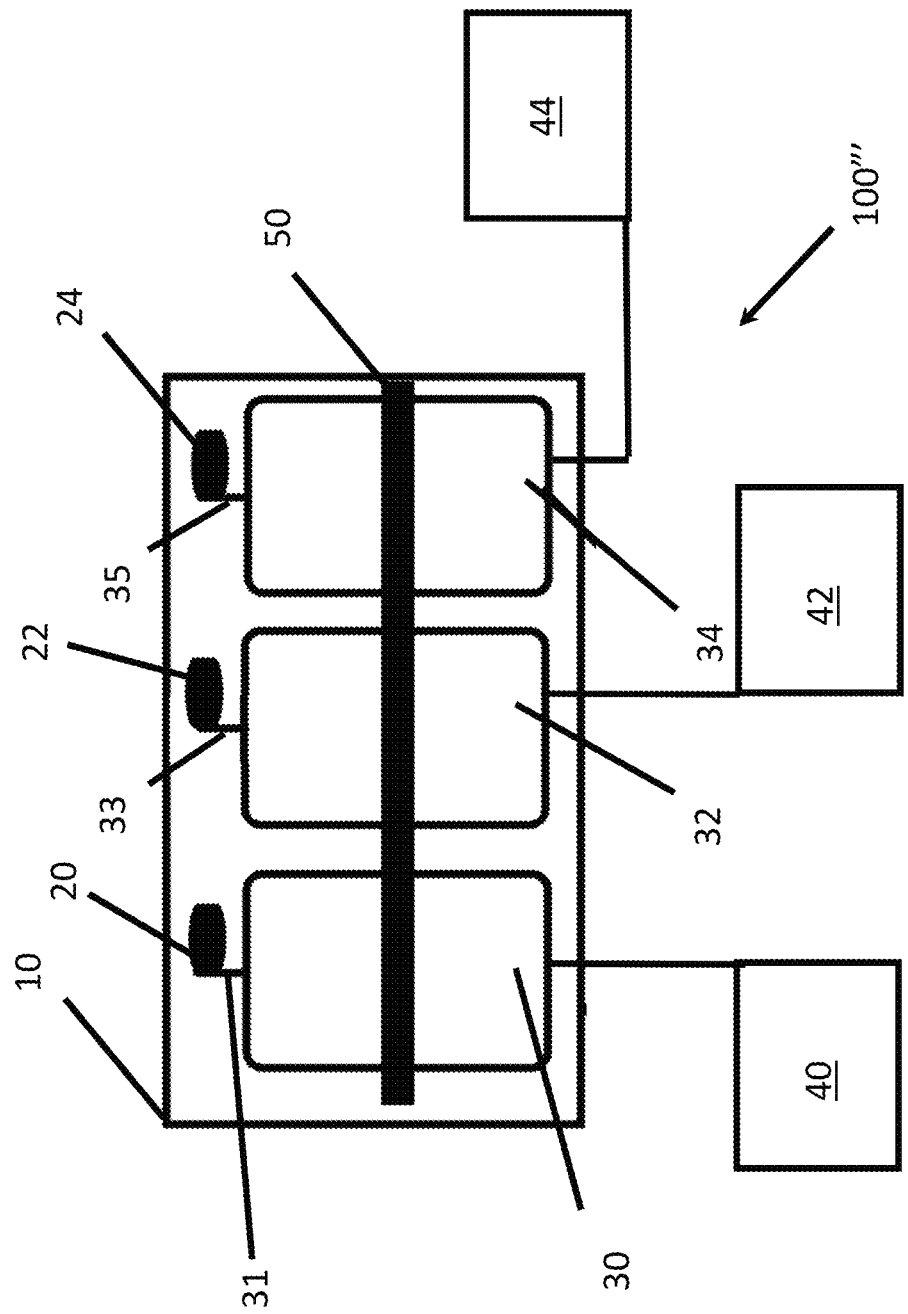
FIG. 8 is an illustration showing a vibrational and/or compressive device using three motors and three eccentrically rotating masses.

FIG. 8 is another schematic illustration of another exemplary embodiment 100'''. The embodiment 100''' shown in FIG. 8, uses three motors 30, 32 and 34. Attached to these three motors are three axle shafts, 31, 33, 35. On each axle shaft, 31, 33 and 35 an eccentric mass 20, 22 and 24 is mounted off center. Each of motors 30, 32 and 34 are driven by a controller, 40, 42 and 44 respectively. The three motors 30, 32 and 34 will be coupled by a coupling mechanism 50 which couples them to the backing, chassis or housing 10. This coupling mechanism 50 transmits the vibration of the motors to the backing, chassis or housing. 10, and thus on to the user.

As before, each of the motors 30, 32 and 34 may be driven at a different frequency, amplitude, and phase relationship. They may have different masses and may rotate in the same sense or in opposing senses. In short, each of the variations discussed with respect to the 2-motor embodiment 100' may also be available in the three motor embodiment 100". The components may be identical, or they may be different, or there may be a combination thereof. The motors may be all coupled together, or they may couple together in pairs, or they may be coupled individually to a backing, housing or chassis 10. Accordingly, a wide variety of rather complex motions may arise with these vibrational and/or compressive devices as described.

It should be understood that the design concepts discussed here may also be applied to a vibrational and/or compressive device with any other number of motors, rather than one, two or three. As the vibrational and/or compressive device becomes more complex, more complex behaviors may be expressed by them, such that the details can become exceedingly complex. Common to all of the embodiments, however, is an axle rotating with an unbalanced mass, which imparts a wobble or vibration to the rotation of the motor.

As illustrated by FIGS. 6-8, the vibrational and/or compressive device may have a single motor, it may have two motors, it may have three motors, it may have any of a number of motors all rotating at once. There may be a phase relationship between each of these motors, they may or may not have identical masses coupled to them. The masses may or may not be rotating in a counter cyclical manner. The frequency delivered to each of these motors may also be different, and may be changing in time.

The mass may be smooth and symmetric, or it may have a complex shape. Accordingly, the masses maybe elliptical, however that is not necessarily the case. However, in all cases the rotation of the masses causes a force which acts on the motor. While one way to accomplish this is with off-center shape, another example would be two off-center shapes 180 degrees opposed at different axial positions along a motor shaft. When spun, such a geometry would drive an oscillatory rotation of the shaft (wobble) perpendicular to the long axis.

A sensing mechanism or accelerometer may also be provided for the embodiments shown in FIGS. 1-8, although the accelerometer sensor may not be necessary.

Coupled Wobbling Motors in a Case

As described below, the backing, housing or chassis may be a case which encloses and protects the vibration devices 100, 100', 100" or 100'''. The embodiments described below may contain one or more eccentric rotating mass motors 30 in a single case. In embodiments, the collective action of the motors may move the entire case. This makes it possible to generate large amounts of acceleration in a relatively low profile case. The case may be a stamped or injection molded plastic, or other material chosen to be capable of protecting the moving parts from damage. The case may then be attached to a platform as described below.

The motors may be driven by a PWM signal. An identical signal can be sent to each motor. In another embodiment, different signals can be sent to different motors to bring about different resonant modes in the casing.

Each eccentric rotating mass motor may have a specific resonate response to the rotating mass on its respective shaft. Coupling multiple motors together mechanically using the housing, also couples the motor's resonant response.

Referring again to FIG. 4, the figure shows an example embodiment in which motors may be coupled through a solid substrate all enclosed in a case, with an accelerometer attached to the substrate to measure the movement of the assembly. In this situation, the motors may be driven in the opposite direction. In embodiments, we describe a device that may have 2 or more eccentric rotating mass vibration motors in a single case. The case may act as a substrate to couple the motors together mechanically. The motors may be driven at a specific drive voltage using a PWM signal. By driving the two motors independently they can be driven at voltages or PWM values. Depending on the supplied signal the individual motors will spin at a certain frequency. Through the case, the vibrations of the motors are coupled. By driving the 2 motors at specific frequencies a secondary resonant modes develop through the coupled assembly.

In some embodiments the motors may be driven in opposite directions, as described above.

FIG. 5 depicted an acceleration plot of an embodiment having a housing or case with two motors operating at nearly the same frequency. The difference is seen in the sum and difference resonant mode of the entire housing. The Secondary Wave Frequency=1 Hz=60 beats per minute. In embodiments, the device may determine the resonance of the coupled motors by reading the PWM signal. The mechanical resonance of the motors couples to the PWM signal. This method of reading the mechanical resonance of reading the two motors can replace the need for an accelerometer.

In another embodiment, the motors are coupled through the user's body as was shown schematically in FIG. 1C. In one embodiment this coupling is through the finger with either motor on either side of the finger. In another embodiment the motors are coupled through the wrist with a motor on either side of the wrist. In this fashion, the motors inject mechanical energy into the body by creating a secondary harmonic vibration in the body.

In embodiments, by creating a secondary harmonic slower than the heartbeat of the user, the device may calm the user by slowing their heartbeat. In embodiments increasing the secondary harmonic above the frequency of the heartbeat may serve to elevate the user's heartbeat, increasing their arousal state.

In one embodiment the motors may be driven to counter rotate to increase the coupling of the motors to produce the secondary harmonic oscillation. Driving the motors separately at nearly the same PWM signal may produce distinct secondary harmonics. By varying the relative and absolute PWM signals sent to the motors, different secondary harmonic frequencies can be produced.

In one embodiment, two motors are coupled through a rigid body. One of the motors is established as the master and the other is the slave. The master motor is driven at a specific PWM signal or voltage to create a desired frequency of vibration. The slave motor is then driven using a separate PWM or voltage. Using an accelerometer the vibrations of the entire system is detected. The slave drive PWM signal or voltage is then adjusted to create the desired secondary harmonic or beat mode vibration.

In another embodiment, detection is performed by measuring the PWM signals to the motors. When the motors resonate with each other the mechanical coupling induces a voltage back into the signal at the frequency of the secondary harmonic. By monitoring the PWM signal or voltage it is then possible to determine which motors are in a coupled resonance.

In one embodiment, the geometry of the mechanical coupling, the case of the two motors, is adjusted to tune the nature of the secondary harmonic. In one embodiment the case holding the motors is designed so that it may be influenced by the user's own body. The case allows for the coupling with the user to influence the mechanical resonance properties. In one embodiment the user is used as the substrate for coupling of the motors so that a user can sense the secondary harmonic of the two motors. In one embodiment the motors rotate in the same direction. In another embodiment, the motors rotate in the opposite direction. In one embodiment, the motors are parallel to each other with the eccentric mass on the same side of the axle. In another embodiment, the eccentric masses are on opposite sides of the axle. In one embodiment the motors are placed inline end to end with eccentric masses facing out. In another embodiment, the eccentric masses are facing in. In one embodiment the device is worn on one wrist. In one embodiment the device is worn on two wrists.

In one embodiment the device is two pairs of coupled motors worn on opposite sides of the body. When the two sets of coupled motors are driven at a specific PWM or voltage a similar secondary harmonic is established in both sets of coupled motors. The bilateral oscillation has been shown to help treat trauma, PTSD and other ailments. By inducing the secondary harmonic in addition to the bilateral oscillations the effect on the user is greatly improved. In some embodiments a bilateral stimulation device may use secondary harmonics of mechanically coupled oscillators. Any device that is using vibrations to affect a user may be greatly improved by the devices, components, systems, and/or methods disclosed herein.

In one embodiment the two motors are wired in parallel with the same drive PWM or voltage signal. In one embodiment the two motors are wired in series. In one embodiment the two motors are wired in parallel with the same drive signal, but with one of the motors having a variable resistor slightly altering the drive signal. In one embodiment the human body acts as the coupling mechanism between two or more motors. This creates a secondary lower frequency wave FIGS. 5 and 80 through the addition and subtraction of the primary drive frequency 85 of the two motors.

As described previously, in each of these embodiments, at least one motor is mechanically coupled to a housing, chassis or backing 10. Because of the wobble or vibration of each of the motors, this wobble or vibration is transmitted to the backing, chassis, or housing 10. Together, the motor, axle, eccentric mass, and backing comprise the vibrational and/or compressive device 100, 100', 100" or 100'''. A plurality of similar vibrational and/or compressive devices 100, 100', 100" or 100''' and/or other embodiments not described here, or a combination thereof, may be used on a common delivery platform, in order to transmit the vibration in a therapeutic manner to the user.

The remainder of this disclosure describes the various ways in which these vibrational and/or compressive devices can be arranged, driven, and controlled, in order to provide a therapeutic vibration and/or compression to patient or user.

Each platform or architecture may be described with respect to a vibration and/or compression device 100. However it should be understood that the platform may also make use of vibration and/or compression device 100', 100" or 100''' or a vibration/compression device not described here, or a combination thereof. Accordingly, common to all of the embodiments, platforms and architectures is an axle rotating with an unbalanced mass, which imports a wobble or vibration to the rotation of the motor.

Motors, Electronics and Other Supporting Hardware

In embodiments, there may be provided 12 VDC vibrating brushed or brushless DC motors' having rotational rates controlled by a Pulse Width Modulation (PWM) drive voltage transmitted through the cable harness to the motors. The motors may operate in a rotational rate range of 5-500 Hz. The amplitude of the motor's mechanical vibration varies with the PWM drive voltage.

In embodiments, there may be provided a microcontroller adapted and configured to send motor control signals to a PWM control board. The PWM control board then sends the PWM drive signals to the DC motor controllers, which then send the PWM drive voltages to the DC motors.

The PWM drive signals may be set to a specific fundamental frequency somewhere between 10 Hz and 30 kHz. The specific fundamental frequency is chosen on the basis of type of DC vibration motor used, where the optimal fundamental frequency may be a function of the size, weight, coil resistance, and nominal rotational rate of the motor. The fundamental frequency may be chosen to optimize motor efficiency in terms of electrical power in versus mechanical power out.

Frequent use is made herein of the term "algorithm". As used herein, an algorithm may be a computer program that adjusts a sequence of vibrations. The sequence of vibrations result from the application of a motor drive waveform to the wobbling motors, as described in considerable detail below. The sequence of vibrations may increase and/or decrease the frequency and amplitude in a regular periodic fashion with a characteristic wavelength. One algorithm increases or decreases the wavelength depending on the periodic rate from the sensor. For heart rate variability (HRV) discussed below, and respiration the period of the generated vibration wavelength will be just a be slightly longer so as to increase the period length of respiration and HRV.

Detection

The human body acts as a resonant cavity when actuated by a vibrating mass. In embodiments, by performing a frequency sweep of the vibrating motors, resonances of the body can be determined. To obtain these resonant frequencies, a system composed of the vibration motors and a detection accelerometer may be used. The vibration motors act as an input, transferring mechanical vibrations to the body. In embodiments, there may be provided accelerometers placed at various positions in the vest to detect vibrations of the body. By mapping the input voltage to the motors to the frequency response of the body determined by the accelerometers, the resonance of the body may be determined. This resonant information can then be used in the motor routine to increase the effect of the vibrating motors on the body.

In embodiments, another detection modality uses a microphone. The user makes sounds with their voice while the motors perform a frequency sweep. As the human body resonates, there will be greater distortion of the voice. This distortion may be mapped to input signals to determine the corresponding frequency response of the motors on the human body.

The first delivery platform that will be described is that of a wearable garment 101 fitted to the body, shown in FIG. 9. The first example is a garment fitted to the torso, e.g., a vest 101. The vest 101 may be snugly fit to a patient using a configurable or adjustable fitting mechanism 103. The fitting mechanism 103 may be, for example, snaps, Velcro, buckles, belts, laces that may draw the garment up like a corset. The fitting mechanism 103 serves to hold the plurality of vibration and/or compression devices 100 firmly against the body of the user.

Figure 9:
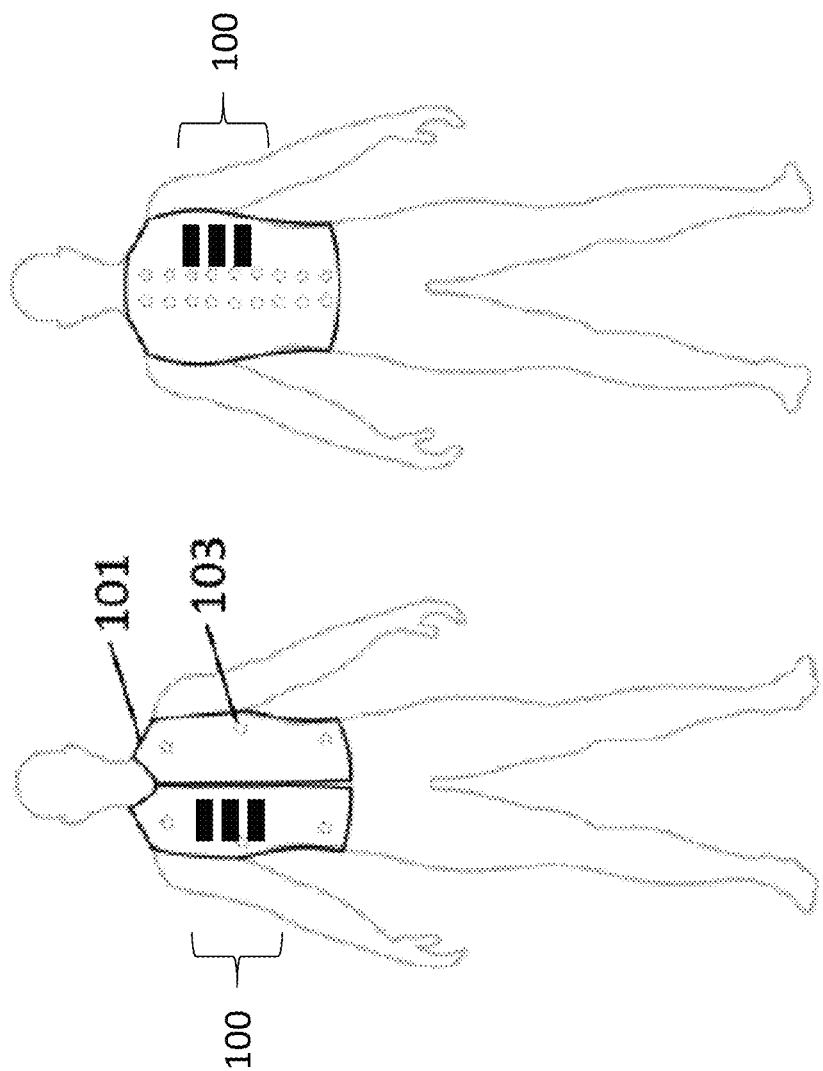
FIG. 9 shows the implementation of the eccentric motors on a vest garment worn on the torso.

The vest embodiment 101 shown in FIG. 9 may have three vibrational and/or compressive devices 100, disposed on the right hand side of the torso of the user (shown front facing in FIG. 9). Three additional vibrational and/or compressive devices 100 may be located on the back portion of vest 101, also on the right hand side of the user. It should be understood that this is an exemplary embodiment only, and then more or fewer vibrational and/or compressive devices 100 may be disposed on the vest embodiment 101. In addition, the vibrational and/or compressive devices 100 may be disposed in any of a number of different locations on the wearer's torso. These may be locations that are chosen because they are particularly effective at accomplishing a therapeutic purposes, as will be described further below.

This vest 101 may be exemplary of garments in general, which may also take the form of a pant leg, a sock, a hat, earring or headband for example. The vest embodiment 101 is merely exemplary of a wearable garment in general, as distinct from other delivery platforms described below. It should be understood that the vibrational and/or compressive device 100 can be incorporated in many different delivery platforms for delivery of the therapeutic vibration and/or compression to a user. Several of these delivery platforms are illustrated in FIGS. 10A-10D.

FIGS. 10A-10D show four other delivery platforms on which the vibrational and/or compressive device 100 may be deployed. FIG. 10A shows a chair 12, wherein vibrational and/or compressive devices 100 are installed behind the fabric of the chair. In addition, additional vibrational and/or compressive devices 100 may be deployed in the seat portion of the chair, or in the arm rest portions of the chair, as shown. The location and distribution of the vibrational and/or compressive devices may be optimized to achieve a therapeutic purpose.

FIG. 10B shows a sleeping or horizontal delivery platform 14, whereon the user can recline in order to receive the vibrational and/or compressive therapeutic massage. In FIG. 10B, the vibrational and/or compressive devices 100 are shown distributed on a front surface of the mattress or delivery platform.

FIG. 10C shows a sitting cushion 16, where in a plurality of vibrational and/or compressive devices 100 is also deployed. This configuration may be particularly effective in coupling the vibrations in a resonant fashion to a user's torso or spinal column.

FIG. 10D shows a pendant earring 18, wherein a vibrational and/or compressive device 100 is also deployed, and suspended from the earlobe.

Also contemplated is a headband, wristband, shoe insert, for example. This list is not meant to be exhaustive, but only exemplary in the modes in which the vibrational and/or compressive device 100 can be deployed to provide therapeutic vibration and/or compression to a user.

In one embodiment the device includes a compression vest. In another embodiment the device includes a complete suit. In another embodiment the device includes a pair of shorts. In another embodiment the device includes a pair of pants. In one embodiment this includes a blanket. In one embodiment this includes a cape. In one embodiment this includes a poncho. In one embodiment the device includes a pair of boots or shoes. In one embodiment the device includes a pair of gloves. In another embodiment the device includes a sheet of fabric with haptic transducers distributed throughout. In one embodiment the device is integrated into a theater chair creating a coordinated response to the audio and video in the film or theater being viewed.

A wearable support, such as, for example, a vest, may have a plurality of eccentric rotational mass vibration motors. The size of the motors may vary. Each motor may display a different response to an applied signal such as but not limited to, a PWM voltage signal. The motors may be characterized by performing a sweep of the input signal from zero to 100% and then back down to zero. In embodiments, attached to the motor is an accelerometer measuring the physical acceleration of the motors.

Other Garments or Modalities

Other garments or methods can be used to secure the compression devices to the user. In one embodiment there is provided a pair of stretchy shorts with the compression devices built in. These shorts may have straps to help secure them. These shorts may have integrated hook and loop fastener straps to help secure the shorts. In one embodiment the device may include a full body suit. In one embodiment the device may include sleeves for the arms. In one embodiment the device may be adapted for the feet. In one embodiment the device may be adapted for the hands.

It should be understood that the arrangement and number of compressor devices used is a design choice which may be made, depending on the application, the function, and the purpose of the therapeutic device Our experiments have shown that certain people have an itchy response to the vibrations. To mitigate this the device has a buffer layer placed between the motors and the user. In one embodiment the device has a thick interface material that sits between the user and the motors. In one embodiment this is a layer of neoprene 0.5 mm to 3 mm thick. The material reduces the amount of lateral displacement on the skin.

In one embodiment this layer is a continuous layer inside the vest. In one embodiment this is a continuous layer of material lining the garment residing between the user and the device.

The interface material provides a stiff medium along an axis parallel to the body. By forming a continuous layer of material limits the amount of lateral movement of the device relative to the skin. This may help reduce itching.

Mechanical Coupling of Motors

Figure 21:
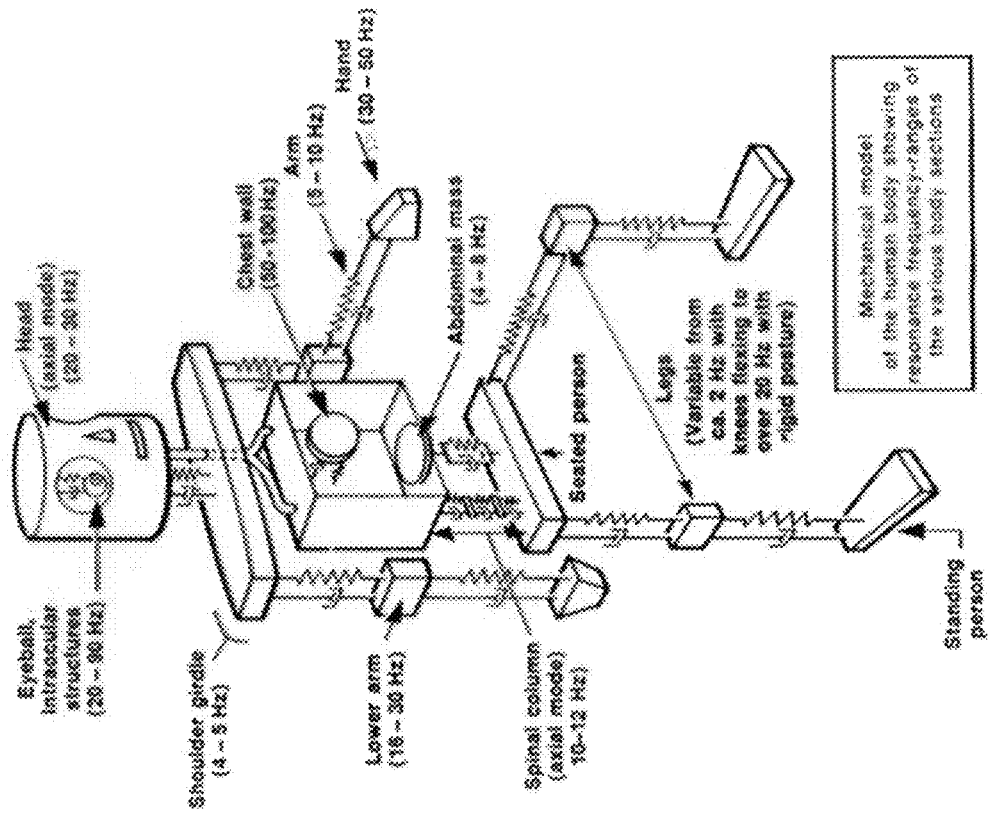
FIG. 21 shows approximate resonant frequencies for different parts of the body.

In another embodiment the system FIG. 20A can be represented as a spring-mass-damper system. The spinning of the eccentric rotating mass creates oscillations in the vertical axis. By placing device 100, 100' or 100" on a cushion, padded seat, or other surface that can be represented as a spring mass damper, a resonance will occur that is mechanically coupled into the user FIG. 20B. The human body resonates at various frequencies, represented in FIG. 21. As illustrated by FIG. 21, there are various resonances in the human body. For example, the eyeballs may have a resonance at 20-90 Hz, the head axial mode at 20-30 Hz, shoulder girdle at 4-5 Hz, chest wall at 50-100 Hz, arm at 5-11 Hz, hand at 30-50 Hz, lower arm 16-30 Hz, spine 10-12 Ha, abdominal mass 4-8 Hz, and legs at 2-20 Hz, depending on the body position. The structures illustrated in FIG. 21 are examples of naturally occurring mammalian resonant structures, which may resonate with the naturally occurring mammalian physiological rhythm. When the vibration producing motor is disposed on or near such a structure, the combination may form a resonant coupled system.

In some embodiments, two motors may define a motor pair that may be disposed so as to span the centerline of the body of the user. That is, the motors of a motor pair may be located adjacent to one another, with one motor of the pair on one side of a centerline of the body and the other motor on the other side of the centerline of the body. A plurality of such placed motor pairs may each generate a beat mode frequency. The coupling between the motors of the motor pair may take place through the body of the user, to therapeutic effect. The inside edges of adjacent ones of the plurality of motor pair assemblies may be spaced between 0.25 inches and 7 inches apart from each other.

Figure 22:
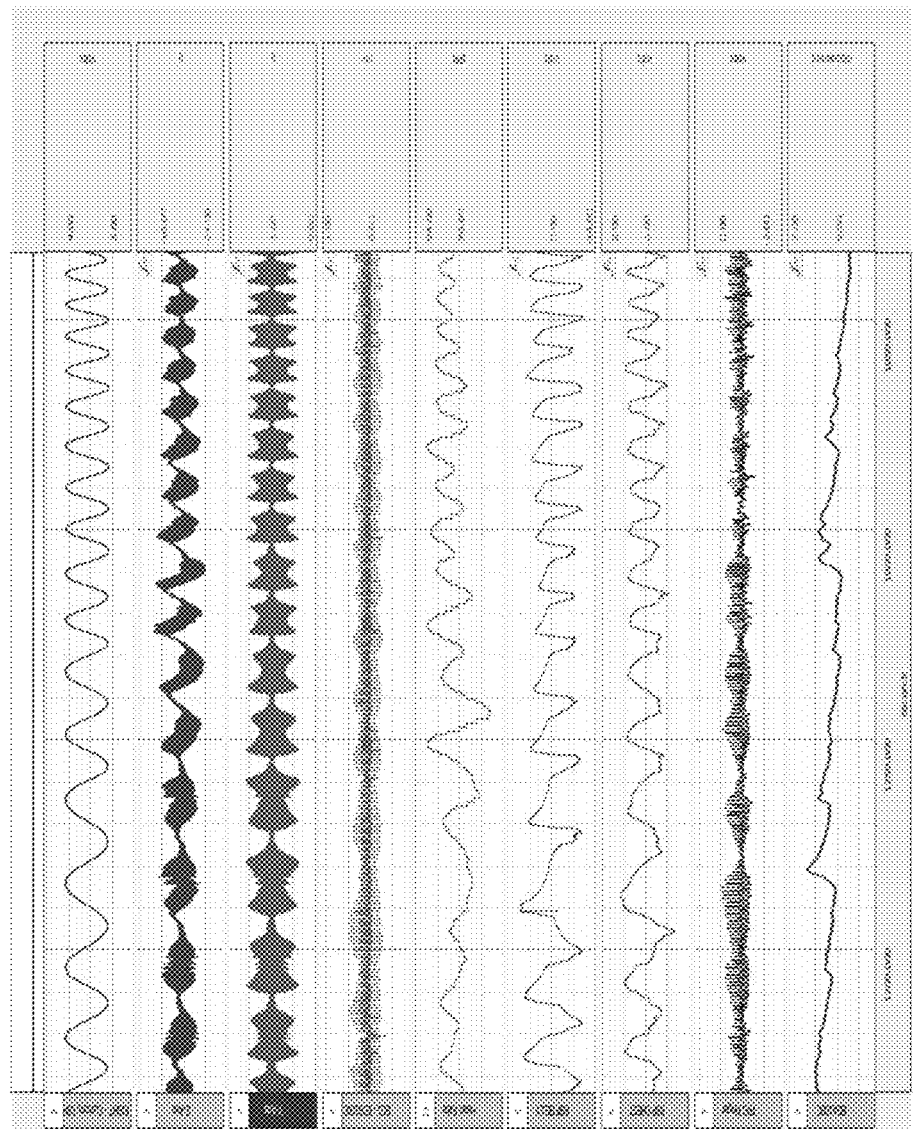
FIG. 22 shows example biometric data as a user is being stimulated by the device.

By matching these frequencies it is possible to create mechanical oscillations throughout the body. These mechanical oscillations in the human body are then coupled to other systems, such as the skeletal, respiratory, circulatory, nervous, lymphatic, and endocrine systems. An example is shown in FIG. 20C of how the spine can also be represented as a spring-mass-damper system. Oscillations of device 100' in this example create movement through the spine and cause the head to move up and down. Sweeping through a frequency range couples to resonant frequencies throughout the body. FIG. 22 shows experimental data for the system in FIG. 20B. FIG. 22 shows that the mechanical oscillations created by device 100' create mechanical pulses that can be detected in the head of the user as evident in waveforms 3 and 9 in FIG. 22 which represent accelerometer data from device 100' and the forehead of a user respectively.

The mechanical oscillations of the body affect other systems. In FIG. 22 it can be seen that the sinusoidal pulses from device 100' transfer mechanically through the body and affect other systems. Waveform 4 in FIG. 22 shows the R-wave amplitude of the ECG increasing and decreasing in sync with the mechanical vibration from device 100'. Waveforms 5 and 6 in FIG. 22 show the respiration pattern of the user in sync with the mechanical vibration from device 100'. Waveform 7 in FIG. 22 shows the photoplethysmograph of a user's fingertip increasing and decreasing in sync with the mechanical vibration from device 100 indicating that the circulatory system is coupled to the mechanical oscillations.

System Architectures

FIGS. 11-15 show system architectures which make use of the vibrational and/or compressive device 100. These system architectures may employ other components as described below, in order to accomplish a therapeutic purpose or provide a specific behavior of the vibrational and/or compressive device.

Figure 11:
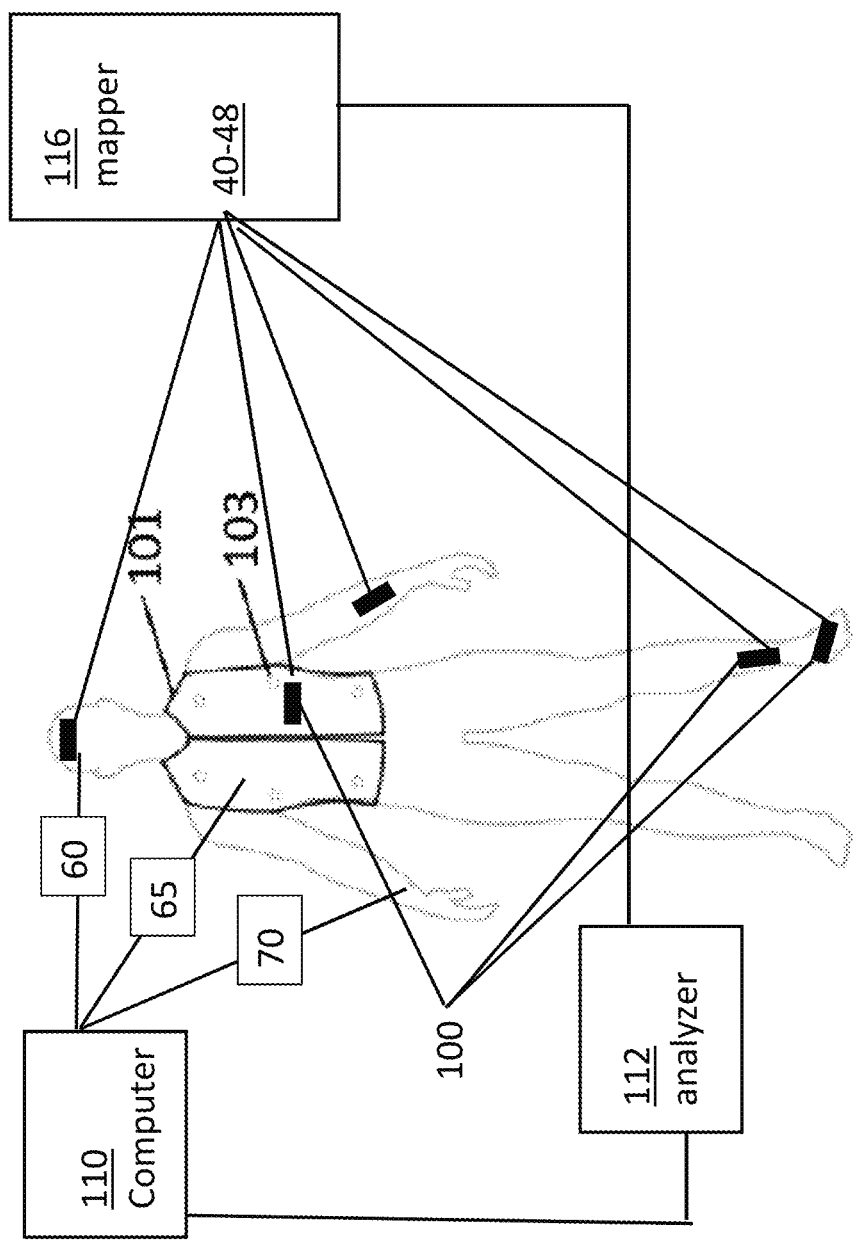
FIG. 11 is a simplified schematic diagram of the different components in a system architecture using the vibrational and/or compressive devices with at least one biometric sensor.

In the system shown in FIG. 11, a number of sensors 60, 65 and 70 are applied to the body. The sensors may be located wherever a piece of bioinformation can be acquired by the sensors, but in some embodiments, they may be located, for example, on or near the head, chest and wrist as shown by sensors 60, 65 and 70 in FIG. 11. It should be understood that this is exemplary only and that the sensors may be deployed in different quantities, and in a large number of different areas, such as the chest, on the head, in the ear canal, or on the neck. The sensors 60, 65 and 70 may be positioned externally, internally or remotely. However, the sensors are configured to measure some piece of bioinformation, wherein the bioinformation is generally related to the user's status or condition.

The biometric sensing equipment that measures the item of bioinformation may be involved in this system in a feedback loop, as will be described further below. Alternatively, the bioinformation may be fed to a decision making unit, which may adjust the motor controller in response to a certain behavior as measured by the sensing unit. This unit is also referred to as a "mapping unit" because it may map one item (sensor signal level) to another item (algorithm applied to the motor). The decision making unit could also use artificial intelligence.

Numerous biometric quantities (bioinformation) can be monitored, and they may include Heart Rate (HR), Electrodermal Activity (EDA), and Heart Rate Variability (HRV). However, other biological aspects may be measured, including blood pressure, respiration rate, eye blinking and oxygenation. Other aspects may include respiratory effort, electroencephalography (EEG), piloerector muscle activity, electrogastrography (EGG), reaction time, electrooculography (EOG), pupil diameter, micro/macro saccade activity, posture, skin potential, electromyography (EMG), pre-ejection period (PEP), stroke volume (SV), cardiac output (CO), left ventricular ejection time (LVET), blood pressure (BP) and vascular resistance, for example. This list is not meant to be exhaustive, but only to provide examples of bioinformation that can be used with the vibrational devices. The terms used here are standard terms familiar to anyone skilled in the art.

The output of the sensors 60, 65 and 70 may be fed to a computer, 110, that receives the sensor signals and records them.

After the computer 110 receives the sensory output, it may feed the signal to an analyzer 112. This analyzer may analyze the signal in order to characterize the state of the user wearing the therapeutic vest 101.

When the analyzer has completed its analysis of the signals from computer 110, it may send a signal to a mapper 116 shown in FIG. 11. This mapper may map the analyzed sensor results to a specific algorithm that is then applied to the motor 30 by the motor controller 40. Several examples of this mapping algorithm are described further below in the section directed to applications.

Another intrinsic function of the mapper 116 may be to compare the sensor output value to a pre-defined target value for that piece of bioinformation. Accordingly, the mapper may include a comparator. Accordingly both the mapper and comparator may be illustrated schematically by the functional component 116. It should also be understood that all of these functions may be a dedicated piece of electronic hardware, or it may also be carried out by the controller or computer 110, which has been programmed to execute these functions. Accordingly, although these elements are shown as separate components, they may separate components or they may be executed by the controller or computer 110. In one embodiment a user's pulse rate is monitored by a sensor deployed on the wrist, and the sensory output is recorded by computer 110. This data, possibly in combination with other data such as blood pressure, respiration, perspiration, may also be sent to the computer 110. The data collected by computer 110 from the sensors deployed on the user may then be sent to the analyzer 112. The analyzer 112 may analyze the data, in order to characterize, for example, the level of relaxation or arousal that the user is presently experiencing. For example, if the analyzer 112 determines that the user is in a stressed or hypertensive state, the analyzer may send the message to the mapper 116 directly to apply a stress lowering algorithm to motor controllers 40-48. The stress lowering algorithm may include vibration and/or compression pulses that are substantially synchronous with the heart rate but slightly lower. This may urge the autonomic nervous system to relax the breathing, blood pressure or pulse rate. Other examples of stress lowering algorithms are described below with respect to other implementations and embodiments.

In the general flow, the algorithms may be fed to the motor controllers 40-18, which will control the motor movements according to the applied algorithms. Thus, the motors in the vibrational and/or compressive devices will execute what may, in fact, be a rather complicated sequence of vibrations, in terms of frequency, phase and amplitude changes.

In some embodiments of this system architecture, after the algorithm is provided to the motor controller and in use by the motor, another sensing cycle may be undertaken. That is, controller 110 may poll the sensors 60, 65 and 70 again, in order to detect the effect of the vibrational and/or compressive device on the user. For example, the user may be a patient with high levels of stress, as evidenced by an elevated heart rate. A heart rate monitor may measure the user's heart rate, feed that to the controller and/or signal analyzer, which determines that the user's heart rate is higher than the target heart rate. A signal may be sent to the mapper 116 which may invoke a heart rate reducing algorithm. After a period, the sensor may be polled again, to see if the stress level is reduced as represented by the sensor output. If not, a different algorithm may be invoked, or a signal level changed.

It should be appreciated that the number and placement of these vibrational and/or compressive devices 100 in architecture shown in FIG. 11 are exemplary only and that other configurations may also be chosen. It should also be understood that the methods described here may equally be applied to other platforms, such as those shown in FIG. 10A-10C. It should also be understood that the functions of the signal analyzer 112 and mapper 116 functions may also be performed by a single computer, 110, such that separate functional units may not be necessary. All of the functions described here, including the signal analyzer and mapper, may not be necessary in all architectures, and in some, the function may be absent entirely.

In some embodiments, a feedback loop may be involved, in which the behavior of the vibrational and/or compressive devices is changed based on a sensor 60, 65 and 70 reading. After implementation of the algorithm, the sensors 60, 65 and 70 may be monitored to ascertain the effect of the algorithm on the sensed quantity.

However, in other embodiments, there may be no feedback loop, but the sensor output is simply applied to the mapper or decision making unit 116, which selects an algorithm to apply to the motor controller 40. Alternatively, the sensor value may be supplied to the user, who may then directly choose an algorithm to be applied to the vibrational and/or compressive devices 100. A simple example would be the sensor output applied directly to an amplifier driving the compression device, with or without a filter to smooth the signal and modify the phase of the compression device output.

It should be understood that not all of the components shown in FIG. 11 may be required in a given system architecture or application. It may be possible, for example, to send the output of the heart rate monitor directly to the mapping unit 116, which then chooses an algorithm to apply to the motor 30 via the motor controller 40.

It would also be understood that the modules shown in FIG. 11 may be implemented in software alone. That is, a single computer 110 may monitor the heart rate, compare its value to a target value, look up the appropriate vibrational and/or compressive device algorithm, and apply it to the motor controller.

There are many examples of possible motor algorithms, only a few of which were illustrated in FIG. 3A-3C. These motor control algorithms can be applied to individual motors, or to banks of motors, or to all motors. They may have a simple oscillatory waveform or an arbitrarily complex and time-varying waveform. The amplitude and frequencies applied may vary in order to transmit information or a particular sensation to the user. One example would be a control algorithm that applies a waveform to a motor and then to the neighboring motor with a time delay, and again to the next motor in sequence, which could provide the effect of a wave going past the subject.

Figure 12:
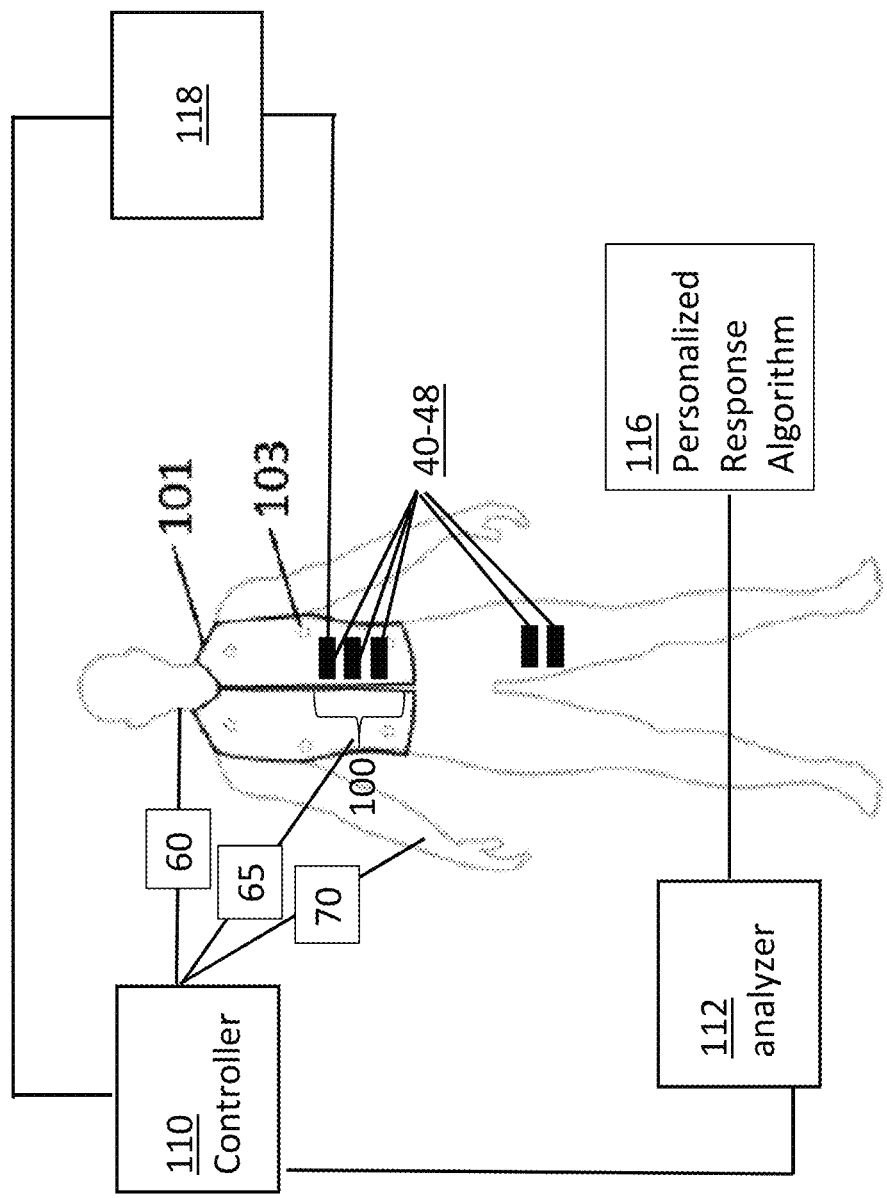
FIG. 12 is a simplified schematic diagram of the different components in a system architecture using the vibrational and/or compressive devices with the at least one sensor and an auxiliary control component.

FIG. 12 illustrates another architecture, wherein the vibrational and/or compressive devices are disposed not only in the vest 101 but also on the thigh and the knee, for example. These are areas in which athletes in particular are prone to soreness and injury. The garment, in this case, may comprise a tight fitting pant in addition to the vest 101.

In the architecture of FIG. 12, in addition to the sensors, controller 110, analyzer 112, and mapper 116, there may be another additional system 118 may be coupled to the garment 101. This system 118 may apply a cooling capability or heating capability to the user. Heat is considered to be a soothing effect, such that warming the torso may assist in the stress reduction outcome of this architecture. System 118 may also be a pneumatic system which may apply air pressure to the vest 101 in order to modify the vibration and/or compression characteristics. Module 118 may also be a cooling apparatus. Applying colder temperatures is known to have a therapeutic effect, and may be particularly therapeutic in combination with massage therapy to mitigate damage or injury to soft tissues.

The apparatus 118 may alternatively provide an acoustic medium such as a gel to the vest. The gel may serve to transmit the vibrations more effectively throughout the garment and especially to areas of the body not directly adjacent to a vibration and/or compression device 100.

FIG. 13 shows further additional architectures making use of the vibrational and/or compressive devices 100. As before, a plurality of vibrational and/or compressive devices 100 are shown disposed in a wearable garment 101. It should be appreciated that the number and placement of these vibrational and/or compressive devices 100 are exemplary only and that other configurations may also be chosen. It should also be understood that the methods described here may equally be applied to other architectures, such as those shown in FIGS. 10A-10D.

The system architectures shown in FIGS. 13A and 13B include a source of a stimulus, either audio 214 or video 210. It should be understood that these architectures may be applicable to stimuli in general, of which audio and video are examples.

FIG. 13 shows an audio stimulus is applied to a user. The audio stimulus may be in the form of music from a speaker 214 as shown in FIG. 13A. The user, of course, will hear the sound from the speaker 214, as one may enjoy listening to their favorite playlist. However, in addition, the signal analyzer 112 may also be analyzing the audio signal, which more generally can be referred to as the input signal. Signal analyzer 112 may be, for example, spectrum analyzer which reports the magnitude of the input signal in certain frequency ranges.

Many relationships between the input signal and the motor response can be envisioned. For example, when the input signal is an audio signal it may be ascertained that applying vibration and/or compression to a user's torso via the vest 101 equipped with multiple compressor devices 100, may enhance the user's enjoyment of that music. This may be particularly true if the bass portion of the audio signal is mapped to the vibration and/or compression behavior of the vibrational and/or compressive device is 100, or when extreme treble notes are present in the music.

FIG. 13B is a schematic illustration of a similar architecture to that shown in FIG. 13A, however in FIG. 13B the stimulus is visual, rather than auditory. In FIG. 13B, a user is displayed a video on a monitor 210. This input signal may be seen by the user, but also monitored by a camera, or simply monitored by tapping off the video signal driving the monitor 210. This video signal is analyzed by a signal analyzer 112, and the output of that signal analysis is fed to the decision maker, or mapper 116. Accordingly, in this embodiment as in the previous one, the user will experience, in a tactile, physiological way the visual images that he is seeing through his own eyes. This may make the experience of enjoying video more powerful, more enjoyable, and more entertaining, than otherwise would be.

The embodiments shown in FIGS. 13A and 13B both make use of a so-called mapping algorithm unit 116. This unit may be something like a look-up table, in that for a given output from the signal analyzer 112, the mapping algorithm unit chooses an algorithm among many. That is, it chooses the proper response to the results of the signal analyzer 112. Alternatively, the mapper 116 may execute a far more complex routine based on the signal analyzer 112 results. For example, a mapping algorithm 116 may be programmed to create large perceptible massaging movement that is correlated to the overall volume of an audio signal. The mapping algorithm would implement that algorithm as a result of the volume measurement from signal analyzer 112. If the volume is higher, the mapping algorithm 116 may choose a higher revolution rate on the eccentric masses of the motor, so by speeding up the massaging rate of the vest 101. In this scenario, the mapping algorithm maps the volume of an audio signal to an RPM rate of the motor. This mapping concept will also be used in FIGS. 14 and 15 where an audio, or video signal is mapped from an intensity profile into a mapping algorithm. In this scenario, the user may perceive the input signal, in this case the video visual or audio signal not through the eyes or cars, but rather through the vest. This may have important applications in a wide range of situations, as will be described further below with respect to FIGS. 14 and 15.

Figure 14:
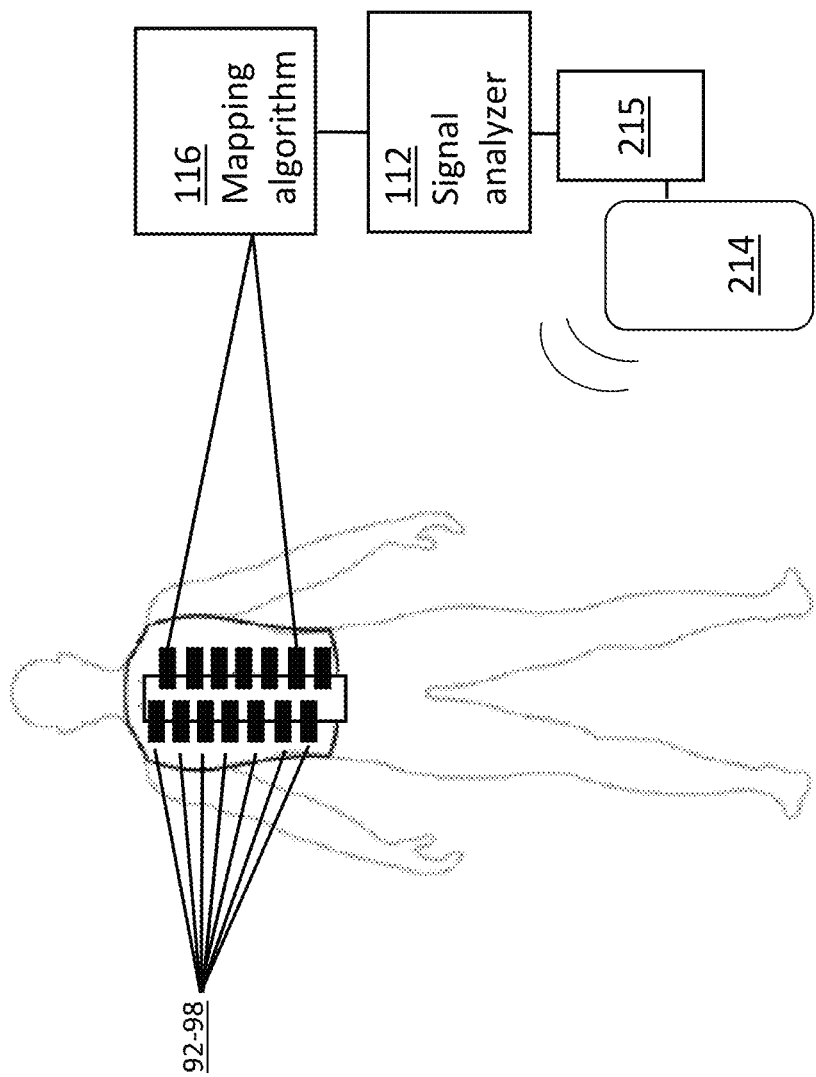
FIG. 14 is a simplified schematic diagram of the different components in a system architecture designed to assist or replace auditory sensations.

FIG. 14 illustrates an audio assistance mode of the vibrational and/or compressive device installed in the therapeutic garment 101. In this embodiment, again an acoustic generator or speaker 214 generates an audio signal that is transmitted through the air to a user. However, this user may have a hearing impairment that restricts his ability to hear the audio signal from speaker 214. Accordingly, the audio signal from speaker 214 is also fed to the signal analyzer 112 which analyzes the frequency pattern of the audio signal in terms of amplitude in a given bandwidth. Alternatively, the audio can be detected by a microphone 215, and the output of the microphone 215 may be sent to the signal analyzer 112.

In either case, the resultant signal analysis is then sent to the mapping algorithm unit 116. This mapping algorithm 116 will map a specific sound as analyzed by the signal analyzer 112 into a tactile sensation delivered to at least one portion of the user's torso, at some amplitude and some repetition rate. Accordingly, the hearing impaired user, although he may not "hear" the audio signal in the traditional sense, that is through his eardrums, the user may still "hear" the audio signal through the tactile sensation of the vibration and/or compression devices installed in the garment or vest 101. Accordingly, the auditory assistance architecture of FIG. 14 may be a device helpful for the hearing impaired to navigate the hearing-capable world.

The essential difference between the audio stimulus architecture of FIG. 13B and the auditory assistance architecture of FIG. 14 is the direction of the auditory signal from auditory device 214. In FIG. 13B, the signal is away from auditory device 214, i.e. 214 is a speaker. In FIG. 14, the signale in into auditory device 215, i.e. 215 is a microphone.

Figure 15:
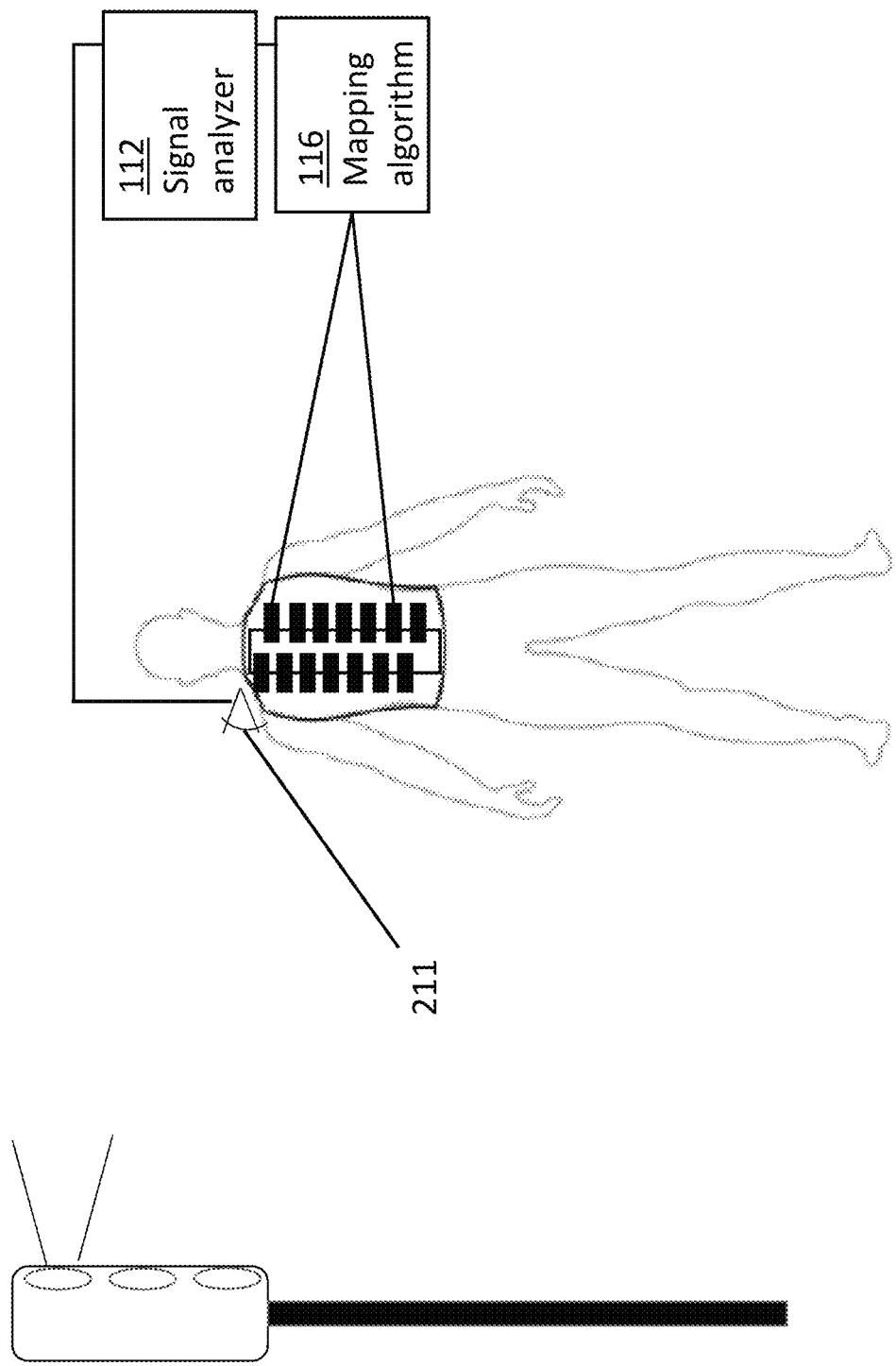
FIG. 15 is a simplified schematic diagram of the different components in a system architecture designed to assist or replace visual sensations.

FIG. 15 illustrates the visual assistance mode of the vibrational and/or compressive device 100 in the wearable garment, 101. In this embodiment, a camera at 211 takes an image of the surroundings of a visually impaired user. This video signal is sent to the signal analyzer 112 which analyzes the amount of power distributed in each frequency range in the visual signal from camera 211. The results of the signal analysis are then fed to the mapping algorithm stage 116 which maps video signal into a motor drive signal which is then delivered to the user through the vast 101. For example, camera 211 may be directed at a busy intersection in front of the user. Because of the large number of moving cars, streetlights, etc., the image may be particularly busy and noisy, and therefore not safe for the visually impaired person to enter the intersection.

Alternatively, the camera image may be fed to an image processing unit, that evaluates the video image and identifies cars, obstructions and movement in a way now common on image processing systems for cars and security systems. In this embodiment, the signal analyzer 112 may be the image processing system.

In any case, when camera 211 and image processing system 112 detects that the intersection is free of traffic, and/or to text a pedestrian crossing indicator across the street, the signal analyzer will determine that this is the situation, and will direct the mapping algorithm to send a tactile signal to the visually impaired person via the wearable garment 101, directing the user to safely that the user may safely enter the cross walk and cross the intersection.

Accordingly, the tactile garment 101 equipped with the vibration and/or compression device is 100, may allow a visually impaired person to "see" in a hearing impaired person to "hear" in a way that is not interfered with by other sources of signal or input. The visual assistance architecture of FIG. 15 may be a device helpful for the sight impaired to navigate the sight-capable world.

It should be understood that the other elements discussed above, but not mentioned expressly in relation to the systems illustrated in FIGS. 13-15, may nonetheless be incorporated in these systems. For example, the feedback loop shown in FIGS. 11 and 12 which allows the systems to learn about its user and adjust its behavior accordingly, may nonetheless also be included in the systems shown in FIGS. 13-15. That is, the auditory and visual assistance and stimulus architectures may also be "self-aware".

The auditory and visual assistance and stimulus systems may also make use of the coupled motors, which may be driven at different frequencies as well as interference and harmonics of those frequencies may also be used on these architectures.

Accordingly, the auditory and visual architectures may also make use of the eccentrically mounted masses illustrated in FIGS. 1-8.

Figure 16:
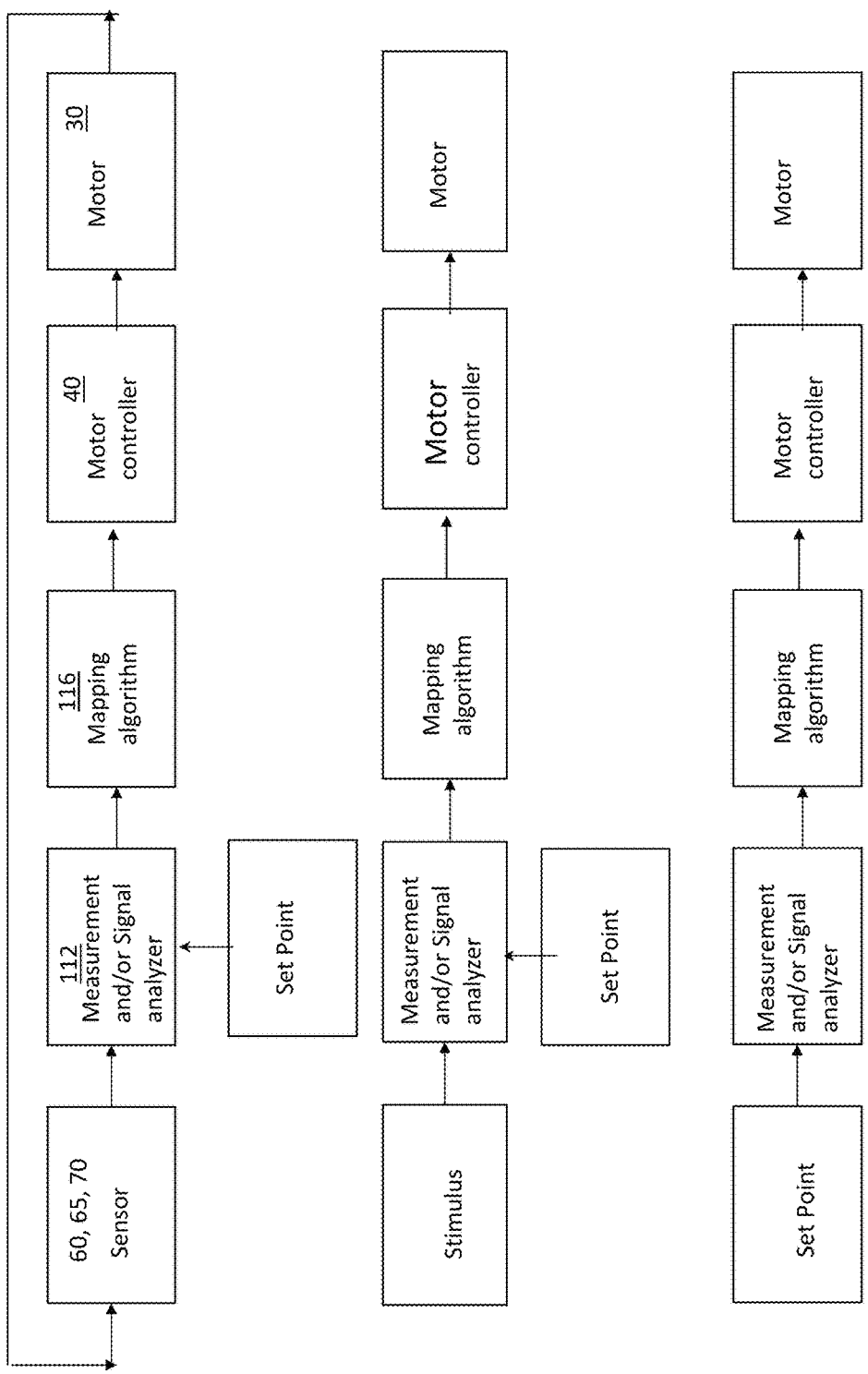
FIG. 16A is a simplified schematic diagram implementing an algorithm for the vibrational and/or compressive devices based on input from a sensor measuring a piece of bioinformation, illustrating the feedback and direct input methods.
FIG. 16B illustrates a method of using the different components in a system architecture in order to augment the perception of a stimulus.
FIG. 16C illustrates a method of using the different components in a system architecture in order to assist or replace the perception of a stimulus.

FIG. 16, including FIGS. 16A, 16B and 16C describe in a general way several methods that can be undertaken using the components just described. Further details associated with these methods will be presented with respect to the detailed applications that will be described in the next section.

FIG. 16A is a flow chart illustrating in method format the basic components of the architectures shown in FIGS. 12-15. In FIG. 16A, the first step of the method may be to query a sensor, in order to measure a piece of bioinformation indicative of the users situation or status. The sensor may be, for example, any or a combination of those listed above, or it may be a different sensor operating on a different piece of bioinformation.

In any case, the sensor output may be recorded, sorted and analyzed by a computer 110. The computer 110 may determine directly an algorithm to apply to the motor, or the computer may send the data to a dedicated analyzer 112. This analyzer 112 may then send a message to the mapping or decision making element 116 as to the user's status or situation, such as their emotional state or physiological state. The mapping or decision making unit 116 may then make a decision (based on for example a lookup table) regarding the algorithm to apply to the motors and vest 101, in response to the user's condition, as measured by the at least one sensor.

In the feedback embodiment, upon application of the tactile sensation from the vibrational and/or compressive device executing the algorithm, the sensors may be polled again, and any changes in the status of the user as a result of the application of the tactile sensation, may be evaluated. Based on the results, the computer 110, signal analyzer 112 or the mapping element 116 may be updated to new values, based on the response of the user.

One feature of this method is that the computer, the analysis unit and/or the look up table, may be altered based on the new sensor results. That is, the system can learn based on the success or failure in achieving a targeted state of the user.

In FIG. 16B, a stimulus may be applied to the user. The stimulus may be either auditory or visual, for example, or the stimulus may be some other sensation. The second stage 112 is the signal analyzer stage, wherein the frequency components of the stimulus are analyzed. The results of this analysis then may go to the mapping algorithm stage 116. The mapping determines the algorithm appropriate for this stimulus analysis. The mapping stage 116 then sends the selected algorithm to the motor controller 40, which applies the algorithm to the motor 30. The motor 30 then delivers the tactile sensation to the vest 101 and user. The effect of this method is to map one type of sensation (e.g. audio or visual) to a tactile sensation that is applied directly to the user's body using the vibrational and/or compressive devices 100 deployed in the architecture. The architecture illustrated in FIG. 16B thereby becomes a parallel sensory input mechanism, which is linked by the algorithm to the sensations coming through the usual sensory channels, which may significantly heighten or at least alter the user's perception of the stimulus.

In FIG. 16C instead of the stimulus being applied to a user, a sensor is deployed on or near the user which will detect electronically the stimulus applied effectively creating a set point for the input signal. The sensor may be, for example, a camera or a microphone as was illustrated in FIGS. 14 and 15. The sensor may then send the set point value or input signal to the signal analyzer unit 112 which analyzes the input signal and sends the output to the mapping algorithm stage 116. The mapping algorithm stage 116 then chooses an algorithm and directs the motor controller 40 to control the motor 30 according to this algorithm. This method also accomplishes a mapping of a stimulus directed to one sensory organ (sight or sound) into a tactile sensation applied directly to the user's body. The architecture illustrated in FIG. 16C thereby becomes a substitute or supplementary sensory input mechanism, which is linked by the algorithm to the sensations coming through the usual sensory channels. This supplementation of the usual sensory channel may allow the blind to "see" or the hearing impaired to "hear".

In an embodiment, the audio signal is separated using an analog hardware approach. Input music signal is simultaneously split into a frequency band employing analog biquad active filters. Filters employ second-order biquads for the low and high frequency cutoffs for each band. The filters are of maximally flat design (e.g. Butterworth). The range considered here is the bass band of 10 Hz-250 Hz. The energy in the bass filter band is tracked using an envelope detector (ED). The output of the ED is known as magnitude envelope (ME). The ED consists of an absolute value converter followed by a 10 Hz, biquad, butterworth, low pass filter. The output from the ED is sampled by the host microcontroller to be used as a signal drive to control the PWM drive signal to device 100. In one embodiment, the ME output of the ED can also be differentiated to provide a derivative of magnitude envelope (DME), Either the ME or DME can be employed as the PWM control drive signal.

In another embodiment, the audio signal is inputted directly into the device's microprocessor. Here software analyzes and separates the frequency spectrum of the signal, for example, using a Fast Fourier Transform (FFT). The software then outputs signals for each of the motors through their respective motor controller. The software determines which frequency range to be assigned to each motor and can be adjusted. The software also creates an audio output which is heard by a user, by either plugging directly into the device or through a Bluetooth connection. The audio output signal is delayed to account for the lag in motor ramp time. This delay is tuned and adjusted to alter the user's experience.

In some embodiments, the tactile stimulation vest has a variety of tactile effects that drive the motors in specific patterns. The inputted music is used to trigger the different effect patterns. The music is split into 3, but not limited to 3, frequency channels that each trigger different effects which are then expressed through motors associated with those frequencies. For example, an input signal determined to be in the bass frequency spectrum will trigger an effect where the low frequency motors are pulsed on and off with the event of a bass signal.

In embodiments, the input signal can trigger different vibration patterns. In embodiments, one vibration pattern is Pulse. Pulse is essentially a square wave that turns all the motors on in that specific frequency and vibration class. A low frequency or bass audio signal will trigger a square wave to be sent to the low-frequency motors. The amplitude of the volume of the audio signal in that spectrum will be proportional to the intensity of the signal sent to the motors. For example, a 0 dB audio frequency represents full volume and will trigger a 100% intensity driving of the eccentric motors. In another embodiment, the output signal is sent to a voice coil activated linear actuated mass haptic transducer. In the current hardware architecture, this is represented by sending a PWM signal of 0-4095. 0 being related to zero audio signal, and 4095 representing full audio volume.

In embodiments, one vibration pattern is Ramp. Ramp is a signal sent to the motors that has a ramp from 0 to the desired amplitude. The signal then drops to 0 immediately. This signal can be represented in a sawtooth waveform or motor drive signal.

In embodiments, one vibration pattern is Cascade. Cascade is an effect that drives sequentially each motor in a specific class. In the vest this manifests as haptic transducers being actuated so that they start with the lowest transducer and sequentially actuate each transducer moving up the body. Inversely, the transducers can be actuated so that the top motors are actuated first and the actuation cascades down the body. It's essentially a wave traveling up or down the tactile vest.

In embodiments, one vibration pattern is Burst. Burst causes the motors to be actuated sequentially, in a given class. The Burst starts at a central haptic transducer location on the body and then cascades up and down, and from inside to outside.

In embodiments, one vibration pattern is Bilateral. Bilateral actuates the motors on the left and right side of the vest separately. In one embodiment alternating impulses are sent to the left and then to the right side. For example, when a threshold signal in the music has detected the transducers in that predetermined class are actuated at a relative intensity arbitrarily on the left side first. The next event then causes the actuation of the transducers on the right side. And they continue to alternate causing bilateral stimulation of the user.

In one embodiment the motors are held at a constant predetermined value. When there is a triggered event the transducers are driven to an even higher state. In another embodiment of the always-on mode, the derivative of the signal is taken. This causes the motors to first increase above the baseline and then to decrease below the baseline by a similar amount directly after.

In embodiments, the device uses integrated biometrics. Biometrics are used to inform the user of their physiological state. Biometrics are also used to alter the experience of the user by feeding it back into the software or hardware of the device. By creating a feedback loop the device optimizes for specific outcomes. To accomplish this a simple artificial intelligence (AI) can be implemented. The AI will be informed of the desired arousal state, low or high. The AI will monitor the response of the user's biometric data over a moving time window of 5 seconds to 1 minute (depending on the biometric data being used). The AI will learn the effect of different input signals on the user by correlating them with biometric data. As the AI learns the effect of different patterns it can then start to change the input sequencing to move the user to a desired arousal state.

Test patterns are created that run through a diagnostic sequence of spatial patterning between transducers and frequency sweeps of the individual transducers. By measuring biometrics during the sequence the device learns what a person responds best to. This information is then used to create a user specific routine or sets of routines to alter a person's state accordingly.

By monitoring a user's electrodermal activity (EDA) the arousal state of a user can be detected. The EDA information can then be fed back through the device to modify the routine accordingly. If it is determined that the person is being aroused by the current sequence, and the goal is to arouse the person, then the artificial intelligence will learn that the current sequence had that effect and then choose to explore that space to continue to arouse a person. If the goal is to calm a person, then the AI will choose to avoid similar sequencing in order to lower their arousal state.

In one embodiment the device has an integrated respiration sensor. This sensor is a serpentine wire that runs circumferential to the body. Any expansion causes a change in the impedance of the wire. This difference can be measured and used to direct the activities of the device.

Integrated into the device are electrodes that can detect the heartbeat of the user. From the heart beat information such as heart rate, heart rate variability, R-R interbeat frequency, R-wave amplitude, and others can be used to assess the physiological state of the user. This information is then used through a feedback system in either hardware or software to alter the output of the device.

Using electrodes on the face electromyographic (EMG) data can be measured on the corrugator, zygomatic, and frontalis muscles. Activation of these muscles are indicative of arousal and valence states of a person. By measuring the EMG states the sequence can be altered to drive a person to a specific state. For example, a decrease in corrugator activity will indicate a person is becoming more calm. If the device senses a decrease in corrugator activity, then it can immediately look back to see what sequence triggered that response and then repeat the sequence.

Similarly with EMG data from the zygomatic muscle. An increase in this muscle activity indicates an increase in pleasure. To give the user a more pleasurable experience the software can look at what sequence or frequency caused the user to have a pleasurable experience and then repeat it and explore further in that space.

The device activates the afferent nervous system through mechanical modulation of the body's mechanoreceptors, and/or baroreceptors of the heart and/or the spinal ganglia. A signal is sent to haptic transducers that transform the electrical energy into mechanical energy. The device couples the mechanical oscillations of the transducers to the body's mechanoreceptors, and/or baroreceptors of the heart and/or the spinal ganglia. The mechanoreceptors, and/or baroreceptors of the heart and/or the spinal ganglia transform the mechanical energy they receive into an electro/chemical signal which is sent through the bodies afferent nervous system to the brain. The brain then interprets these signals having a profound effect on the physiological, psychological (mental), and emotional state of the user.

Due to thermodynamics, the energy being received by the brain has to be dissipated somewhere. The brain dissipates this energy to other parts of the brain. Depending on the nature of the stimulation the arousal state of the user will be affected differently. Irrespective of signal type the device will have an increase on the valence of a user's emotional state. It is believed that this is caused by excess energy being dissipated to the body's pleasure sensor. Or it could simply be because we like being touched. Irrespective of the mechanism the device induces an increase in valence or feeling good.

In this regard the device couples to the body's machinery to create a unified device for inducing pleasure with the arousal state being determined by the nature of the input signal. This is extremely relevant when the input signal is music. The device transforms the music signal into waveform or motor drive signal signals that drive the haptic transducers. Thus the nature of the music is translated into the mechanical modulations Music that has a lot of variability, or high intensity music will both increase the valence and arousal state of the user. In essence getting them pumped up and ready to go. Music that is less variable, or calming music, will increase the valence and decrease their arousal state, thus causing a sense of pleasant relaxation.

Communication and interfacing among modules and/or components may be by any operable modality, such as, for example, by physical components, physical wiring, electronic circuitry, integrated circuits, and/or wireless and/or optical linkages. The disclosure hereof extends to all such equivalent arrangements.

Applications

In addition to the applications discussed in detail below, the systems described above may also be used to treat or improve circulation in general.

In one embodiment the device may stimulate the lymphatic system.

In one embodiment the device may be used to treat autism.

In one embodiment the device may be used to treat ADD and/or ADHD. In one embodiment the device may be used to treat depression.

In one embodiment the device 100 is a DC brushless motor.

In embodiments, a haptic actuator could include any device or component operable to impart a controllable force, vibration, or other haptic effect to a body. Examples of haptic actuators according to the disclosure hereof could include, for example, eccentric rotating mass vibration motors, linear resonate masses, or piezoelectric haptic motors. The motors may be driven by hardware running a software routine or driven by another signal. Below the different components have been broken down and explained in sections.

In one embodiment, the system shown in FIG. 16B may be used to help the sight-impaired to navigate the sight-capable world. The vest 101 may be equipped with a video camera 212 that monitors conditions in the crosswalk of an intersection. A signal analyzer 112 attached to the camera determines if the pedestrian crossing light is illuminated, or other conditions, such that it is safe to enter the crosswalk. If the camera detects a green "pedestrian crossing" is showing on the traffic light, it sends a "safe to cross" signal to the mapping or decision making unit 116. The mapping or decision making unit 116 may send, for example, a rhythmic vibrational and/or compressive wave algorithm to the controller, which may send that behavior to motors on the right side of vest 101.

However, if the signal analysis unit 212 determines that cars are approaching the intersection at speed or detect some other unsafe conditions, such as the "no crossing" light is illuminated, it may send a "not safe to cross" signal to the mapping or decision making unit 116. The mapping unit 116 may select a percussive and stronger set of pulses as the appropriate algorithm, and send this to the motor controllers 40 controlling the left side motors. The percussive sensation is thereby applied to the left side of the user's torso through the vest 101.

These signals may be clearly and unambiguously sent to the user, who may perceive the signal in a reliable way. This communication channel is not subject to the usual environmental noise (as would an audio cue) and they are sensed only by the wearer. Accordingly, a system for the visually impaired is envisioned, using a plurality of vibrational and/or compressive devices, and a sensor deployed in close proximity to the user which assesses a situation near the user, wherein the sensor communicates with the vibrational and/or compressive devices such that the vibrational and/or compressive devices deliver a signal to the user, wherein the signal is based on the situation assessed by the sensor.

Figure 18B:
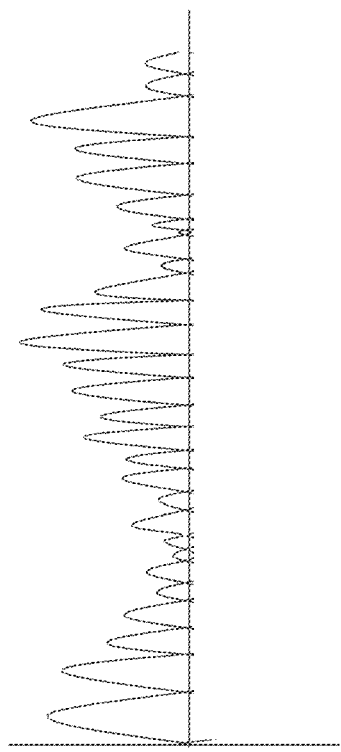
FIG. 18A, FIG. 18B, FIG. 18C, and FIG. 18D show how an arbitrary waveform is converted into a motor drive signal.
Figure 18D:
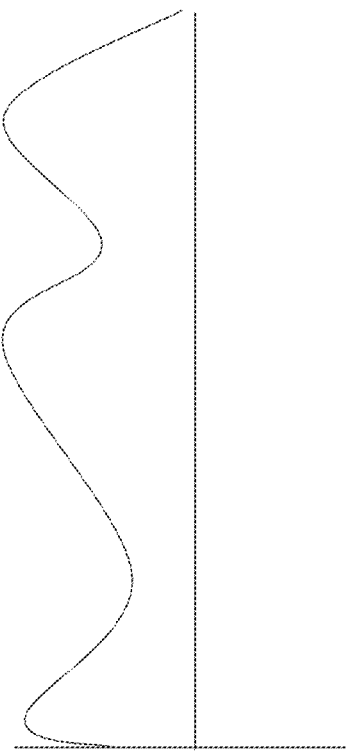
Figure 18A:
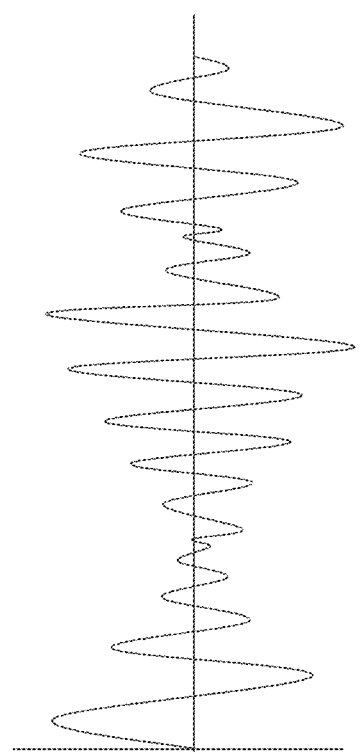
Figure 18C:
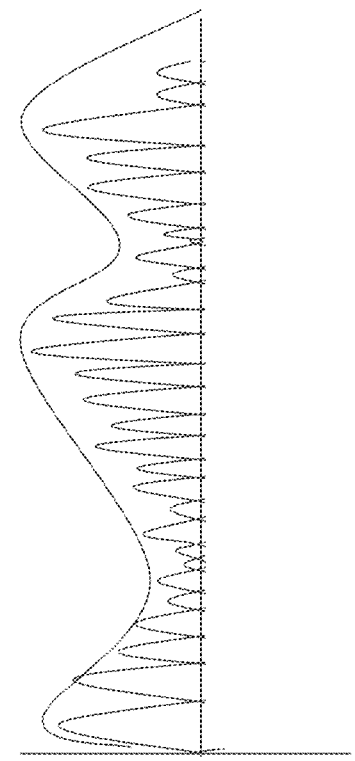

Another application using the system architecture illustrated in FIG. 13 involves the handling of frequency components in an audio signal input 310 listened to by a user wearing a vest 101. As before, the audio signal input 310 may be in the form of music from a speaker 214 as shown in FIG. 13A. In this embodiment, the signal analyzer 112 may be a spectrum analyzer which displays the magnitude of the signal in certain frequency ranges FIG. 18A. The output of the spectrum analyzer may then be sent to an integrator, which integrates the total energy or power within a certain spectral range FIG. 18B. The result of this integration is the magnitude of that audio power within a frequency band FIG. 18C. This number may then be sent to the mapper FIG. 18D, which may have a lookup table relating a motor rpm to a certain integrated power. The motor driver 40 may then be given this target rpm, and drives the motor 30 to the value from the lookup table.

More specifically, in some embodiments, a voltage may be sent (i.e. a 2.5-5V signal) to another board which transforms that drive voltage into a Pulse Width Modulated (PWM) signal that drives the motor. In this case, 2.5V may correspond to 0 revolutions per minute (rpm) and 5V may correspond to the maximum rpm.

The relationship between the integrated power and the motor rpm may be linear, for example, such that when the power is higher, the rpm is increased. However, this is exemplary only, and the relationship may be arbitrarily complex.

Many relationships between the audio signal and the motor response can be envisioned. For example, it may be ascertained that applying vibration and/or compression to a users torso via the vest 101 equipped with multiple compressor devices 100, may enhance the uses enjoyment of that music. This may be particularly true if the bass portion of the audio signal is mapped to the vibration and/or compression behavior of the vibrational and/or compressive device is 100, or when extreme treble notes are present in the music. Accordingly, the integration process may be applied to the frequency components in the bass range of the audio spectrum.

In this embodiment the mapping algorithm 116 chosen may be to create a large perceptible massaging movement that is correlated to the bass frequencies in an audio signal. The mapping algorithm would implement that algorithm as a result of the power measurement from signal analyzer 112. If the power is higher in the bass register, the mapping algorithm 116 may choose a higher revolution rate on the eccentric masses of the motor, so by speeding up the massaging rate of the vest 101. In this scenario, the mapping algorithm maps the energy in a spectral frequency range to an RPM rate of the motor. This mapping concept will also be used in FIGS. 14 and 15 where an audio, or video signal is mapped from an intensity profile into a mapping algorithm.

Accordingly, in one embodiment, a vest 101 equipped with at least one motor 100 with an eccentric rotating mass is worn by a user, while the user is exposed to an audio signal 214. A spectrum analyzer 112 measures the energy in a selected band of audio frequencies of the audio signal, and an integrator integrates the energy over this selected band. The at least one motor 100 is then driven at an rpm which is proportional to the integrated power level.

In another embodiment using the system architecture of FIG. 14, a vest is used to improve the intelligibility of a hearing-impaired person. In this embodiment, a set of words and/or sentences is spoken clearly into microphone 215 by a hearing-capable speaker. This audio signal is analyzed by signal analyzer 112 which outputs a detailed frequency spectrum of the spoken message. This spectrum is mapped to a particular configuration of vibration and/or compressive devices 100 in the vest 101. The hearing-impaired person then attempts to repeat the audio signal, which is again detected by microphone 215. The signal analyzer analyzes the hearing-impaired user's speech and determines the spectral differences between the hearing-impaired persons speech, and the hearing-capable persons speech. An algorithm that maps the audio spectrum into complex motor behavior of the motors with ERMs installed in the vest. The hearing impaired person can continue to practice speaking the words in order to minimize the detected differences between the two audio signals.

In these embodiments, the signal analyzer may be programmed to generate a plurality of motor drive waveforms based on different features of the analyzed signal, and wherein the controller delivers the plurality of motor drive waveforms to a plurality of vibration producing devices to deliver a plurality of different vibrations to a plurality of areas on the body. The controller may also be programmed to execute a sequence of spatially varying patterns of vibration using the plurality of motor drive waveforms delivered to the plurality of vibration producing devices, based on the analyzed signal. The different features correspond to at least one of a letter of an alphabet, a syllable in speech, a color and a pattern in the input signal, and an integrated power within a frequency range of an audio spectrum, such that the input signal is mapped to a tactile sensation by the device.

In these embodiments, the input signal may include at least two input signals corresponding to left and right stereo audio signal, and wherein the signal analyzer generates at least two motor drive waveforms based on the left and right audio signals.

Similar to the audio application described elsewhere, the plurality of vibration producing devices may be disposed adjacent to one another with one of the plurality of vibration producing devices on one side of a centerline of the body and the another of the plurality of vibration producing devices on the other side of the centerline of the body. The vibration producing devices may be attached by an attachment mechanism to a platform, and wherein the attachment mechanism transmits the vibration to the body.

The platform may be at least one of a garment, a chair, a mattress, a hat, a headband, an earring and a cushion. In other embodiments, The platform may be a reclining chair with elevated foot support and a plurality of vibration producing devices are coupled through the reclining chair to the body of the user, wherein the plurality of vibration producing devices are disposed on both sides of the centerline of the body.

The different features correspond to at least one of a letter of an alphabet, a syllable in speech, a color and a pattern in the input signal, and an integrated power within a frequency range of an audio spectrum, such that the input signal is mapped to a tactile sensation by the device.

In one embodiment the device may be used to help a user obtain a meditative state. The devices in FIGS. 9 and 10 direct vibrations through the body in patterns that urge the user's physiology into a state conducive for meditation. In one embodiment users sit on a cushion FIG. 10C or clip device 100 in FIG. 10D to their ears or wear a headband embedded with device 100. The controller 110 sends a drive signal to the motors 100 that transmit vibrations to the user sitting on the cushion 16. In one embodiment the vibration amplitude and frequency increases sinusoidally in time, although it could be any arbitrary periodic waveform or motor drive signal. The wavelength of the sinusoidal rise and fall of the vibrations of the motors vary within the range of human respiration of 2-20 breaths per minute. A typical program sequence may start at a typical resting breath rate of 15 breaths per minute and then become slower over time. Over time, the user's respiration will begin naturally to follow the rise and fall of the vibrations of the motor(s). As the wavelength of the sinusoidal rising and falling of the motor vibrations increases, the user's respiration rate will also slow. Accordingly, the program sequence may be a sine wave, increasing and decreasing in intensity with characteristic frequency, or wavelength. In some embodiments, the sinusoid may be chosen with respect to the respiration rate. By matching the respiration rate to the sequence wavelength we can lock on, and then subsequently slow the sequence frequency to slow the respiration rate. In one embodiment, a test sequence is run to determine how slow a user can breathe. This respiration rate is then used as the target wavelength for the sinusoidal variation of the motor vibrations.

In another embodiment, using the control architecture of FIG. 16A the sensor 65 detects a person's respiration rate. The control system then adjusts the sinusoidal wavelength to match the user's respiration with or without a bias. The "bias" may be understood to be a quantity related to the magnitude and direction of the difference between the sensed respiration rate and the targeted respiration rate. If the bias is applied to make the wavelength longer in the vibration it will cause the users respiration to slow. If the wavelength of the sinusoidal vibration is decreased then the respiration rate of the user will increase.

In another embodiment a user's respiration and heart rates are monitored. The control in FIG. 16C inputs both these signals, matches the motor drive to the respiration as described above and the control algorithm then modifies the input signal to drive the user to a state of increased Heart Rate Variability (HRV). Tracking Heart Rate (HR) the system continues to increase the wavelength of the sinusoidal variation as the HRV amplitude continues to increase. If HRV begins to decrease then the sinusoidal wavelength reverts and holds constant where the maximum HRV occurred. With this example, it can be seen that the control architecture can be configured to optimize any quantity, including a complex form of multiple input parameters such as maximizing the HRV divided by the Respiration Rate and so driving the user to both a low Respiration Rate and large HRV.

Accordingly, in one embodiment, a cushion 16 equipped with at least one motor 100 with an eccentric rotating mass is sat on by a user, while the user is exposed to a signal 116. A spectrum analyzer 112 measures the bioinformation with sensor 60, 65 or 70, and adjusts the signal 116. This creates a closed feedback loop so that the computer adjusts signal 116 to then drive the user's bioinformation to a state determined by their physiology.

Figure 17:
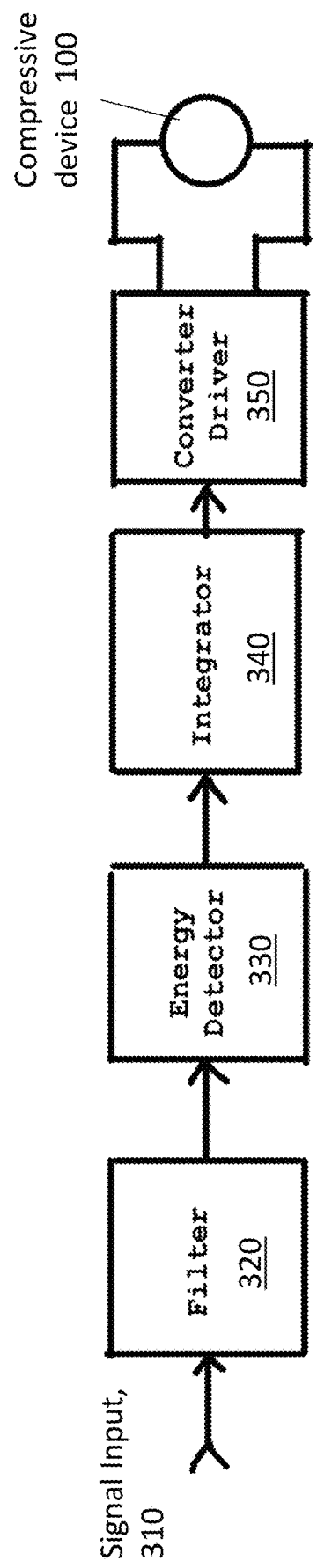
FIG. 17 is an example schematic diagram showing processing of signals resulting in an output drive for the vibration device(s). This could be an audio signal input with wide bandwidth (such as music) and the output drive is then translated to a lower bandwidth.

In one embodiment, the system shown in FIG. 17 may be used to improve workplace productivity by providing a reset to workers. The vest 101 or other devices in FIG. 10 equipped with eccentric rotating masses 100 can perform a specific sequence of frequency and amplitude modulated vibrations. Premade sequences can be played to elicit specific effects on the users mental, physical and emotional state. In another embodiment the architecture of FIG. 17 is used to transform a musical input into therapeutic compression. The combination of music with vibration improves the user experience, increasing compliance of use. The music also acts on the users psychology to direct the energy from the vibrations in a positive direction. In another embodiment the device uses a system architecture from FIG. 16 to detect a user's current mental, emotional, and/or physiological state and then modulate the frequency and amplitude of the vibrations monitoring the biometric response of the user. The device then alters the modulations to drive the desired biometrics in the direction of a specific state. An example of this could be to reduce respiration rate or increase HRV or decrease Beta EEG activity and increase Theta EEG activity.

Accordingly, a system for improving workplace productivity is envisioned, using a plurality of vibrational and/or compressive devices, and specific frequency and amplitude modulation, a user can in a short period of time 5-30 minutes increase their focus and productivity.

In one embodiment, vest 101 may be used to help prevent the formation of PTSD. The vest 101 may be equipped in an emergency responder vehicle, or at the base for when the war fighter returns from an active theater of battle, or as a part of a trauma relief unit heading into a disaster zone. In each of these cases one has experienced a significantly negative and powerful event that may take deep roots in a person's psychology and physiology causing a lifetime of adverse reactions such as sleep loss, depression, anger, and alcohol and substance abuse. In this embodiment, the vest 101 is applied to the person that experienced a traumatic event in a relatively short time period after the event. The vest 101 activates eccentric rotation motors 100 that send vibrations into the body. As the traumatic events are taking psychological and physiological hold in the mind and body, these vibrations are translated into electrical impulses by the body that block those traumatic experiences from taking root. Monitoring the HRV of the user the algorithm adjusts the vibration frequency and amplitude to increase HRV, bringing the person out of a sympathetic stress state and into a parasympathetic recovery state.

Accordingly, a system for reducing or eliminating the formation of stored trauma in the mind or body, using a plurality of vibrational and/or compressive devices, and specific frequency and amplitude modulation is described.

In one embodiment the device reinforces and regulates a user's biorhythms by creating vibration patterns near or at the users current biorhythm frequency and then guides the user to an optimized rate. Just as a pacemaker is used to keep a steady heartbeat, this system helps guide other oscillatory biological systems to a healthy and regulated state. The device can operate in either an open loop (FIG. 16C) or closed loop (FIG. 16A).

Figure 19:
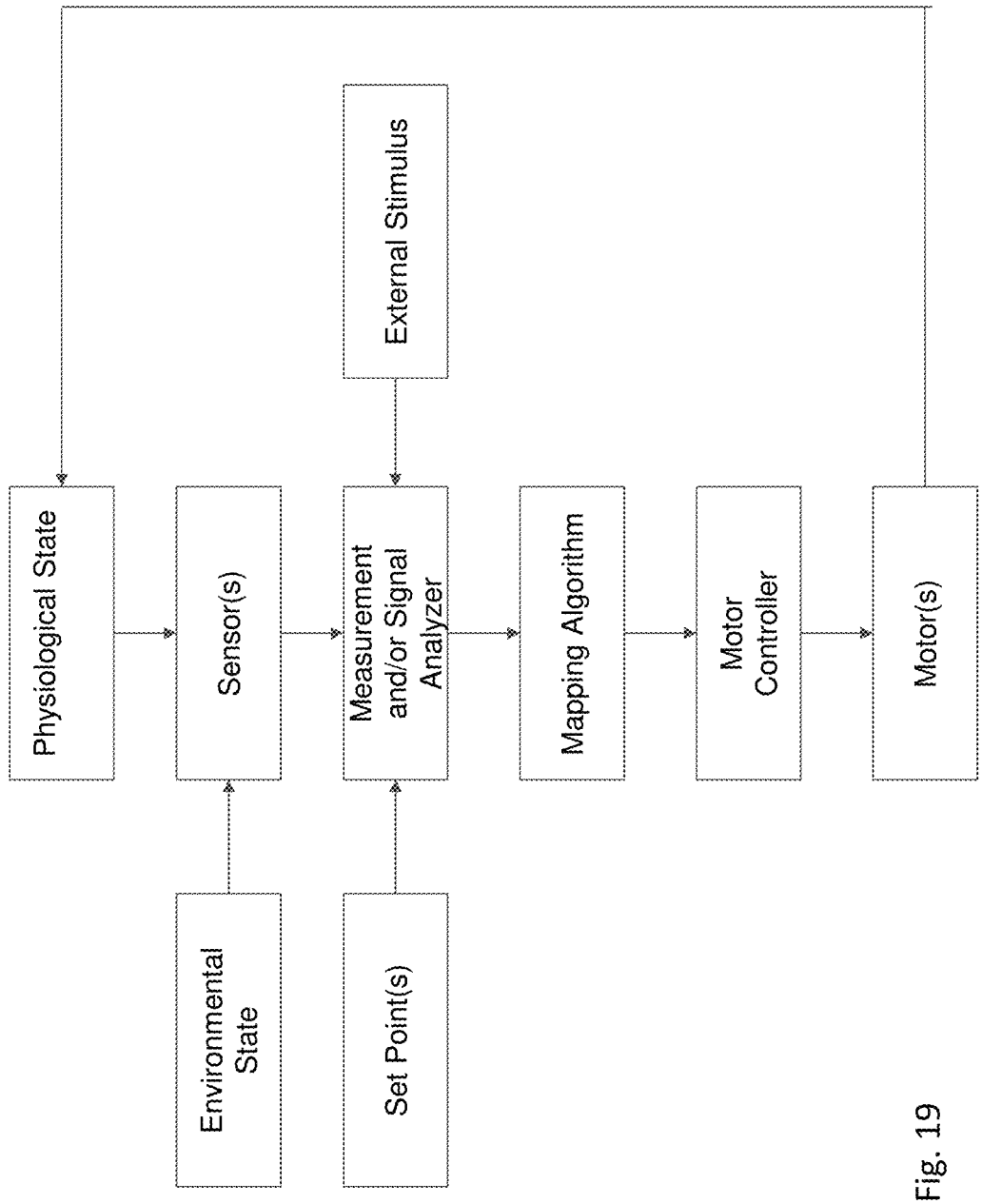
FIG. 19 is a flowchart showing sensing, driving and feedback.

In a closed loop architecture the device uses a system of FIG. 19 to create a closed loop feedback between compressive device 100, sensor 103, computer 110, analyzer 112, and mapper 116. In the system of FIG. 19 the user inputs a desired physiological state or health outcome. The system then asses the users current physiological state using sensor(s) 103. The system then goes to a look-up table to determine, and/or an AI calculates the most optimal oscillation rate of various systems, including but not limited to circulatory, respiration, nervous, lymphatic, endocrine, and digestive systems. The system in FIG. 16A locks onto the user's physiological state, e.g brainwaves, respiration rate, heart rate, creating similar physiological pulsing through compressive devices 100. The system then biases the pulsing rates in the direction of an optimized pattern guiding the user's physiological state towards the determined set-point. If the difference between a user's physiological rate determined from sensors 103, and the pulsing from compressive devices 100 exceed a certain value then the computer 110 will maintain that frequency of pulsing until the difference reduces. In other words, the system will continue to drive the user's physiological state to the optimized rate as long as their physiology can keep up. When it cannot it holds steady at that rate.

Operating in an open loop architecture the mapping algorithm 116 uses a set sequence of frequency, amplitude and location modulation to guide a user to a desired physiological rate. This may be but not limited to creating a sinusoidal envelope of vibrations of 0.016 Hz-0.5 Hz, which then will cause a user's respiration rate to be 1-30 breaths per minute. Similarly the entire spectrum of brainwave frequencies from 0.001-100 Hz can be driven with this device.

To achieve this, compressive devices 100 and 100' modulate at frequencies corresponding to biophysical periodicity of humans. The compressive device 100 oscillates in a frequency range from 1 Hz to 100 Hz corresponding to the human brainwave frequency spectrum and heart rate.

The plurality of compressive devices 100' and 100" creates interference frequencies, or beat frequencies, with a range between 0.1 Hz and 20 Hz. These frequencies correspond to the lower end of the brainwave frequency spectrum and the range of human heart rates.

The motor controller 40 increases and decreases the compressive device 100 frequency and amplitude to create waves or pulsing arbitrarily slow to match low frequency oscillations of the body such as respiration, gastrointestinal peristalsis, or cerebrospinal fluid. Of particular interest is the frequency range of 0.01-1 Hz as this corresponds to slower human biophysical periodicity, such as human respiration rates, electrogastinal, and cerebrospinal fluid flush rates during NREM sleep.

FIG. 19 illustrates an architecture for being able to sense, adapt and guide human physiological and psychological state. By being able to match human physiological periodicity it is possible to match and reinforce biological actions such as respiration, heart rate, and brainwave activity. It is also then possible to guide these physiological functions to faster or slower rates.

Figure 10:
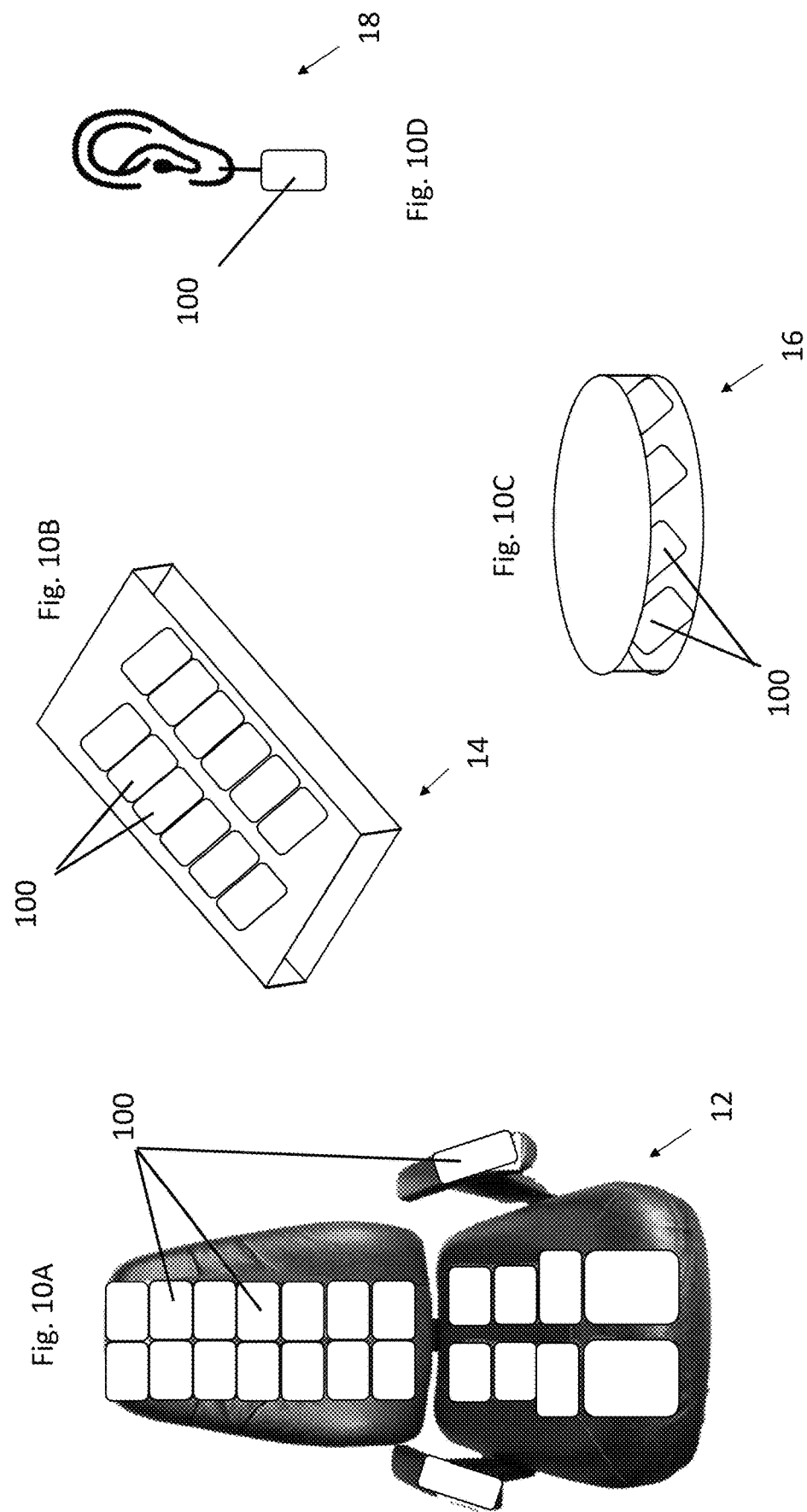
FIG. 10A, FIG. 10B, FIG. 10C, and FIG. 10D, are illustrations showing various delivery platforms and making use of the vibrational and/or compressive devices.

The device 100 and devices in FIG. 10 operate at frequency ranges matching NREM brain waves of 0.05-4 Hz and the flush frequency of cerebrospinal fluid (CSF) of ~0.05 HZ to reinforce the deep sleep that assists in metabolite waste cleaning.

Using the system in FIG. 16C the compressive devices 100 pulse at a predetermined frequency. Reinforcing the CSF flush rate and deep delta brainwaves is achieved by the controller increasing and decreasing the intensity at a rate of approximately 0.05-0.1 Hz (3-6 cycles per minute). Additionally a beat frequency 80 can be added to aid in reinforcing circulatory and deep delta brainwaves.

In another embodiment the system of FIG. 19 is used to detect the user state and reinforce the sleep benefits. The sensor 60, 65, 70 detects the users EEG, ECG, and/or PPG. The analyzer 112 then uses AI, a look-up table, or tensor flow analysis, to determine the appropriate motor mapping. The motor controller 40 then drives the compressive devices 100 accordingly. The sensor information 60, 65, 70 is again analyzed and adjustments are made to the frequency, amplitude, and location of the compressive device(s) 100 to reinforce delta brainwaves and to improve the movement of CSF.

A device that inputs a spectrum of frequencies (310), isolates a specific frequency range (320) (FIG. 18A), determines the average power (330) of that frequency range (FIG. 18B) and integrates that average power over a specific moving time window (340) (FIG. 18C), and outputs a control signal (FIG. 18D) related to the average power in the frequency range.

A signal processing method that involves the measurement of the average energy present in specific audible frequency bands, over specific moving-time windows, to control the frequency of oscillation of stimulator(s) (mechanical, electrical, light, or auditory stimulators) applied to the human body.

A specific frequency band, or bands, located within the auditory spectrum (1 Hz-20 kHz) is/are isolated to determine the average power signal [A(t)], representing the band or combined bands, over a specific moving-time window. This frequency band isolation method can be accomplished via analog or digital methods, including the use of lowpass, highpass and/or bandpass filters or via transformations such as the Fast Fourier Transform.

Once A[t] is defined, it is used to control the operating frequency of a voltage controlled oscillator (VCO) or the speed of a rotating Electric Motor.

In the case of application to VCO, the VCO will then drive an amplifier to actuate electromagnetic transducers that produce tactile impulses in relation to the VCO output. A separate control is used to modulate the amplitude of the VCO output, via the amplifier.

In another embodiment, the VCO can be used to control the frequencies being sent to an electrical stimulator. The amplitude of the stimulus being subject to separate control.

In the case of application to an Electric Motor, the motor's speed (rotational rate) is determined by the value of A(t). Typically, A(t) can be conditioned to drive the motor via pulse width modulation (PWM) methods, however a linear amplifier could also be used. The Electric Motor has an attached eccentric weight to the shaft that will result in variations of force as the shaft rotates.

In this embodiment the device is used to assist a user in obtaining improved sleep. The device FIG. 10C may have a single or multiple compression devices 100 embedded in a mattress, cushion, pillow, neck pillow, or other compliant device that makes intimate contact with a user while sleeping.

In one embodiment the device uses the system in FIG. 16C. The user inputs the desired sleep duration. The computer then uses an algorithm to determine the most optimal sleep pattern for the user and sends this routine to the motor controller which then drives the compressive elements 100 in the pattern. The pattern optimizes for bringing a user into a NREM deep sleep. Furthermore the device uses physiological pulsing to stabilize and sync the users biological functions, including, but not limited to respiration rate, heart rate, cerebrospinal fluid flush rate, and delta brainwave pulse rates.

In another embodiment the device uses a system of FIG. 19 to create a closed loop feedback between compressive device 100, sensor 103, computer 110, analyzer 112, and mapper 116. In the system of FIG. 19 the user inputs the duration of desired sleep. The system then asses the users current physiological state using sensor(s) 103. The system then goes to a look-up table to determine, and/or an AI calculates the most optimal sleep pattern for the user. The system locks onto their physiological state, e.g brainwaves, respiration rate, heart rate, creating similar physiological pulsing through compressive devices 100. The system then biases the pulsing rates in the direction of an optimized pattern guiding the user's physiological state towards the determined set-point. If the difference between a user's physiological rate determined from sensors 103, and the pulsing from compressive devices 100 exceed a certain value then the computer 110 will maintain that frequency of pulsing until the difference reduces. In other words, the system will continue to drive the user's physiological state to the optimized rate as long as their physiology can keep up. When it cannot it holds steady at that rate.

In this embodiment a device for optimizing a user's sleep by modulating the physiological pulsing of compressive devices 100 is used to guide a user's physiology through an optimized sleep pattern while reinforcing critical physiological rhythms such as respiration, heart rate, brainwave state, and cerebrospinal fluid flushing rates.

In this embodiment device 100, 100' or 100" is coupled directly to the body. The device pulses mechanical vibrations which stimulates the circulatory system.

Many additional applications exist that have not been described in detail herein, however are nonetheless within the scope of this invention. These applications may include, but are not limited to, human tuner, chronic fatigue, autism, post traumatic stress disorder (PTSD), attention deficit hyperactivity disorder (ADHA), sleep disorders, sports performance, self care, and driver alertness, for example.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

In one embodiment the device is a recliner with devices 100 integrated in the back, seat and leg rest in two parallel rows running from the foot of the recliner to the very top where the user's head rests. The devices 100 are 0.25 to 7 inches apart in distance near edge to edge in the axis aligned with the users body head to toe and the motors are spaced 0.25 to 7 inches near edge to edge across the centerline of the chair corresponding to the users spine.

The recliner may also have electrodes integrated into the arms for biometric detection of but not limited to electrocardiogram, thoracic impedance, electrodermal activity, and electromyogram. Additional sensors may be integrated into the chair to detect the physiological state of the user including but not limited to pressure sensors in the feet of the chair to detect the center of gravity of the user, which shifts during respiration; accelerometers in the chair to detect slight changes in position; an integrated EEG headset, a pressure sensor in the seat of the chair to sense user center of mass, pressure sensors in the handrests to detect tension in the hands; an integrated camera for facial and eye detection metrics including pupil dilation; temperature sensors.

Disclosed herein are embodiments of a wearable device to translate music into vibrations. Reference is made particularly to U.S. Provisional Application No. 62/791,848 for "Tactile Stimulation Vest", the disclosure of which is incorporated herein by reference.

The system described here may apply vibration to the body of a user. The system may include at least one vibration producing device including at least one motor with an axle and at least one unbalanced rotating mass mounted on the axle, wherein the at least one unbalanced rotating mass is coupled to the axle at a point offset from its center of mass, producing a vibration in the at least one motor when the mass is rotated, and wherein the device is configured to deliver the vibration to at least a portion of a body. The system may also include an input signal, wherein the input signal is directed to or from a user, at least one signal analyzer that analyzes the input signal to generate an analyzed signal and a motor drive waveform based on the analyzed signal, and a controller that is programmed to control the at least one vibration producing device using the motor drive waveform, to produce the vibration based on the input signal, such that the system applies the vibration based on the input signal to at least a portion of the body of the user.

The system may make use of an audio signal having spectral content in at least one frequency band. The audio signal may be a stereo audio signal. Alternatively, the signal may comprise a video signal having spatial content. In other embodiments, the signal may be based on a sensor output, wherein the sensor is sensing a piece of bioinformation related to the body of the user. The signal analyzer may be at least one analog filter, digital filter, spectrum analyzer, or Fourier transformer In an exemplary embodiment as depicted generally in FIG. 11, a vest 101 may be made of a stretchy material that conforms and compresses to the body. There are different sizes to fit different-sized users. To assist in putting on the compression vest there are a plurality of metal clasps running up the front of the vest. On one side are metal hooks, on the other side a loop that it mechanically locks into. The clasps allow a user to stretch the vest and hook into place. This makes it possible for the vest to be zipped up. In another embodiment the vest can use another fastening architecture such as but not limited to hook and loop fastener, snaps, buttons, buckles, and zippers.

In embodiments, sewn into the vest are pockets for the vibration motors 100. The pockets may provide a chamber large enough for the motors to fit inside. One end of the pockets may be left open. The opening may be approximately half the size of the width of the motors. The allows the motors to enter the chamber when the material is stretched, and then remain secured inside the pocket. The opening also allows a path for the wire connecting the motors to the control unit.

In another embodiment the motors can be held in place using other methods, such as hook and loop fastener on the motors and the vest, or sewn directly into the vest material.

In embodiments, a vest may be composed of two layers of fabric. One layer serves as the main structural layer. The other layer creates the other side of the pocket for the motors and serves as a cover for the wires. The wires run from the motors in the pockets through the interior portion between the two layers to a central point.

In one embodiment this central point is where the wires are gathered before running through a sheath to a control box. The combination of wires and sheath may be referred to as the tether, which connects the vest physically and electrically to the control box.

In another embodiment, the wires are gathered at a singular place where they are connected to a control unit integrated into the vest.

The location of the vibration motors and/or nodes in the vest varies depending on the application. One configuration is for the motors to be placed symmetrically on either side of the spine, starting at the base of the spine, corresponding in height to the waistband of the vest. And running to the base of the neck. Additional pockets may be placed over the trapezius muscles.

In the front, motors may be placed symmetrically on the vertical center axis of the user with an approximately 2-inch gap between them and just above the waistband. Two more motors may be placed at top of the vest, corresponding to the top of the pectoral muscles.

In embodiments, on the back of the vest motors may be specifically placed starting at a height of no more than 3 cm above or below the L4 vertebrae and symmetrically on either side of the spine with a distance to the inside of the motor between 1 cm and 20 cm.

Subsequent motors may be placed in the same relative position to the L2. T12, T10, T8, T6, T4, T2, and T1 vertebrae.

In embodiments, on the front of the vest motors may be placed in correspondence with the ribs. Starting at the top the motors are placed symmetrically about the vertical center line of the body at a height no higher than 3 cm above or below rib 1, and more than 1 cm from the center line, but not more than 20 cm to the inside of the motor.

Subsequent motors may be placed in similar positions in height and centerline to ribs 3, 5, 7, 9, 11.

Each node may be controlled independently by one or more computers.

In embodiments, locations may be chosen in a manner to establish proximity to specific mechanoreceptors networks present in the participant's body. Overly sensitive locations may be avoided.

In another embodiment, when the vest is meant for treating cystic fibrosis or other respiratory issues, the motors and pockets may be evenly spaced following a curved path corresponding to the shape of the outer lobes of the lungs. The motors and pockets may be symmetric starting just below the clavicle and follow the lungs down the front of the chest, under the arm and up the back between the scapula and the spine.

In embodiments, the Tactile Stimulation Vest software may be run by a microcontroller. It may be adapted and configured to run a preprogrammed sequence or a generated sequence. The control sequence can be generated, for example, by a mathematical algorithm; from manually entered values; by music attenuated/accentuated sequence; or directly from any audio file.

Figure 23:
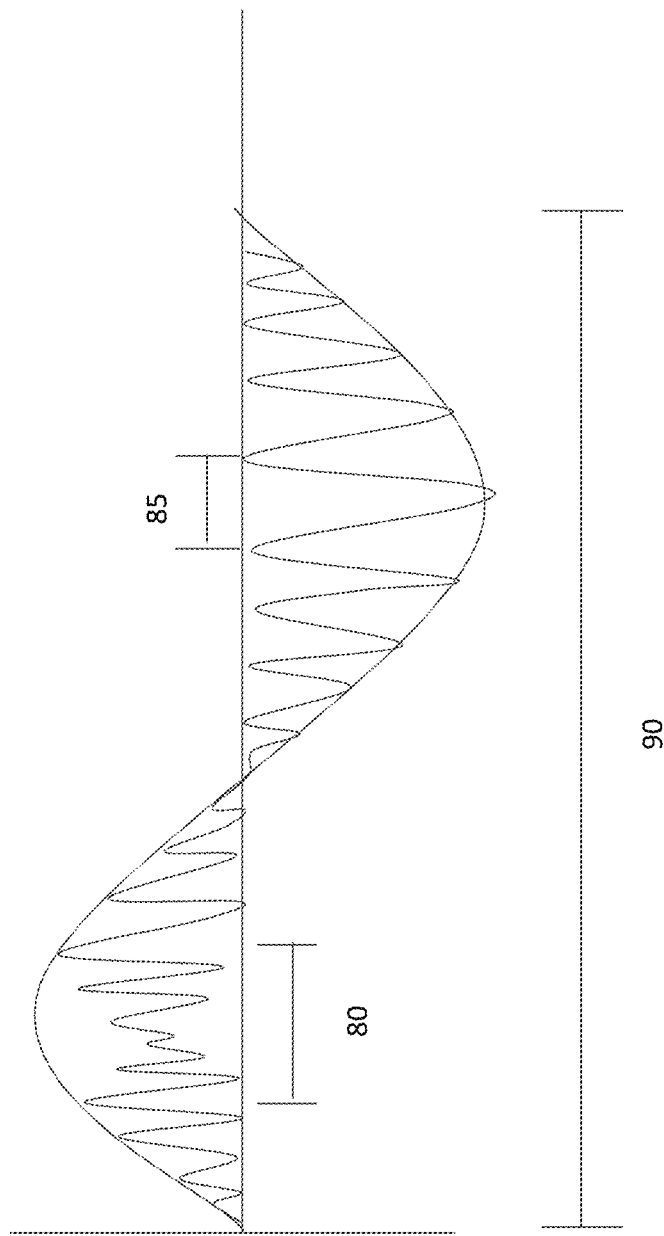
FIG. 23 shows the three different frequencies of vibration created by the device.

Programmed sequences may alter the frequency and amplitude of each motor. The motor produces a primary frequency 85 and amplitude of vibration in FIG. 23. These programmed sequences create envelopes of vibrations with specific envelope shapes and periods. Envelope shapes may be, but are not limited to, sine waves (FIG. 23), square waves, sawtooth waves, inverse sawtooth waves, triangle waves, and arbitrary waveforms. Each envelope can have an associated period 90.

In embodiments, a vest may have any number and/or placement and/or type and/or arrangement of tactile transducers found useful for an application of interest.

In one embodiment the software is an application by which a user creates a sequence, which could be the user's own sequence or a sequence that other users create. Users can download sequences from the internet created by any other user.

In embodiments, a mathematical equation may be created to control the intensity of the individual motors over time according to a suitable algorithm. In an example embodiment the algorithm may have components as follows:

$$\text{Intensity Output} = (IMAX-IMIN)/2 * \operatorname{Sin}(2\pi w * RAD(t + MD + BQ) - \pi/2) + (IMAX + IMIN)/2$$

t (seconds): Time w (Frequency): This is the rate with which the motors change intensity. In a sinusoidal expression it is the inverse of the peak to peak time of the sin wave.

IMAX (Maximum Intensity): This is the peak intensity the motors reach. In the algorithm it is between 0-100. This is later transposed through software to a PWM signal between 0-4095.

IMIN (Minimum Intensity): This is the minimum intensity that the motors reach. It provides a floor in the algorithm value, somewhere between 0-100 intensity, again transposed to a PWM signal between 0-4095.

MD (Motor Delay): This affects the timing between sequential motors. For example, a motor delay of −1 added to motor 2 will cause it to be delayed by 1 second. Generally, this delay is applied to all the motors so that each sequential motor is delayed by the specified amount in respect to the prior motor. This may be applied with symmetry so that delay on the left and right side motors is identical. In other words, motors 2 and 10 may be delayed identically from motors 1 and 9, respectively. The intent is to create a cascade in amplitude symmetrically up and down the body.

BQ (Bilateral Quotient): This parameter affects the left-right symmetry of the intensity of the motors. When the bilateral quotient is zero the left and right motor pairs (1 and 9, 2 and 10, 3 and 11, . . . ) receive the same intensity. When the bilateral quotient is applied, the left motors are advanced or delayed in respect to the right side motor intensity. In the most binary form this would cause all the left motors to be turned on, then the right side motors. Applying this to a sine wave may cause a shifting from left to right of motor intensity. In one embodiment the algorithm uses a sine wave to generate the signal. In one embodiment the algorithm uses a square wave. In one embodiment the algorithm uses any arbitrary wave function or mathematical formula.

In an exemplary embodiment, a way to create a sequence is by entering values into a spreadsheet where columns correspond to each of the motors and each row represents a unit in time. The value in each cell, between 0-100, then represents the power intensity of each motor at a specific time. The 0-100 intensity corresponds to sending a PWM signal between 0-4095. By entering a value between 0-100 in each cell a sequence is created that later the software interprets and sends as command signals to each of the motors.

In one embodiment each row represents 1 second and there are 16 columns corresponding to the 16 motors. This makes it possible to control the voltage sent to each motor for every second of time during the routine. Each of the motors is assigned a sequential motor value from 1-16, in the case of 16 motors. Symmetry is created between the motors on the left and right side, with the right side arbitrarily numbered 1-8 and the left numbered 9-16.

In embodiments, a music signal is split so that part goes to a set of headphones or speakers for the user to hear. The other part is processed by software to then affect the haptic transducers.

In one embodiment the music signal is analyzed to measure amplitude in the 1-250 Hz frequency range. This sub-bass and bass frequency (BF) range amplitude, expressed as Standard Deviation (STD-BF), is calculated over a 200 millisecond moving time window and is compared to the Standard Deviation (STD-MS) of the music signal, from 20-10 kHz, calculated over a 5000 millisecond moving time window.

In embodiments, when STD-BF exceeds 1.5*(STD-MS), this is considered an event. When an event occurs, a signal is sent to the control software. The haptic transducers will be running a preprogrammed routine, which may be a constant frequency, or a regular repeating sequence, or any combination of frequencies. When an event is sent to the control software it immediately modifies the routine. One modification could be to cause the haptic transducers to have their power cut to 0% and then ramped to a power level between 20 and 100% over a time period of 100-250 ms. The determination of the power level delivered to the haptic transducers can be preset or can be proportional to the STD-BF.

In one embodiment the music signal is analyzed to measure amplitude in the 1-250 Hz frequency range. This sub-bass and bass frequency (BF) range amplitude, expressed as Standard Deviation (STD-BF), is calculated over a 200 millisecond moving time window and is compared to a variable threshold (VT-BF) derived from STD-BF.

In embodiments, the VT-BF may be derived as follows:

a. Peak detect STD-BF b. Peak detector decays at the rate of 20% per second c. Threshold (VT-BF) is set to 75% of the peak detector value STD-BF and VT-BF are compared. The gain of STD-BF is adjusted so that the comparator output reliably indicates the presence of bass (rhythm) via an event.

In embodiments, when an event occurs a signal may be sent to the control software. The haptic transducers will be running a preprogrammed routine, which may be a constant frequency, or a regular repeating sequence, a preprogrammed sequence, a mathematically derived sequence, or any combination of these. When an event is sent to the control software it immediately modifies the routine. One modification could be to cause the haptic transducers to have their power cut to 0% and then ramped to a power level between 40 and 100% over a time period of 100-250 ms.

In embodiments, a music waveform or motor drive signal may be expressed by a plurality of wearable haptic transducers. The music may be analyzed to isolate different frequency spectrums. An event that occurs in each frequency spectrum may trigger a specific sequence. For instance an event in the sub bass and bass spectrum (1-250 Hz) may cause a momentary drop of all haptic transducers followed directly by a pulse to all transducers. An alternate sequence is to cause a sequential increase in intensity of each of the haptic transducers. The effect is a wave of intensity increase in the haptic transducers starting with the lower transducers, or starting at the upper transducers and traveling to the lower transducers, or starting in the middle transducers and traveling to the outer transducers.

In embodiments, the power delivered to the haptic transducers can be preset or can be proportional to the power of the music in that specific frequency range.

One aspect of a vest according to the disclosure hereof is that it can integrate with the human nervous system to form a complete system for affecting a person's physical, mental and/or emotional states.

In one embodiment, the motors perform specific sequences of frequency and amplitude modulation that work in concert to affect the afferent nervous system through the body's mechanoreceptors. Through the afferent nervous system, the device affects different parts of the brain and other parts of the nervous system. In this respect, the parasympathetic nervous system is being used as an input mechanism for affecting a person's mental, emotional and physical state.

In embodiments specific upregulation or downregulation of a state of physiological readiness may be indicated by a Flow Index such as given by the formula:

Flow Index=[Mean(HR)After−Mean(HR)Baseline]/Mean(HR)Baseline+[(HRV)After−(HRV)Baseline]/(HRV)Baseline+[Mean(RR)After−Mean(RR)Baseline]/Mean(RR)Baseline+[Mean(RD)After−Mean(RD)Baseline]/Mean(RD)Baseline d. [STD(CEMG)After−(STD(CEMG)Baseline]/[5*STD(CEMG)Baseline]

Wherein
HR=Heart Rate
HRV—Heart Rate Variability
RR=Respiration Rate
RD=Respiration Depth (Peak-Peak)
CEMG=Corrugator Electromyographic Activity
Flow Index indicates a state of physiological readiness. Anything above 0 indicates more physiologically ready. Scale is 0-1.

In embodiments, a tactile stimulation vest can be used in conjunction with a virtual reality (VR) or augmented reality (AR) headset. The vest may act in concert with what is being displayed in the VR headset. For instance, if an ocean wave is crashing the haptic transducers may have a wave of vibration over the user. In another VR experience a user may get hit by an object and the haptic transducers in the corresponding area of the body will vibrate.

In embodiments, specific motor types are assigned a frequency spectrum. Much like a speaker may have a subwoofer, a mid-range, and a tweeter speaker. The device will then have a plurality of vibrators suited for each vibration frequency spectrum.

Generally speaking the larger motor with a larger eccentric weight will operate at a lower vibrational spectrum we characterize as 5-25 Hz. A mid-range motor will have a spectrum of around 25-60 Hz. A high range will have a spectrum from 60-300 Hz.

The device operates by inputting an audio signal. This signal is broken into 3 separate frequency bands representing the bass, the mids, and the highs. We use the conventional definition of:
Bass=20-250 Hz
Midrange=500-2000 Hz
High range=5000-10,000 Hz
The music band signal processing works as follows:
1) music signal from phone or iPod type player introduced to gain control potentiometer to buffer amplifier
2) signal then directed to highpass filter, then low pass filter, then absolute value converter
3) signal is then directed to the lowpass filter which becomes magnitude envelope (ME) output, and ME output drives the differentiator to provide a derivative magnitude output (DME).

One drive modality is to pulse the motors. A pulse is essentially a square wave that turns all the motors on in that specific frequency and vibration class. A low frequency or bass audio signal will trigger a square wave to be sent to the low-frequency motors. The amplitude of the volume of the audio signal in that spectrum will be proportional to the intensity of the signal sent to the motors. For example, a 0 dB audio frequency represents full volume and will trigger a 100% intensity driving of the eccentric motors. In another embodiment, the output signal is sent to a voice coil activated linear actuated mass haptic transducer. In the current hardware architecture, this is represented by sending a PWM signal of 0-4095. 0 is related to zero audio signal, and 4095 representing full audio volume.

One embodiment of the vest where the shoulders have high range mechanical transducers related to treble. The upper back has mid range transducers. The mid-upper back has low range transducers, relating to the audio frequency felt by a subwoofer. The lower back and upper part of the glutes have 4 more mid-range transducers. Each of the transducers can be independently controlled to maximise user experience. This configuration can also serve as a model for use in the back of a chair for a theater experience.

One embodiment of the vest where the shoulders have high range mechanical transducers related to treble. The upper back has mid range transducers. The lower back has low range transducers, relating to the audio frequency felt by a subwoofer. The upper part of the glutes has 2 more mid range transducers. Each of the transducers can be independently controlled to maximize user experience.

In one embodiment the front of the vest has 2 treble transducers located at the top of the pectoral muscles, 2 midrange transducers located over the pectoral muscles, and 2 more midrange transducers located at the lower part of the belly. Each of the transducers can be independently controlled to maximise user experience.

In one embodiment the transducers can be integrated into a chair. This acts as a 3 channel vibrotactile system to enhance the experience, whether that be listening to music, watching a movie or show, playing video games, sharing a tactile experience online, or driving a car.

In one embodiment the chair is an office style chair.
In one embodiment the chair is a theater chair.
In one embodiment the chair is a lounge chair. In one embodiment the chair is car seat.

In an embodiment, the audio signal is separated using an analog hardware approach. Input music signal is simultaneously split into three different frequency bands, employing analog biquad active filters. Filters employ second-order biquads for the low and high frequency cutoffs for each band. The filters are of maximally flat design (e.g. Butterworth).
Bass=20-250 Hz
Midrange=500-2000 Hz
High range=5000-10,000 Hz
The energy in each filter band is tracked using an envelope detector (ED). The output of the ED is known as magnitude envelope (ME). The ED consists of an absolute value converter followed by a 10 Hz, biquad, butterworth, low pass filter. The output from the ED is sampled by the host microcontroller to be used as a signal drive to control the PWM drive to all the vest motors.

In one embodiment, the ME output of the ED can also be differentiated to provide a derivative of magnitude envelope (DME). Either the ME or DME can be employed as the PWM control drive signal.

The lower frequency and high intensity beat frequency 80, or inter-modulation frequency, of the coupled motors presents a novel way to create a low frequency that can be felt. A single eccentric rotational mass motor needs velocity to create enough momentum to be felt with any reasonably wearable size motor. And even with the speaker coil style driver, there is a limit to how low the frequency can be with a reasonably sized mass.

In embodiments, a coupled motors system produces a constructive and destructive wave, the beat frequency 80, that can be felt by even two small motors interacting. The beat frequency 80 is used to match the human heart rate and other periodic physiological processes to affect a person's physiological, mental, and emotional states.

In embodiments, a coupled ERM motor system is disposed in a wearable, such as a wristband or wristwatch. The wearable simultaneously tracks heart rate, while calculating HRV, and activates and adjusts the coupled ERM motors to produce a beat frequency 80 to affect heart rate.

In embodiments, the system may be applied for any one of: diabetes, PTSD, cystic fibrosis, bone healing, arthritis, lymphedema, ischemia, thrombosis, Klippel Trenaunay.

Figure 24:
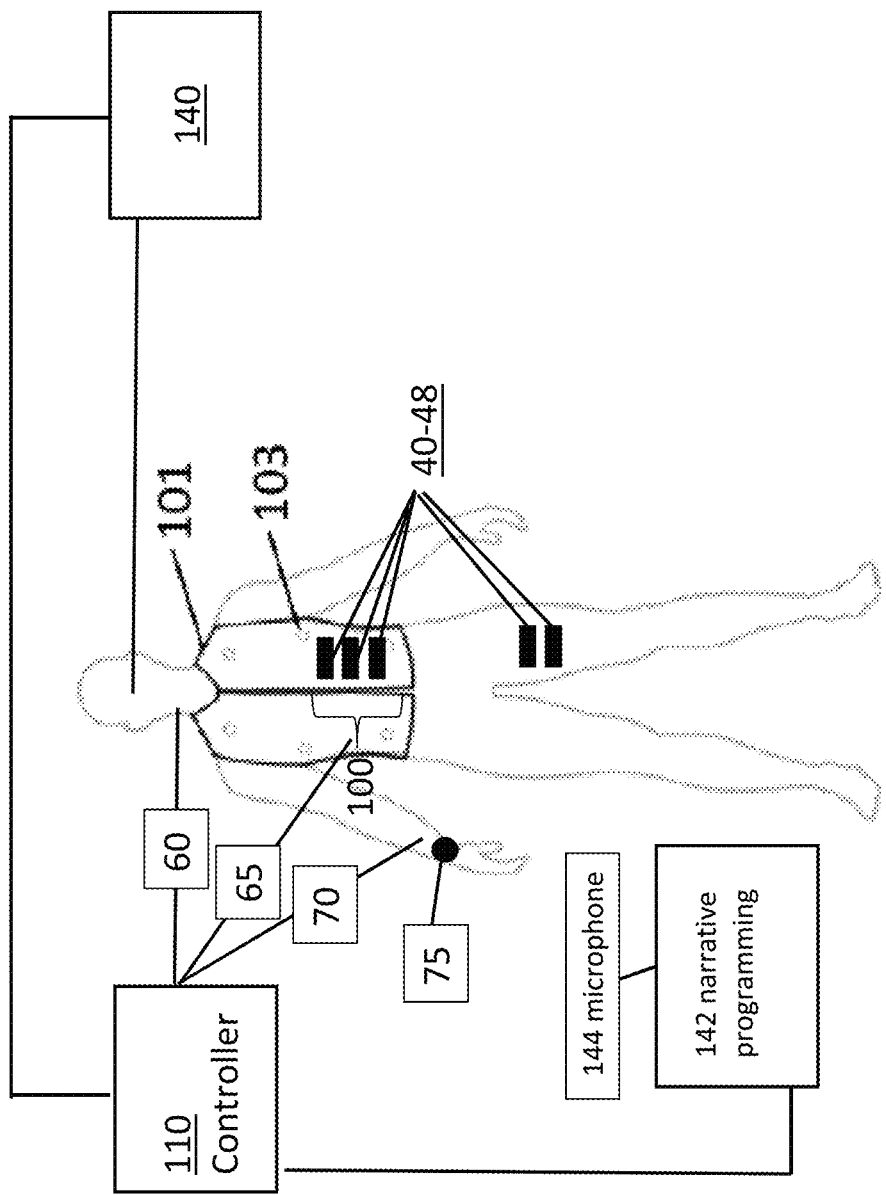
FIG. 24 shows a generalized diagram illustrating the addition of narratives, sensations, and bio-active compounds to the system.

In other embodiments, additional sensations may be added to the experience of the user using the vibration producing systems described above and illustrated in the foregoing figures. These embodiments may be illustrated generally in FIG. 24. FIG. 24 shows the addition of a compound dispenser 140, a narrative module 142 and a microphone 144. It should be understood that not all of these elements may be required to practice this invention, that some are optional, and that the invention is bounded only by the appended claims.

In some embodiments, rather than or in addition to a musical audio signal, the audio signal may instead be a narrative that may include musical elements as represented by module 142. The narrative may be, for example, a story, or a sequence of evocative sounds such as rainfall, breaking ocean waves, thunder, birdsong. The narrative may also include a plot or story line. This plot or story line may include the user as a character in the narrative.

The audio sequence may be played to the user while the user is also experiencing vibrations produced by the at least one vibration producing device. As before, the vibration producing device may have at least one motor with an axle and at least one unbalanced rotating mass mounted on the axle, wherein the at least one unbalanced rotating mass is coupled to the axle at a point offset from its center of mass, producing a vibration in the at least one motor when the mass is rotated, and wherein the device is configured to deliver the vibration to at least a portion of a body. The vibrations may be associated with certain passages in the narrative, and in particular, certain audio sequences. The audio sequences may be designed to capture the attention of the user and involve the user in the narrative. In some embodiments, the audio signal may be the user's own heartbeat, as recorded by a recording device or microphone 144.

For example, an increase in the audio sound level may be associated with an increase of vibration magnitude and/or frequency. A sudden cessation of audio sound may be accompanied by a cessation of the vibration. These sudden changes may exert control over the user's attention, and involve the user more fully in the narrative. In short, the audio narrative may be associated with sudden or abrupt changes in vibration magnitude and/or frequency.

As before, these changes in waveform patterns may be produced by the controller that controls the individual motors. In addition to sudden changes in volume or amplitude, the audio signal may include patterns that are deeply evocative to the users, such as a heartbeat. The heartbeat may be the user's own heartbeat, or it may be the heartbeat of a close friend, partner or colleague. The heartbeat may increase in synchrony with inhalation, and decrease with exhalation. The controller may alternatively activate the vibration when the user is inhaling, and cease or disable the vibration when the user is exhaling. This may accomplish the raising or lowering of the respiration pattern of the user, or allow its synchronization with the audio signal.

The term "abrupt changes in volume" may be understood to mean when the volume or magnitude of the audio signal changes from audible to inaudible within or less than one (1) second. In other embodiments, the "abrupt change in volume" may be reduction of the amplitude by at least a factor of 5 in less than 1 second, wherein the substantially abrupt changes are based on the narrative. The narrative, plot, story or game may be stored in a software module 142, coupled to the controller.

A microphone, 144, may be deployed near the user to record the utterances of the user. In some embodiments, the narrative may be altered based on the utterances. For example if the user utters "more" or "don't stop" the controller may repeat some passages of the audio file, and thereby the accompanying activation of the vibration producing device. The controller may also add the user's utterances to the narrative, thereby again capturing the attention of the user for extended periods. In other embodiments, the user can alter the narrative as in a role playing game, by saying "climb", "shoot" or other such action terms. In this embodiment, the systems may be, in effect, a full body, fully immersive video game or role playing game.

In other embodiments, the narrative may be associated with the administration of a compound that may alter the user's mood, cognitive abilities, thoughts, attention or reflexes. The compounds may be one or more of any of the following: hormones, depressants, amphetamines, psychoactive compounds, therapeutic compounds, and bio-active compounds in general. This list is not meant to be exhaustive, but rather exemplary of the compounds which may be administered. The compound may in addition to or alternative to, compounds which may evoke a sensation, such as volatile olfactory compounds, or food substances or seasonings or aromas.

In other embodiments, the input signal including an attention-getting impulse function may be a quality or an experience. For example, the user may experience a loud sound, a smell or a taste. In any case, the impulse function sensation may be associated with a specific vibration pattern generated by the controller and executed by the unbalanced motors. For the user using the system in this mode, going forward, after the session, the sensation of the impulse function or sequence may be associated with the vibration pattern in the mind of the user, such that the pleasant feelings of relaxation and well-being are experienced later, even without the vibration-producing device being present That is, the user has learned to associate the pleasant experience of the vibration with the impulse function or sequence, so that a later experience with the impulse function or sequence will elicit a response similar to the response of the whole vibration system.

The term "impulse" as used herein refers to a sensation that has a rapid onset, and optionally also a rapid diminution. More specifically, the rapid onset of an impulse function or sequence may transition from beneath a sensory or background threshold (un-sensed) to above the sensory or background threshold (sensed) in less than, or equal to one (1) second. Similarly, the impulse function or sequence may be quenched (from sensed level to un-sensed level) in less than, or equal to one (1) second. These impulse functions are distinguished from a normal start and finish of an audio signal by their repeated occurrence in the narrative, and by their appearance within a narrative, that is, they may appear in the midst of other, ongoing audio signals such as music. The on/off pattern of the impulse function or sequence may be rising from imperceptible compared to the background signal, to an amplitude 2× to 100× the level of the background signal in less than, or equal to one (1) second.

The impulse can be with respect to any individual or combination of sensations, including olfactory, audio, visual, or tactile, for example.

In other embodiments. The vibration algorithm and narrative or sequence may be applied to the user in conjunction with a bio-active compound. The compound may be ingested or applied from a source 140. The compound may be a pharmaceutical, or a hallucinogen or psychedelic compound, or mood-altering compound such as ethyl alcohol, nitrous oxide, depressants, stimulants, a vitamin, a supplement, a hormone, or a taste, for example. This list is not meant to be exhaustive, but rather exemplary of the compounds which may be administered. When these bioactive compounds are applied or ingested prior to or during the narrative and in association with the vibration producing device, the vibration producing device and narrative may serve to amplify the sensation to the user, or to affect the duration or intensity of its effects on the user. For example, the user may metabolize alcohol at a different rate, or experience an increase in drug reaction for a given dose, while using the vibration-producing system. Accordingly, a duration and amplitude of the psychoactive effect of the compound may be altered by the system.

Used in this mode, the user can be prompted to recall that sensation of well-being even when the user is not using the vibration producing system. In this embodiment, after at least one training session, wherein for example, a stressed individual is calmed by exposure to the vibration producing system and the stimulating compound, that feeling may be recovered later even when the user is no longer using the system. Application of the bioactive compound may cause the user to recall the feeling of well-being, even without the vibration producing device. This effect may be similar to techniques used in hypnosis, wherein upon the hearing of the words or phrases associated with the hypnotic state in at least one training session, the user is returned to the hypnotic state upon hearing that word or phrase. Accordingly, the system may include a second vibration producing device, wherein the second vibration producing device is wearable, and includes a second controller which controls the vibration produced by the second vibration producing device. The second controller may direct the second vibration producing device to produce vibrations based on a previously experienced narrative.

In other embodiments, the vibration producing device as described above may be used in conjunction with another, wearable vibration producing device. After the training described above, wherein the user learns to associate a pattern of vibration with a sense of relaxation or well-being, the wearable device may apply a vibration reminiscent or evocative of the pattern that induced that feeling of well-being or relaxation. Using the wearable vibration producing device, the user can be prompted to recall that sensation of well-being even when the user is not using the initial vibration producing system used during the training session. In this embodiment, after at least one training session, wherein a stressed individual is calmed by exposure to the vibration producing system and narrative or sequence, that feeling may be recovered later even when the user is no longer using the system. This effect may be similar to terms used in hypnosis, wherein upon the hearing of the words or phrases associated with the hypnotic state in at least one training session, the user is returned to the hypnotic state upon hearing that word or phrase. Accordingly, the system may include a second vibration producing device, wherein the second vibration producing device is wearable, and a second controller which controls the vibration produced by the second vibration producing device. The second controller may direct the second vibration producing device to produce vibrations based on a previously experienced narrative.

In one embodiment a user experience may combine many of the above situations and, for example, takes a drug compound, utilize the vibration producing device in a journey, express an utterance which causes the controller to modify the output of the vibration producing device, as a training for the user.

In one embodiment a user applies the device by, but not limited to sitting in a chair, putting on a vest, applying a headband, or sitting on a cushion. The user may or may not also apply sensors 60, 65, or 70. The user may or may not apply a blindfold. A narrative is then played for the user that takes them through a specific journey. The narrative may use, but is not limited to audio, visual, and vibratory stimuli. The narrative may consist of, but is not limited to voices, music, nature sounds, human sounds, a user's own biometrics such as a heartbeat or respiration, another person's biometrics, animal sounds, pulsing lights, colored lights, complete darkness, and vibrations of varying frequency and amplitude. The narrative guides the user on a journey to affect their psychophysiological state. For example, a narrative may include elements of sound, vibration, and visual stimuli to activate a user's sympathetic nervous system and then deactivate the sympathetic nervous system. Similarly the narrative may reduce and increase parasympathetic nervous system activity. The narrative may also include descriptions that the user may use to visualize themselves in various situations. Examples of such audio descriptions through sounds and voice are flowing down a river, going over a waterfall, jumping out of a plane, being launched in a rocket ship, riding a tiger, floating on water, or diving underwater. The narrative may include explicit directions for the user such as focusing and relaxing certain parts of the body. The narrative may contain explicit directions on how the user is to breathe. In this manner the narrative creates a multi-sensory experience that simultaneously guides a user through a mental and physical experience.

In one embodiment the user is instructed to inhale when the vibrations are increasing in intensity and exhale as the vibrations are decreasing in intensity. In other embodiments the narrative guides the user to breathe at a faster than normal rate or at a slower than normal rate. The coupling of vibrations and breathing integrates both the user's cognition and physiology in the narrative.

In one embodiment the user wears another portable device, a wearable. The wearable may be, but is not limited to a bracelet, a headband, an ankle cuff, a backpack, a harness, eyewear, footwear, gloves, an ear clip, a ring, a hat, a helmet, or any garment. While experiencing the narrative of the primary device the wearable device generates its own stimulus that may be vibrations, heating, cooling, scent, sound, taste, or visual. At a later time, when the user is away from the primary device, the user activates the wearable device to conjure the psychophysiological state previously induced by the narrative. In this manner the user is trained to associate the wearable with the narrative. At a later point, the user can conjure that state induced by the narrative when the wearable is activated.

In another embodiment, the user experiences the narrative on the primary device in a training situation and then has a separate portable wearable device that is used preceding or during performance. The wearable device generates vibration envelope shapes and periods similar to those in the narrative during training. In a circumstance such as, but not limited to warfighter field use or athletes in competition, the wearable generates similar vibrations to those in the narrative to conjure a similar physiological and/or psychological state as during the narrative during training in the time of performance.

In one embodiment a user could be an athlete that uses a specific narrative in a training environment to induce a psychophysiological state for optimal performance. Later, when the athlete is performing, or competing, the wearable device produces a stimulus associated with the state of optimal performance induced by the narrative during training.

In another embodiment the user is a warfighter training for high stress scenarios, an example being entering and clearing a building. The warfighter trains using a narrative that reduces stress. In the field, the wearable device produces a signal which then conjures their stress reduction training to reduce their stress. Examples of this are, but not limited to, producing vibrations with similar envelope shapes and periods as in the narrative, a scent embedded into the wearable that is produced during the narrative, or a wearable heat source that reproduces a pattern of heating and cooling in the narrative.

In one embodiment the envelope periodicity 90 is at or near fundamental physiological periods to entrain physiological systems. The envelope periodicity can also be expressed as an envelope frequency. Examples of physiological frequencies that the envelope frequency matches or nears are: Gastric (0.04-0.06 Hz), Respiration (0.025-0.25 Hz), Heart Rate Variability (0.05-0.25 Hz), Vascular Resistance (0.05-0.25 Hz), Brain (0.02-40 Hz), cerebrospinal fluid flushing (0.01-0.25 Hz).

In one embodiment the narrative incorporates envelope periodicities to entrain physiological systems to guide and alter psychophysiological states. During the narrative specific envelope periodicities could be used, for example, to entrain respiration and heart rate variability to improve cardiopulmonary functionality and to cycle the autonomic nervous to reduce stress and improve cognitive functionality.

In one embodiment, a patient with a post-traumatic stress condition fills out a questionnaire giving any songs that remind them of the traumatic incident, maybe something they were listening to at the time or consistently during that time of life. They're also asked for current songs they enjoy, relaxes them, brings about good emotional response, etc. They are introduced to the vibration producing device, and may be given a compound, e.g. 3,4-Methylenedioxymethamphetamine, commonly known as ecstasy or molly, (MDMA) or psilocybin in a laboratory setting, under the auspices of a physician. The patient may then experience a relaxation journey in the vibration producing device, which may include achieving a synchronization of one or more physiological parameters (for example, heart rate, respiration or autonomic nervous system oscillations) with the envelope of the input signal of the vibration producing device. When the compound is taking maximal effect, the song or songs reminiscent of the time of the trauma may be delivered to the patient, and used as an input signal to the controller and thus driving the vibration producing device.

In one embodiment the session takes a specific formula: user treatment includes use of the vibration producing device with input of specific music and a compound.

In one embodiment, the device puts the user into a state of Synthetic Sleep™ by vibrating at a specific pattern to drive the user to a physiological state similar to the physiological state of deep sleep. The user is guided into a particular state, Synthetic Sleep, in which the cerebrospinal fluid pressure becomes synchronized to the vibration envelope period. In one instance, this state is when the cerebrospinal fluid (CSF) pressure changes at a period between 6 and 60 seconds. Deep sleep is characterized by an increase in CSF pressure fluctuations, volume fluctuations and changes in chemical composition of the CSF. CSF flushing occurs during deep sleep, and is thought to be a critical process during sleep for clearing metabolic byproducts from the brain. CSF can be measured by measurements of deflection of the tympanic membrane, pressure changes in the outer ear (the pressure in the sealed ear canal between tympanic membrane and seal) fMRI, spinal taps measuring pressure directly, sampling of CSF, and doppler measurements of sound, light or radio waves, for example. The term Synthetic Sleep should be understood to be a condition of the user where a biomarker normally associated with natural sleep, such as an increase of delta brainwaves, CSF pressure or volume fluctuations, or CSF flow fluctuations, occur but are driven by, and largely in synchronization with, the vibration producing device.

Figure 26:
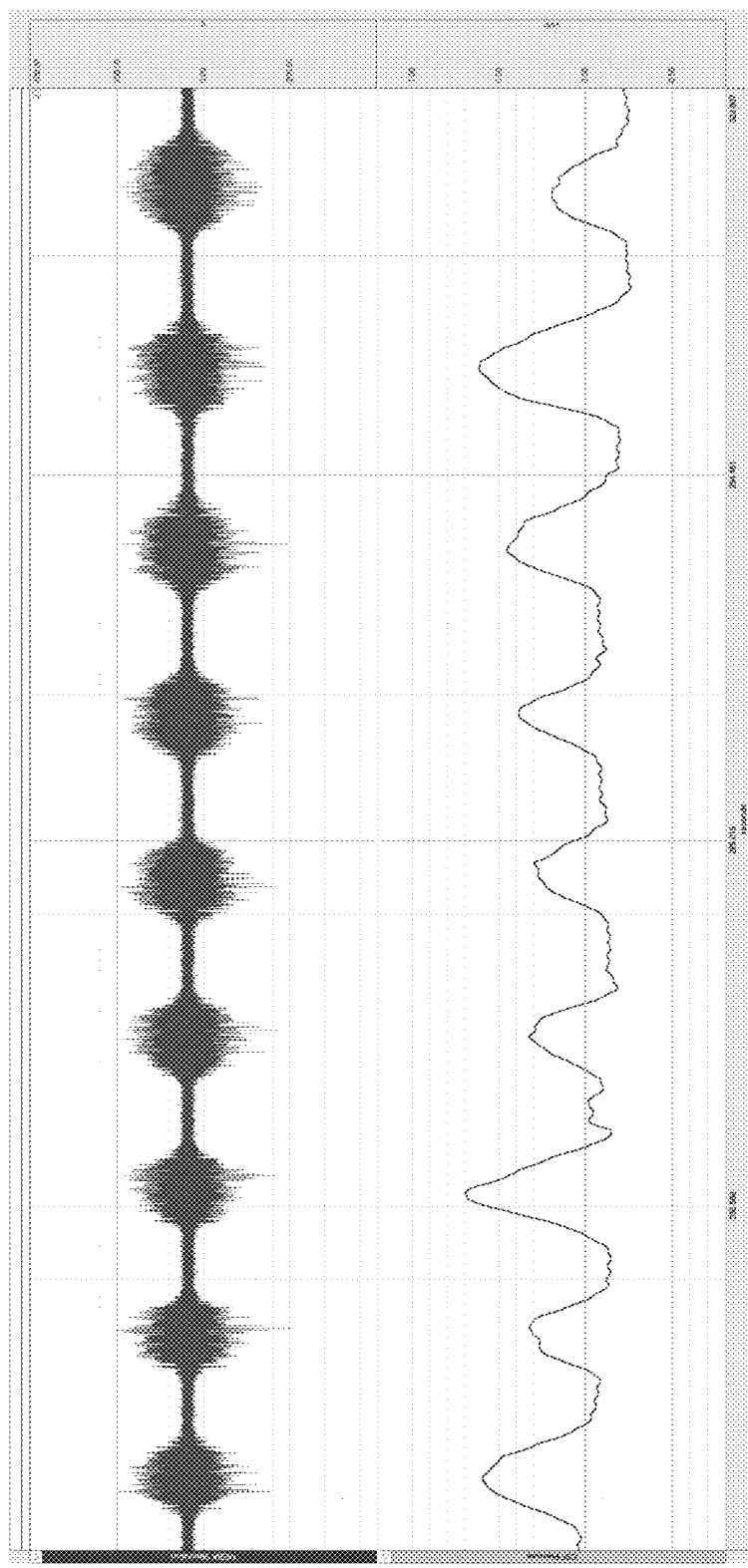
FIG. 26 shows a data pattern showing the influence of the vibration producing device on the cerebrospinal fluid (CSF) pressure.

Synchronization of the vibration producing device, such as that depicted in FIG. 9, and the CSF is illustrated by the data shown in FIG. 26. In FIG. 26, the upper trace (a) shows the envelope of the vibrations produced by the vibration producing device, wherein the envelope recurs with a period of about 10 seconds. The lower trace (b) shows the corresponding behavior of the CSF pressure, wherein the variations also have a period of about 10-15 seconds, and appear to be locked to the envelope period shown in (a).

Figure 25:
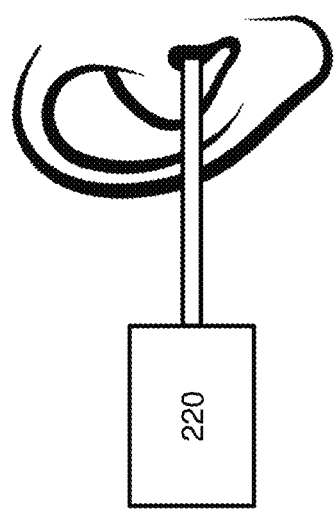
FIG. 25 shows a simplified diagram illustrating a method and apparatus for measuring cerebrospinal fluid (CSF)

In one embodiment, illustrated in FIG. 25, the device measures the pressure in the outer ear canal using a pressure sensor 220 that may be, but is not limited to, a MEMS differential pressure sensor. The pressure is measured in the outer ear which is substantially sealed from the ambient pressure surrounding the user. A typical seal must such that a leakage of less than 250 pascal per 10 seconds is achieved, thereby becoming substantially sealed. The pressure measured in the outer ear canal reflects the movement of the tympanic membrane, which in turn reflects the pressure in the cochlear reservoir which reflects the pressure of the cerebrospinal fluid (CSF) in the cranium. The measurement of CSF pressure is then indicative of CSF flushing, which has been shown to be a critical physiological function. CSF flushing increases during deep sleep, as a part of a neurological housekeeping to remove metabolites and other cellular byproducts from the interstitial spaces of the brain.

Figure 27B:
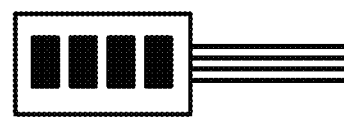
FIG. 27b is additional detail of the four-contact measurement.
Figure 27A:
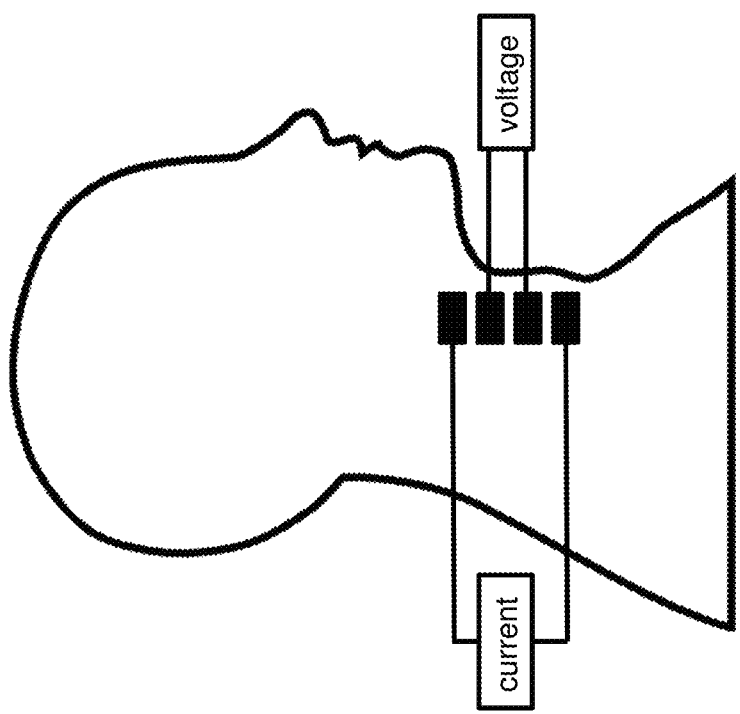
FIG. 27a is a simplified schematic illustration of an impedance transducer to measure cerebral spinal fluid flow.

In one embodiment, illustrated in FIG. 27*a* and FIG. 27*b*, the electrical impedance of tissue is measured in regions of the body, as is known in the art. The measurement can be made with 2 probes, measuring the current flowing with an applied voltage as is known in the art, but here we show an 4-probe measurement in which the two outermost probes inject current into the tissue and the inner probes measure the resulting voltage. The resulting impedance is the voltage divided by the current, and the measurement can be made at dc or at higher frequencies. FIG. 27*a* shows the placement of the 4-probe measurement with respect to the subject to be measured. FIG. 27*b* shows the strip and planar configuration of a 4-probe device which reduces noise and also provides a convenient geometry to attach to the subject.

While the impedance measurement can measure a change in CSF fluid present in the region probed, it is also understood that other fluids can contribute to the impedance such as blood flowing through arteries, veins and other capillaries and mixtures of blood, CSF fluid and interstitial fluid in the body.

In one embodiment, the device produces vibrations to drive the autonomic nervous system between sympathetic and parasympathetic states.

In another embodiment, the device produces vibrations to drive CSF flushing.

In another embodiment, the device inputs various vibration patterns and while simultaneously measuring outer ear pressure (the pressure in the sealed ear canal between tympanic membrane and seal) to determine an optimal pattern of vibration for driving CSF flushing.

In one embodiment, the optimal pattern of vibration for CSF flushing is a sinusoidal pattern with an envelope period between 10 seconds and 30 seconds.

In one embodiment, the device is programmed to vibrate at a specific envelope period measured for that specific user.

In one embodiment, the device detects when a person is in deep sleep, for example by measuring the increased amplitude of the ear membrane motion, and turns on the vibrations to optimize the CSF flushing.

In one embodiment, the device uses a closed loop feedback system to measure CSF pressure changes and adjust the vibration drive pattern to optimize the drive pattern to produce the greatest CSF pressure change.

In one embodiment, the device has a sensor that can detect when a person is experiencing sleep apnea. The controller detects the sensor and adjusts the vibration producing device by changing the amplitude and period of the envelope. The device then monitors for sleep apnea and adjusts the vibratory pattern to reduce or alleviate the sleep apnea.

In one embodiment, the device detects a sleep apnea event and triggers the device to vibrate with a specific preprogrammed pattern.

In one embodiment, the device has different vibration zones 92-98 as seen in FIG. 14. Each of the vibration zones may have a vibration producing device as shown. Each of the zones may also have its own input signal.

In one embodiment the different vibration zones indicate to the user what zone of the body to breathe into. For example, if vibrations occur in the lower thoracic region this indicates that they should breathe into their belly, or if the vibrations occur in the upper thoracic region then this indicates that they should breathe into their chest. The narrative using the different vibration zones then changes where a user is breathing in and out.

In one embodiment, the system may apply vibration to a body of a user. The system may include at least one vibration producing device, which generates a vibration of frequency between 5 and 80 Hz, that is modulated simultaneously in shape, amplitude or frequency by a modulation envelope with a frequency between 1 and 9 cycles per minute, and a controller that controls the at least one vibration producing device, wherein the controller alters at least one of the envelope frequency, envelope amplitude and envelope shape. Further, the preferred embodiment includes the at least one vibration producing device comprising a plurality of vibrating producing devices, disposed on both sides of the spine of a user. In addition, the preferred embodiment system is further comprising at least one sensor configured to measure a signal indicative of the physiological state of the user, wherein the controller is programmed to control the plurality of vibration-producing devices with a feedback loop algorithm that generates a drive signal for the at least one vibration producing device, wherein the feedback loop alters at least one of the envelope frequency, the envelope amplitude and envelope shape of a vibration, based on the output of the sensor.

Related to this US non-Provisional application are previously filed and pending US and PCT patent application Ser. Nos. 16/740,402, 16/740,401 and 16/740,399, all filed Jan. 11, 2020, and PCT/US20/41294, filed Jul. 9, 2020. Each of these prior applications is incorporated by reference in their entirety.

A system is disclosed for applying vibration to a body of a user. The system may include at least one vibration producing device, which generates a vibration of frequency between 5 and 80 Hz, that is modulated simultaneously in shape, amplitude or frequency by a modulation envelope with a frequency between 1 and 9 cycles per minute, and a controller that controls the at least one vibration producing device, wherein the controller alters at least one of the envelope frequency, envelope amplitude and envelope shape.

Within the system, the at least one vibration producing device may comprise a plurality of vibrating producing devices, disposed on both sides of the spine of a user. The system may further comprise at least one sensor configured to measure a signal indicative of the physiological state of the user, wherein the controller is programmed to control the plurality of vibration-producing devices with a feedback loop algorithm that generates a drive signal for the at least one vibration producing device, wherein the feedback loop alters at least one of the envelope frequency, the envelope amplitude and envelope shape of a vibration, based on the output of the sensor.

The at least one vibration producing device may be a plurality of vibrating producing devices, disposed on both sides of the spine of a user. The system may further comprise at least one sensor configured to measure a signal indicative of the physiological state of the user, wherein the controller is programmed to control the plurality of vibration-producing devices with a feedback loop algorithm that generates a drive signal for the at least one vibration producing device, wherein the feedback loop alters at least one of the envelope frequency, the envelope amplitude and envelope shape of a vibration, based on the output of the sensor.

The feedback loop algorithm may choose a one sensor of the at least one sensor to use to establish the feedback loop between the output of the one sensor and the plurality of the vibration producing devices, wherein the choice of one sensor is based on a correlation between the vibration envelope and the one sensor. The feedback loop algorithm may also choose one sensor of the at least one sensor to establish the feedback loop between the output of the one sensor and the signal and the plurality of the vibration producing devices, wherein a change of the one sensor is monitored as the vibration is applied and the choice of the one sensor based on the amplitude of the change in the at least one sensor.

The at least one sensor may comprise a plurality of sensors producing a plurality of outputs, and each of the plurality of outputs are ranked by its correlation between the vibration envelope and the sensor and the plurality of sensor outputs are used to modulate the envelope of the drive signal in a ratio commensurate with the at least two correlations. An averaging window between 1 to 90 seconds may be used to determine the correlations. The at least one sensor may measure a deflection of a tympanic membrane, using at least one of a reflected light source, a pressure measurement of the outer ear, and direct mechanical coupling to the tympanic membrane.

The at least one sensor may be a probe in the outer ear canal, with a substantially airtight seal, that measures the pressure in at least one of the ears. The at least one sensor may be a 4-probe electrical impedance measurement comprising an injection of a current into skin with two of the electrodes on one side of a median point, and the voltage is simultaneously measured by the other two electrodes on the other side of a median point.

The at least one vibration producing device may comprise a motor with an axle and a weight, wherein the weight is coupled to the axle at a point offset from the center of mass of the weight, such that the off center mass produces the vibration as the weight is rotated by the axle.

The feedback loop algorithm may choose at least one sensor to use to establish the feedback loop between the output of the at least one sensor and the plurality of the vibration producing devices, wherein the choice of at least one sensor is selected according to a look-up table.

A method for applying a vibration to a user is also disclosed. The method may induce a physiological state in a user. The method may include placing the user in a reclining chair or bed, applying to the user a rhythmic vibration with amplitude and frequency varying with an amplitude envelope between 1-9 cycles per minute and a frequency between 5-80 Hz, covering the user's eyes with a mask of opaque material to block out light, and placing the user in an audio environment.

The method may further comprise applying at least one sensor to the user's body, measuring at least one value from the at least one sensor, and adjusting at least one of an envelope frequency, an envelope amplitude and an envelope shape of the vibration, based on the output of the sensor. The method may further comprise measuring a pressure of the cerebrospinal fluid using the at least one sensor, and using the measured pressure to adjust the frequency, amplitude, or shape of vibrations to increase cerebrospinal fluid pressure fluctuations. The method may further comprises measuring fluid flow in the neck, and using the fluid flow to adjust at least one of a frequency and amplitude of the vibrations to increase a flow of cerebral spinal fluid to and from the head of the user, to create a feedback loop based on the measured fluid flow.

Within the method, the at least one sensor may comprise a plurality of sensors, and wherein the method may further comprise choosing a sensor from among the plurality of sensors to use to establish the feedback loop between the output of the sensors and the plurality of the vibration producing devices, wherein the choice of the sensor is related to the correlation between the vibration envelope and the sensor output or outputs.

The method may further comprise choosing, on the basis, which among the sensors to use to establish the feedback loop between the output of the at least one sensor and the signal and the plurality of the vibration producing devices, wherein the change of the output sensor or sensors is monitored as the vibration is applied and the choice of the chosen and used at least one sensor is related to the amplitude of the change in the output sensor or sensors.

The method may further comprise comparing the envelope of the drive signal to at least one output of at least one sensor disposed to the body and ranks the correlation between the vibration envelope and the one sensor. Within the method, the correlation may be ranked, and the best correlating sensor signal to the envelope of the drive signal is used to modulate the new drive signal.

Within the system, the sensor signals may be ranked based on their correlation and a multitude of sensor signals are used to modulate the envelope of the drive signal in a ratio commensurate with their correlation, and wherein an averaging window of between 1 to 90 seconds is used to determine the correlation.

The feedback loop algorithm may also choose at least one sensor to use to establish the feedback loop between the output of the at least one sensor and the plurality of the vibration producing devices, wherein the choice of at least one sensor is selected according to a look-up table.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A system configured for applying vibration to a body of a user, comprising:
   a plurality of vibration producing devices wherein:
   at least one vibration producing device of the plurality of vibration producing devices, generates a vibration of frequency between 5 and 80 Hz, with a vibration envelope that is modulated simultaneously in an envelope shape, an envelope amplitude and/or an envelope frequency by a modulation envelope with a frequency between 1 and 9 cycles per minute; and
   a controller that controls the at least one vibration producing device, wherein the controller alters at least one of the envelope frequency, the envelope amplitude and the envelope shape,
   and further comprising at least one sensor configured to measure a signal indicative of the physiological state of the user,
   wherein the controller is further programmed to control the plurality of vibration producing devices with a feedback loop that generates a drive signal for the at least one vibration producing device, and the feedback loop alters at least one of the envelope frequency, the envelope amplitude and the envelope shape of the vibration envelope, based on an output of the at least one sensor,
   wherein the feedback loop chooses a one sensor of the at least one sensor to use to establish the feedback loop between the output of the one sensor and the plurality of the vibration producing devices, wherein the choice of the one sensor is based on a correlation between the vibration envelope and the one sensor;
   wherein the at least one sensor comprises a plurality of sensors producing a plurality of outputs, and each of the plurality of outputs are ranked by its correlation between the vibration envelope and each sensor, and the plurality of sensor outputs are used to modulate the envelope of the drive signal in a ratio commensurate with the correlation.

2. The system of claim 1, wherein the plurality of vibrating producing devices is configured to be disposed on both sides of a spine of the user.

3. The system of claim 1, wherein the feedback loop chooses the one sensor of the at least one sensor to establish the feedback loop between the output of the one sensor, the drive signal and the plurality of the vibration producing devices, wherein a change of the one sensor is monitored as the vibration is applied and the choice of the one sensor is based on an amplitude of a change in the one sensor.

4. The system of claim 1, where an averaging window between 1 to 90 seconds is used to determine the correlation.

5. The system of claim 1, wherein the at least one sensor is configured to measure a deflection of a tympanic membrane using at least one of a reflected light source, a pressure measurement of the user's outer ear, and direct mechanical coupling to the user's tympanic membrane.

6. The system of claim 5, wherein the at least one sensor is configured to probe in the user's outer ear canal, with a substantially airtight seal, that measures the pressure in at least one of the user's ears.

7. The system of claim 1, wherein the at least one sensor is a 4-probe electrical impedance measurement device comprising an injection of current configured to be delivered into the user's skin with two electrodes on one side of a median point, and a voltage is simultaneously measured by two additional electrodes on another side of the median point.

8. The system of claim 1, wherein at least one of the plurality of vibration producing devices comprises a motor with an axle and a weight, wherein the weight is coupled to the axle at a point offset from a center of mass of the weight, such that the off center mass produces the vibration as the weight is rotated by the axle.

9. The system of claim 1, wherein the feedback loop chooses the one sensor to use to establish the feedback loop between the output of the at least one sensor and the plurality of the vibration producing devices, wherein the choice of at least one sensor is selected according to a look-up table.

10. A method for inducing a physiological state in a user comprising:
placing the user in a reclining chair or bed;
applying to the user a rhythmic vibration with an amplitude and a frequency varying with an amplitude envelope between 1-9 cycles per minute and the frequency between 5-80 Hz by a plurality of vibration producing devices;
covering the user's eyes with a mask of opaque material to block out light; and
placing the user in an audio environment;
applying at least one sensor to the user's body;
measuring at least one value from the at least one sensor; and adjusting at least one of an envelope frequency, an envelope amplitude and an envelope shape of the vibration, based on the at least one value of the at least one sensor;
measuring fluid flow in the neck;
using the fluid flow to adjust at least one of the frequency and the amplitude of the vibration to increase a flow of cerebral spinal fluid to and from a head of the user, to create a feedback loop based on the measured fluid flow; and
comparing a vibration envelope of a drive signal to the at least one value of the at least one sensor disposed on the user's body and ranking a correlation between the vibration envelope and the at least one value of the at least one sensor to modulate a new drive signal.

11. The method of claim 10, further comprising:
measuring a pressure of the user's cerebrospinal fluid using the at least one sensor, and
using the measured pressure to adjust the frequency, the amplitude, or a shape of vibrations to increase cerebrospinal fluid pressure fluctuations.

12. The method of claim 10, wherein the at least one sensor comprises a plurality of sensors, and wherein the method further comprises:
choosing a sensor from among the plurality of sensors to use to establish the feedback loop between the at least one output of the plurality of sensors and the plurality of the vibration producing devices, wherein the choice of the sensor is related to the correlation between the vibration envelope and the at least one sensor output.

13. The method of claim 10, further comprising:
choosing which among the at least one sensor to use to establish the feedback loop between the at least one output of the at least one sensor and the drive signal and the plurality of the vibration producing devices, wherein a change of the at least one sensor is monitored as the vibration is applied and the choice of the at least one sensor, chosen and used by the feedback loop, is related to an amplitude of the change in the at least one output of the at least one sensor.

14. The method of claim 10, wherein the correlation is ranked, and the correlation best matched to the vibration envelope of the drive signal is used to modulate a new drive signal.

* * * * *